(12) United States Patent
Robinson et al.

(10) Patent No.: US 10,330,581 B2
(45) Date of Patent: Jun. 25, 2019

(54) DEBRIS REMOVAL FROM HIGH ASPECT STRUCTURES

(71) Applicant: RAVE LLC, Delray Beach, FL (US)

(72) Inventors: Tod Evan Robinson, Boynton Beach, FL (US); Bernabe J. Arruza, Boca Raton, FL (US); Kenneth Gilbert Roessler, Boca Raton, FL (US); David Brinkley, Baltimore, MD (US); Jeffrey E. Leclaire, Boca Raton, FL (US)

(73) Assignee: RAVE LLC, Delray Beach, FL (US)

( * ) Notice: Subject to any disclaimer, the term of this patent is extended or adjusted under 35 U.S.C. 154(b) by 14 days.

(21) Appl. No.: 15/160,302

(22) Filed: May 20, 2016

(65) Prior Publication Data

US 2016/0266165 A1 Sep. 15, 2016

Related U.S. Application Data

(60) Continuation-in-part of application No. 15/011,411, filed on Jan. 29, 2016, which is a continuation-in-part
(Continued)

(51) Int. Cl.
*B08B 6/00* (2006.01)
*B08B 7/00* (2006.01)
(Continued)

(52) U.S. Cl.
CPC .............. *G01N 15/14* (2013.01); *B08B 1/00* (2013.01); *B08B 1/001* (2013.01); *B08B 7/0028* (2013.01);
(Continued)

(58) Field of Classification Search
CPC ...... G03F 7/0002; G03F 7/70925; G03F 1/82; G03F 1/84; B08B 7/0028; B08B 1/00;
(Continued)

(56) References Cited

U.S. PATENT DOCUMENTS

| 5,047,649 A | 9/1991 | Hodgson et al. |
| 5,102,768 A | 4/1992 | Light et al. |

(Continued)

FOREIGN PATENT DOCUMENTS

| CN | 1733596 | 2/2006 |
| JP | 09-260326 | 10/1997 |

(Continued)

OTHER PUBLICATIONS

"Cleaning Stick", IBM Technical Disclosure Bulletin, Dec. 1987, vol. 30; No. 7, 1 page.

(Continued)

*Primary Examiner* — Alexander Markoff
(74) *Attorney, Agent, or Firm* — BakerHostetler

(57) ABSTRACT

A debris collection and metrology system for collecting and analyzing debris from a tip used in nanomachining processes, the system including an irradiation source, an irradiation detector, an actuator, and a controller. The irradiation source is operable to direct incident irradiation onto the tip, and the irradiation detector is operable to receive a sample irradiation from the tip, the sample irradiation being generated as a result of the direct incident irradiation being applied onto the tip. The controller is operatively coupled to an actuator system and the irradiation detector, and the controller is operable to receive a first signal based on a first response of the irradiation detector to the sample irradiation, and the controller is operable to effect relative motion between the tip and at least one of the irradiation source and the irradiation detector based on the first signal.

13 Claims, 36 Drawing Sheets

Related U.S. Application Data of application No. 14/193,725, filed on Feb. 28, 2014, now abandoned, which is a division of application No. 13/652,114, filed on Oct. 15, 2012, now Pat. No. 8,696,818, which is a continuation of application No. 11/898,836, filed on Sep. 17, 2007, now Pat. No. 8,287,653.

(51) Int. Cl.

| | |
|---|---|
| B08B 9/087 | (2006.01) |
| G01N 15/14 | (2006.01) |
| G01N 15/10 | (2006.01) |
| B08B 1/00 | (2006.01) |
| G03F 7/20 | (2006.01) |
| G03F 1/82 | (2012.01) |
| G03F 1/84 | (2012.01) |
| G03F 7/00 | (2006.01) |
| G01Q 80/00 | (2010.01) |
| G01Q 20/02 | (2010.01) |
| G01Q 60/42 | (2010.01) |
| G01Q 70/12 | (2010.01) |

(52) U.S. Cl.
CPC ........... *G01N 15/1056* (2013.01); *G03F 1/82* (2013.01); *G03F 1/84* (2013.01); *G03F 7/0002* (2013.01); *G03F 7/70925* (2013.01); *G01Q 20/02* (2013.01); *G01Q 60/42* (2013.01); *G01Q 70/12* (2013.01); *G01Q 80/00* (2013.01)

(58) Field of Classification Search
CPC .... B08B 1/001; G01N 15/1056; G01N 15/14; G01Q 70/12; G01Q 80/00; G01Q 20/02; G01Q 60/42
See application file for complete search history.

(56) References Cited

U.S. PATENT DOCUMENTS

| | | | |
|---|---|---|---|
| 5,220,279 A | 6/1993 | Nagasawa | |
| 5,478,698 A | 12/1995 | Rostoker et al. | |
| 5,553,486 A | 9/1996 | Bonin | |
| 5,634,230 A | 6/1997 | Maurer | |
| 5,652,428 A | 7/1997 | Nishioka et al. | |
| 5,824,470 A | 10/1998 | Baldeschwieier et al. | |
| 5,935,339 A | 8/1999 | Henderson et al. | |
| 6,056,627 A | 5/2000 | Mizuta | |
| 6,130,104 A | 10/2000 | Yamasaka | |
| 6,175,984 B1 | 1/2001 | Prime et al. | |
| 6,263,176 B1 | 7/2001 | An et al. | |
| 6,353,221 B1 | 3/2002 | Elings | |
| 6,817,052 B2 | 11/2004 | Grube | |
| 6,840,374 B2 | 1/2005 | Khandros et al. | |
| 6,861,648 B2 | 3/2005 | Kley | |
| 6,896,741 B2 | 5/2005 | Stelcher | |
| 6,908,364 B2 | 6/2005 | Back et al. | |
| 3,002,899 A1 | 8/2011 | Wu et al. | |
| 8,287,653 B2 | 10/2012 | Robinson et al. | |
| 2002/0117611 A1 | 8/2002 | Kley | |
| 2005/0099895 A1 | 5/2005 | Maeda et al. | |
| 2005/0151385 A1 | 7/2005 | Autumn et al. | |
| 2005/0172703 A1 | 8/2005 | Kley | |
| 2005/0184746 A1* | 8/2005 | Altmann | G01Q 20/02 850/2 |
| 2005/0208304 A1 | 9/2005 | Collier et al. | |
| 2005/0242072 A1 | 11/2005 | Van Den Oetelaar et al. | |
| 2005/0255796 A1 | 11/2005 | Haga | |
| 2005/0266586 A1 | 12/2005 | Linder et al. | |
| 2006/0001438 A1 | 1/2006 | Humphrey et al. | |
| 2006/0211252 A1 | 9/2006 | Hopkins et al. | |
| 2006/0270221 A1 | 11/2006 | M'Saad et al. | |
| 2006/0270231 A1 | 11/2006 | Tran et al. | |
| 2007/0035724 A1 | 2/2007 | Banin et al. | |
| 2007/0145966 A1 | 6/2007 | Shekhawat et al. | |
| 2008/0169003 A1 | 7/2008 | Curtis | |
| 2009/0093659 A1 | 4/2009 | Freitas et al. | |
| 2010/0055349 A1 | 3/2010 | Gaitas et al. | |
| 2010/0083985 A1 | 4/2010 | Numanami | |
| 2012/0080596 A1 | 4/2012 | Vandervorst | |
| 2013/0094020 A1 | 4/2013 | Li | |
| 2014/0004345 A1 | 1/2014 | Chasiotis et al. | |
| 2014/0176922 A1 | 6/2014 | Robinson et al. | |

FOREIGN PATENT DOCUMENTS

| | | |
|---|---|---|
| JP | 2003-167003 | 6/2003 |
| JP | 2006-184081 | 7/2006 |
| JP | 2008-209544 A | 9/2008 |
| JP | 2009-006378 A | 1/2009 |

OTHER PUBLICATIONS

Zhang et al.; "Cellulose Nanofibrils: From Strong Materials to Bioactive Surfaces"; J. Renew Mater; vol. 1; No. 3; Jul. 2013; pp. 195-211.

EP Patent Application No. 08 83 2334 Supplemental European Search Report Reported dated Apr. 9, 2014.

Search Report dated Oct. 28, 2013 in Taiwan Patent Application No. 097135684, filed Sep. 17, 2008.

International Preliminary Report on Patentability and Written Opinion issued in PCT/US2017/015062, dated Aug. 9, 2018.

Translation of Description of JP 2008-209544 (Year: 2008) [Cited in related U.S. Appl. No. 15/160,263].

* cited by examiner

DEBRIS REMOVAL FROM HIGH ASPECT STRUCTURES

CROSS-REFERENCE TO RELATED APPLICATIONS

This patent application is a continuation-in-part application and claims the priority benefit of co-pending U.S. patent application Ser. No. 15/011,411 filed on Jan. 29, 2016, which is a continuation-in-part of U.S. patent application Ser. No. 14/193,725 filed on Feb. 28, 2014, which is a divisional of U.S. patent application Ser. No. 13/652,114 filed on Oct. 15, 2012 (issued as U.S. Pat. No. 8,696,818), which is a continuation of U.S. patent application Ser. No. 11/898,836 filed on Sep. 17, 2007 (issued as U.S. Pat. No. 8,287,653), all of which are incorporated herein by reference in their entirety.

TECHNICAL FIELD

The present disclosure relates generally to nanomachining processes. More particularly, the present disclosure relates to debris removal during and/or after to nanomachining processes. In addition, the debris removal processes of the present disclosure can be applied to removal of anything foreign to a substrate.

BACKGROUND

Nanomachining, by definition, involves mechanically removing nanometer-scaled volumes of material from, for example, a photolithography mask, a semiconductor substrate/wafer, or any surface on which scanning probe microscopy (SPM) can be performed. For the purposes of this discussion, "substrate" will refer to any object upon which nanomachining may be performed.

Examples of photolithography masks include: standard photomasks (193 nm wavelength, with or without immersion), next generation lithography mask (imprint, directed self-assembly, etc.), extreme ultraviolet lithography photomasks (EUV or EUVL), and any other viable or useful mask technology. Examples of other surfaces which are considered substrates are membranes, pellicle films, micro-electronic/nano-electronic mechanical systems MEMS/NEMS. Use of the terms, "mask", or "substrate" in the present disclosure include the above examples, although it will be appreciated by one skilled in the art that other photomasks or surfaces may also be applicable.

Nanomachining in the related art may be performed by applying forces to a surface of a substrate with a tip (e.g., a diamond cutting bit) that is positioned on a cantilever arm of an atomic force microscope (AFM). More specifically, the tip may first be inserted into the surface of the substrate, and then the tip may be dragged through the substrate in a plane that is parallel to the surface (i.e., the xy-plane). This results in displacement and/or removal of material from the substrate as the tip is dragged along.

As a result of this nanomachining, debris (which includes anything foreign to the substrate surface) is generated on the substrate. More specifically, small particles may form during the nanomachining process as material is removed from the substrate. These particles, in some instances, remain on the substrate once the nanomachining process is complete. Such particles are often found, for example, in trenches and/or cavities present on the substrate.

In order to remove debris, particles or anything foreign to the substrate, particularly in high-aspect photolithography mask structures and electronic circuitry; wet cleaning techniques have been used. More specifically, the use of chemicals in a liquid state and/or agitation of the overall mask or circuitry may be employed. However, both chemical methods and agitation methods such as, for example, megasonic agitation, can adversely alter or destroy both high-aspect ratio structures and mask optical proximity correction features (i.e., features that are generally so small that these features do not image, but rather form diffraction patterns that are used beneficially by mask designers to form patterns).

In order to better understand why high-aspect shapes and structures are particularly susceptible to being destroyed by chemicals and agitation; one has to recall that such shapes and structures, by definition, include large amounts of surface area and are therefore very thermodynamically unstable. As such, these shapes and structures are highly susceptible to delamination and/or other forms of destruction when chemical and/or mechanical energy is applied.

It is important to note that in imprint lithography and EUV (or EUVL) that use of a pellicle to keep particles off the lithographic surface being copied is currently not feasible. Technologies that cannot use pellicles are generally more susceptible to failure by particle contamination which blocks the ability to transfer the pattern to the wafer. Pellicles are in development for EUV masks, but as prior experience with DUV pellicle masks indicates, the use of a pellicle only mitigates (but does not entirely prevent) critical particle and other contaminates from falling on the surface and any subsequent exposure to the high-energy photons will tend to fix these particles to the mask surface with a greater degree of adhesion. In addition, these technologies may be implemented with smaller feature sizes (1 to 300 nm), making them more susceptible to damage during standard wet clean practices which may typically be used. In the specific case of EUV or EUVL, the technology may require the substrate be in a vacuum environment during use and likely during storage awaiting use. In order to use standard wet clean technologies, this vacuum would have to be broken which could easily lead to further particle contamination.

Other currently available methods for removing debris from a substrate make use of cryogenic cleaning systems and techniques. For example, the substrate containing the high-aspect shapes and/or structures may be effectively "sandblasted" using carbon dioxide particles instead of sand.

However, even cryogenic cleaning systems and processes in the related art are also known to adversely alter or destroy high-aspect features. In addition, cryogenic cleaning processes affect a relatively large area of a substrate (e.g., treated areas may be approximately 10 millimeters across or more in order to clean debris with dimensions on the order of nanometers). As a result, areas of the substrate that may not need to have debris removed therefrom are nonetheless exposed to the cryogenic cleaning process and to the potential structure-destroying energies associated therewith. It is noted that there are numerous physical differences between nano and micro regimes, for the purposes here, the focus will be on the differences related to nanoparticle cleaning processes. There are many similarities between nano and macro scale cleaning processes, but there are also many critical differences. For the purposes of this disclosure, the common definition of the nanoscale is of use: this defines a size range of 1 to 100 nm. This is a generalized range since many of processes reviewed here may occur below this range (into atomic scales) and be able to affect particles larger than this range (into the micro regime).

Some physical differences between macro and nano particle cleaning processes include transport related properties including: surface area, mean free path, thermal, and field-effects. The first two in this list are more relevant to the thermo-mechanical-chemical behavior of particles while the last one is more concerned with particle interactions with electromagnetic fields. Thermal transport phenomenon intersects both of these regimes in that it is also the thermo-mechanical physical chemistry around particles and the interaction of particles with electromagnetic fields in the infrared wavelength regime. To functionally demonstrate some of these differences, a thought experiment example of a nanoparticle trapped at the bottom of a high aspect line and space structure (70 nm deep and 40 nm wide AR=1.75) is posited. In order to clean this particle with macroscale processes, the energy required to remove the particle is approximately the same as the energy required to damage features or patterns on the substrate, thereby making it impossible to clean the high aspect line and space structure without damage. For macro-scale cleaning processes (Aqueous, Surfactant, Sonic Agitation, etc.), at the energy level where the nanoparticle is removed, the surrounding feature or pattern is also damaged. If one has the technical capability to manipulate nano-sharp (or nanoscale) structures accurately within nano-distances to the nanoparticle, then one may apply the energy to clean the nanoparticle to the nanoparticle only. For nanoscale cleaning processes, the energy required to remove the nanoparticle is applied only to the nanoparticle and not the surrounding features or patterns on the substrate.

First, looking at the surface area properties of particles, there are mathematical scaling differences which are obvious as a theoretical particle (modelled here as a perfect sphere) approaches the nanoscale regime. The bulk properties of materials are gauged with the volume of materials while the surface is gauged by the external area. For a hypothetical particle, its volume decreases inversely by the cube ($3^{rd}$ power) while the surface area decreases by the square with respect to the particle's diameter. This difference means that material properties which dominate the behavior of a particle at macro, and even micro, scale diameters become negligible into the nano regime (and smaller). Examples of these properties include mass and inertial properties of the particle, which is a critical consideration for some cleaning techniques such as sonic agitation or laser shock.

The next transport property examined here is the mean free path. For macro to micro regimes, fluids (in both liquid, gaseous, and mixed states) can be accurately modelled in their behavior as continuum flow. When considering surfaces, such as the surface of an AFM tip and a nanoparticle, that are separated by gaps on the nanoscale or smaller, these fluids can't be considered continuum. This means that fluids do not move according to classical flow models, but can be more accurately related to the ballistic atomic motion of a rarefied gas or even a vacuum. For an average atom or molecule (approximately 0.3 nm in diameter) in a gas at standard temperature and pressure, the calculated mean free path (i.e., distance in which a molecule will travel in a straight line before it will on average impact another atom or molecule) is approximately 94 nm, which is a large distance for an AFM scanning probe. Since fluids are much denser than gasses, they will have much smaller mean free paths, but it must be noted that the mean free path for any fluid can't be less than the atom or molecule's diameter. If we compare the assumed atom or molecule diameter of 0.3 nm given above to the typical tip to surface mean separation distance during non-contact scanning mode which can be as small as 1 nm, thus except for the most dense fluids, the fluid environment between an AFM tip apex and the surface being scanned will behave in a range of fluid properties from rarefied gas to near-vacuum. The observations in the prior review are crucial to demonstrating that thermo-fluid processes behave in fundamentally different ways when scaled from the macro to nano scale. This affects the mechanisms and kinetics of various process aspects such as chemical reactions, removal of products such as loose particles to the environment, charging or charge neutralization, and the transport of heat or thermal energy.

The known thermal transport differences from macro and nano to sub-nano scales has been found by studies using scanning thermal probe microscopy. One early difference seen is that the transport rate of thermal energy can be an order of magnitude less across nanoscale distances than the macro scale. This is how scanning thermal probe microscopy can work with a nano probe heated to a temperature difference of sometimes hundreds of degrees with respect to a surface it is scanning in non-contact mode with tip to surface separations as small as the nano or Angstrom scale. The reasons for this lower thermal transport are implied in the prior section about mean free path in fluids. One form of thermal transport, however, is enhanced which is blackbody radiation. It has been experimentally shown that the Plank limit for blackbody spectral radiance at a given temperature can be exceeded at nanoscale distances. Thus, not only does the magnitude of thermal transport decrease, but the primary type of transport, from conduction/convection to blackbody which is in keeping with the rarefied to vacuum fluid behavior, changes.

Differences in the interactions of fields (an electromagnetic field is the primary intended example here due to its longer wavelengths compared to other possible examples), for the purposes in this discussion, could be further subclassified as wavelength related and other quantum effects (in particular tunneling). At nanoscales, the behavior of electromagnetic fields between a source (envisioned here as the apex of an AFM tip whether as the primary source or as a modification of a relatively far field source) and a surface will not be subject to wavelength dependent diffraction limitations to resolution that far field sources will experience. This behavior, commonly referred to as the near-field optics, has been used with great success in scanning probe technologies such as near field scanning optical microscopy (NSOM). Beyond applications in metrology, the near field behavior can affect the electromagnetic interaction of all nanoscale sized objects spaced nano-distances from each other. The next near-field behavior mentioned is quantum tunneling where a particle, in particular an electron, can be transported across a barrier it could not classically penetrate. This phenomenon allows for energy transport by a means not seen at macro scales, and is used in scanning tunneling microscopy (STM) and some solid-state electronic devices. Finally, there are more esoteric quantum effects often seen with (but not limited to) electromagnetic fields at nanoscales, such as proximity excitation and sensing of plasmonic resonances, however, it will be appreciated by one skilled in the art that the current discussion gives a sufficient demonstration of the fundamental differences between macro and nano-scale physical processes.

In the following, the term "surface energy" may be used to refer to the thermodynamic properties of surfaces which are available to perform work (in this case, the work of adhesion of debris to the surfaces of the substrate and the tip respectively). One way to classically calculate this is the Gibb's free energy which is given as:

$$G(p,T)=U+pV-TS$$

where:
U=Internal Energy;
p=Pressure;
V=Volume;
T=Temperature; and
S=Entropy.

Since the current practice does not vary pressure, volume, and temperature (although this does not need to be the case since these parameters could equally be manipulated to get the desired effects as well) they will not be discussed in detail. Thus, the only terms being manipulated in the equation above will be internal energy and entropy as driving mechanisms in the methods discussed below. Entropy, since it is intended that the probe tip surface will be cleaner (i.e., no debris or unintended surface contaminates) than the substrate being cleaned is naturally a thermodynamic driving mechanism to preferentially contaminate the tip surface over the substrate (and then subsequently, contaminate the cleaner pallet of soft material). The internal energy is manipulated between the pallet, tip, debris, and substrate surfaces by the thermophysical properties characterized by their respective surface energies. One way to relate the differential surface energy to the Gibbs free energy is to look at theoretical developments for the creep properties of engineering materials at high temperatures (i.e., a significant fraction of their melting point temperature) for a cylinder of radius r, and length l, under uniaxial tension P:

$$dG=-P*dl+\gamma*dA$$

where
$\gamma$=Surface energy density [J/m2]; and
A=Surface area [m2].

The observation that the stress and extrinsic surface energy of an object are factors in its Gibbs free energy induces one to believe these factors (in addition to the surface energy density $\gamma$) could also be manipulated to perform reversible preferential adhesion of the debris to the tip (with respect to the substrate) and then subsequently the soft pallet. Means to do this include applied stress (whether externally or internally applied) and temperature. It should be noted that it is intended that the driving process will always result in a series of surface interactions with a net $\Delta G<0$ in order to provide a differential surface energy gradient to preferentially decontaminate the substrate and subsequently preferentially contaminate the soft pallet. This could be considered analogous to a ball preferentially rolling down an incline to a lower energy state (except that, here, the incline in thermodynamic surface energy also includes the overall disorder in the whole system or entropy). FIG. 6 shows one possible set of surface interactions where the method described here could provide a down-hill thermodynamic Gibbs free energy gradient to selectively remove a contaminate and selectively deposit it on a soft patch. This sequence is one of the theoretical mechanisms thought to be responsible for the current practice aspects using low surface energy fluorocarbon materials with medium to low surface energy tip materials such as diamond.

SUMMARY

At least in view of the above, there is a desire for novel apparatuses and methods for removing debris, contaminates, particles or anything foreign to the substrate surface, and in particular, novel apparatuses and methods capable of cleaning substrates with high aspect ratio structures, photomask optical proximity correction features, etc., without destroying such structures and/or features on a nanoscale.

According to an aspect of the present disclosure, a nano-scale metrology system for detecting contaminates is provided. The system includes a scanning probe microscopy (SPM) tip, an irradiation source, an irradiation detector, an actuator, and a controller. The irradiation source is configured and arranged to direct an incident irradiation onto the SPM tip. The irradiation detector is configured and arranged to receive a sample irradiation from the SPM tip, the sample irradiation being caused by the incident irradiation. The actuator system is operatively coupled to the nano-scale metrology system and configured to effect relative motion between the SPM tip and at least one of the irradiation source and the irradiation detector. The controller is operatively coupled to the actuator system and the irradiation detector, and the controller being configured to receive a first signal based on a first response of the irradiation detector to the sample irradiation, and is configured to effect relative motion between the SPM tip and at least one of the irradiation detector and the irradiation source via the actuator system based on the first signal.

In accordance with one aspect of the nano-scale metrology system in the present disclosure, the actuator system is operatively coupled to the SPM tip, and the actuator system includes a rotary actuator configured to rotate the SPM tip about a first axis.

In accordance with one aspect of the nano-scale metrology system in the present disclosure, the irradiation source is an x-ray source, a laser, a visible light source, an infrared light source, an ultraviolet light source, or an electron beam source.

In accordance with one aspect of the nano-scale metrology system in the present disclosure, the controller is further configured to generate a first frequency domain spectrum of the sample irradiation based on the first signal, generate a second frequency domain spectrum by subtracting a background frequency domain spectrum from the first frequency domain spectrum, and effect relative motion between the SPM tip and at least one of the irradiation detector and the irradiation source via the actuator system based on the second frequency domain spectrum. In accordance with one aspect of the nano-scale metrology system in the present disclosure, the controller is further configured to generate the background frequency domain spectrum based on a response of the irradiation detector to irradiation of the SPM tip when the SPM tip is substantially free from contamination.

In accordance with one aspect of the nano-scale metrology system in the present disclosure, the controller is further configured to receive a second signal based on a second response of the irradiation detector to the sample irradiation, and effect relative motion between the SPM tip and at least one of the irradiation detector and the irradiation source via the actuator system based on a difference between the first signal and the second signal. In accordance with one aspect of the nano-scale metrology system in the present disclosure, the controller is further configured to effect a magnitude of relative motion between the SPM tip and at least one of the irradiation detector and the irradiation source based on the difference between the first signal and the second signal.

According to an aspect of the present disclosure, a metrology system with a collector is provided. The metrology system includes a collector, an irradiation source, an irradiation detector, a scanning probe microscopy (SPM) tip, and an actuator system. The collector may have a first internal edge on a first surface of the collector, a second internal edge on a second surface of the collector, the second surface being opposite the first surface, and an internal surface extending from the first internal edge to the second internal edge, the internal surface defining at least a portion of a collection pocket or a collection through-hole therein. The irradiation source is configured and arranged to receive a sample irradiation from the internal surface of the collector, the sample irradiation being caused by the incident irradiation. The actuator system is operatively coupled to the SPM tip and configured to move the SPM tip relative to the collector for transfer of at least one particle or debris from the SPM tip to the collector.

In accordance with one aspect of the metrology system in the present disclosure, a width of the collection through-hole increases along a direction through the collector from the first surface toward the second surface.

In accordance with one aspect of the metrology system in the present disclosure, the first internal edge defines a rectangular outline of the collection pocket or the collection through-hole. In accordance with one aspect of the present disclosure, a length of each segment of the rectangular outline is less than or equal to 10 mm.

In accordance with one aspect of the metrology system in the present disclosure, the first internal edge defines a triangular outline of the collection pocket or the collection through-hole. In accordance with one aspect of the present disclosure, a length of each segment of the triangular outline is less than or equal to 10 mm.

In accordance with one aspect of the metrology system in the present disclosure, the first internal edge defines an arcuate cross section of the collection pocket or the collection through-hole, and the arcuate cross section is a circular, elliptical or oval outline. In accordance with one aspect of the present disclosure, the first internal edge defines a circular outline, and a diameter of the circular outline is less than or equal to 10 mm.

In accordance with one aspect of the metrology system in the present disclosure, the metrology system further includes a controller operatively coupled to the actuator system, the controller being configured to transfer a particle from the SPM tip to the collection pocket or the collection through-hole of the collector by dragging the SPM tip against the first internal edge.

In accordance with one aspect of the metrology system in the present disclosure, the internal surface of the collector forms a through-hole passage. In accordance with one aspect of the present disclosure, the through-hole passage is a truncated tetrahedron passage, a truncated conical passage, a truncated tetrahedral passage, or a truncated pyramidal passage.

In accordance with one aspect of the metrology system in the present disclosure, the SPM tip includes a tetrahedral shape, a conical shape, or a pyramidal shape.

In accordance with one aspect of the metrology system in the present disclosure, the collection pocket or the collection through-hole is removably mounted to the metrology system.

According to an aspect of the present disclosure, a particle collection and metrology system is provided. The particle collection and metrology system includes a scanning probe microscopy (SPM) tip, a stage configured to support a substrate, an actuation system, an irradiation source, an irradiation detector, and a controller. The actuation system is operatively coupled to the stage and the SPM tip, the actuation system being configured to move the SPM tip relative to the stage. The irradiation source is in optical communication with a metrology location, and the irradiation detector is in optical communication with the metrology location. The controller is operatively coupled to the actuation system, the irradiation source, and the irradiation detector. The controller is further configured to move the SPM tip from a location proximate to the substrate to the metrology location, and to receive a first signal from the irradiation detector indicative of a response of the irradiation detector to a first sample irradiation from the metrology location, the first sample irradiation being caused by a first incident irradiation from the irradiation source.

In accordance with one aspect of the particle collection and metrology system in the present disclosure, the metrology location is disposed on at least a portion of the SPM tip, and the controller is further configured to cause the first sample irradiation by irradiating the metrology location with the first incident irradiation.

In accordance with one aspect of the particle collection and metrology system in the present disclosure, the particle collection and metrology system further includes a particle collector, the metrology location being disposed on at least a portion of the particle collector. The controller is further configured to cause the first sample irradiation by irradiating the metrology location with the first incident irradiation.

In accordance with one aspect of the particle collection and metrology system in the present disclosure, the controller is further configured to transfer a particle from the substrate to the metrology location via the SPM tip.

In accordance with one aspect of the particle collection and metrology system in the present disclosure, the particle collection and metrology system further includes a patch of a material, the material having a surface energy that is lower than a surface energy of the substrate, wherein the SPM tip includes a nanometer-scaled coating of the material thereon.

In accordance with one aspect of the particle collection and metrology system in the present disclosure, the controller is further configured to effect contact between the SPM tip and the patch, thereby coating the SPM tip with the material.

In accordance with one aspect of the particle collection and metrology system in the present disclosure, the actuation system includes a tip actuation system operatively coupled to the SPM tip and a stage actuation system operatively coupled to the stage. The tip actuation system is configured to move the SPM tip relative to a base, and the stage actuation system is configured to move the stage relative to the base.

In accordance with one aspect of the particle collection and metrology system in the present disclosure, the particle collector is a collection pocket or a collection through-hole. The particle collector includes at least a first internal edge. The at least first internal edge defines one of a triangular, rectangular, circular, elliptical, or oval outline. In accordance with one aspect of the present disclosure, the first internal edge defines a triangular or rectangular outline, and wherein each segment of the triangular or rectangular outline includes a length of less than or equal to 10 mm. In accordance with one aspect of the present disclosure, the first internal edge defines a circular outline, and a diameter of the circular outline is less than or equal to 10 mm.

In accordance with one aspect of the particle collection and metrology system in the present disclosure, particle collector includes a first internal edge on a first surface of the collector, a second internal edge on a second surface of the collector, the second surface being opposite the first surface, and an internal surface extending from the first internal edge to the second internal. In accordance with one aspect of the present disclosure, the internal surface forms a through-hole passage. The through-hole passage is a truncated tetrahedron passage, truncated conical passage, or a truncated pyramidal passage.

In accordance with one aspect of the particle collection and metrology system in the present disclosure, the SPM tip includes a tetrahedral shape, a conical shape, or a pyramidal shape.

In accordance with one aspect of the particle collection and metrology system in the present disclosure, the patch is removably mounted to the stage. In accordance with one aspect of the particle collection and metrology system in the present disclosure, the collection pocket or the collection through-hole is removably mounted to the stage.

According to an aspect of the present disclosure, a method of determining a composition of a particle using a scanning probe microscopy (SPM) tip is provided. The method includes transferring the particle to the SPM tip; irradiating the SPM tip with a first incident irradiation from an irradiation source; detecting a first sample irradiation caused by the first incident irradiation with an irradiation detector; and effecting relative motion between the SPM tip and at least one of the irradiation source and the irradiation detector based on a first signal from the irradiation detector in response to the first sample irradiation.

In accordance with an aspect of the method for determining the composition of the particle on the SPM tip, the method further includes generating a first frequency domain spectrum of the first sample irradiation based on the first signal; generating a second frequency domain spectrum by subtracting a background frequency domain spectrum from the first frequency domain spectrum; and effecting relative motion between the SPM tip and at least one of the irradiation source and the irradiation detector based on the second frequency domain spectrum.

In accordance with an aspect of the method for determining the composition of the particle on the SPM tip, the method further includes generating the background frequency domain spectrum based on a response of the irradiation detector to irradiation of the SPM tip when the SPM tip is substantially free from contamination.

In accordance with an aspect of the method for determining the composition of the particle on the SPM tip, the method further includes irradiating the SPM tip with a second incident irradiation from the irradiation source; detecting a second sample irradiation caused by the second incident irradiation with the irradiation detector; and effecting relative motion between the SPM tip and at least one of the irradiation source and the irradiation detector based on a second signal from the irradiation detector in response to the second sample irradiation.

In accordance with an aspect of the method for determining the composition of the particle on the SPM tip, the method further includes effecting relative motion between the SPM tip and at least one of the irradiation source and the irradiation detector based on a difference between the second signal and the first signal.

In accordance with an aspect of the method for determining the composition of the particle on the SPM tip, the first incident irradiation from the irradiation source is at least one of an x-ray, visible light, infrared light, ultraviolet light, an electron beam, and a laser. In accordance with an aspect of the method for determining the composition of the particle on the SPM tip, the second incident irradiation from the irradiation source is at least one of an x-ray, visible light, infrared light, ultraviolet light, an electron beam, and a laser. The second incident irradiation is a different type of irradiation than the first incident irradiation. In one aspect, the first sample irradiation is generated by the first incident irradiation interacting with the SPM tip. In one aspect, the interacting may include one or more of the first incident irradiation being reflected, refracted, or absorbed and re-emitted by the SPM tip. In one aspect, the first sample irradiation is generated by the first incident irradiation interacting with debris disposed on the SPM tip. In one aspect, the interacting may include one or more of the first incident irradiation being reflected, refracted, or absorbed and re-emitted by debris disposed on the SPM tip.

In accordance with an aspect of the method for determining the composition of the particle on the SPM tip, the method further includes adjusting an intensity or frequency of the first incident irradiation from the irradiation source. In one aspect, the method further includes adjusting an intensity or frequency of the second incident irradiation from the irradiation source.

According to an aspect of the present disclosure, a method for determining a composition of a particle removed from a substrate is provided. The method includes transferring a particle from the substrate to a scanning probe microscopy (SPM) tip; irradiating the particle with a first incident irradiation from an irradiation source; and receiving a first sample irradiation from the particle at an irradiation detector, the first sample irradiation being caused by the first incident irradiation.

In accordance with an aspect of the method for determining the composition of the particle removed from the substrate, the first sample irradiation from the particle is received by the irradiation detector while the particle is disposed on the SPM tip.

In accordance with an aspect of the method for determining the composition of the particle removed from the substrate, the transferring of the particle from the substrate to the SPM tip includes contacting the SPM tip against the substrate and moving the SPM tip relative to the substrate.

In accordance with an aspect of the method for determining the composition of the particle removed from the substrate, the method further comprises transferring the particle to a metrology location using the SPM tip.

In accordance with an aspect of the method for determining the composition of the particle removed from the substrate, the method further includes transferring the particle from the SPM tip to a particle collector with a metrology location defined on the particle collector. The first sample irradiation from the particle is received by the irradiation detector while the particle is disposed on the metrology location. The transferring of the particle from the SPM tip to the particle collector includes contacting the SPM tip against the metrology location and moving the SPM tip relative to the metrology location.

In accordance with an aspect of the method for determining the composition of the particle removed from the substrate, the particle collector is a collection pocket or collection through-hole includes at least one contaminate collection edge, and the transferring of the particle from the SPM tip to the particle collector includes maneuvering the SPM tip to brush against or drag against the at least one contaminate collection edge. In accordance with one aspect, the maneuvering includes moving the SPM tip towards and then away from the at least one contaminate collection edge. In one aspect, the moving of the SPM tip may include a scraping and/or wiping motion. In accordance with one aspect, the maneuvering includes moving the SPM tip upward past the at least one contaminate collection edge, and the maneuvering further includes moving the SPM tip downward past the at least one contaminate collection edge.

In accordance with one aspect, the maneuvering includes moving the SPM tip upwards and away from a center of the particle collector. In accordance with one aspect, the maneuvering includes moving the SPM downwards and towards a center of the particle collector. In accordance with one aspect, the maneuvering includes moving the SPM tip in a parabolic trajectory. In accordance with one aspect, the maneuvering further includes rotating the SPM tip to enable debris deposited on a different portion of the SPM tip to be transferred from the SPM tip to the particle collector.

According to an aspect of the present disclosure, an article of manufacture comprising non-transient machine-readable media encoding instructions thereon for causing a processor to determine a composition of a particle on a scanning probe microscopy (SPM) is provided. The encoding instructions of the article of manufacture may be used to perform steps of detecting a first sample irradiation with an irradiation detector, the first sample irradiation being in response to a first incident irradiation from an irradiation source; and effecting relative motion between the SPM tip and at least one of the irradiation source and the irradiation detector based on a first signal from the irradiation detector in response to the first sample irradiation.

There has thus been outlined, rather broadly, certain aspects of the invention in order that the detailed description thereof herein may be better understood, and in order that the present contribution to the art may be better appreciated. There are, of course, additional aspects of the invention that will be described below and which will form the subject matter of the claims appended hereto.

In this respect, before explaining the various aspects of the present disclosure in greater detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present disclosure. Therefore, that the claims should be regarded as including such equivalent constructions insofar as they do not depart from the spirit and scope of the present disclosure.

DETAILED DESCRIPTION

Figure 1A:
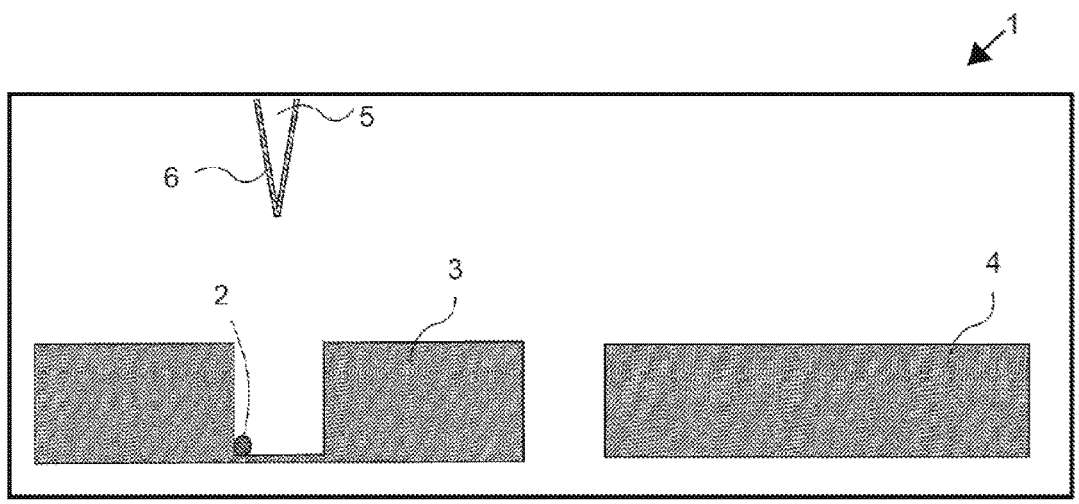
FIGS. 1A to 1C illustrate cross-sectional views of a portion of a debris removal device during a sequence of surface interactions in accordance with aspects of the present disclosure.

The inventive aspects will now be described with reference to the drawing figures, in which like reference numerals refer to like parts throughout.

Figure 1B:
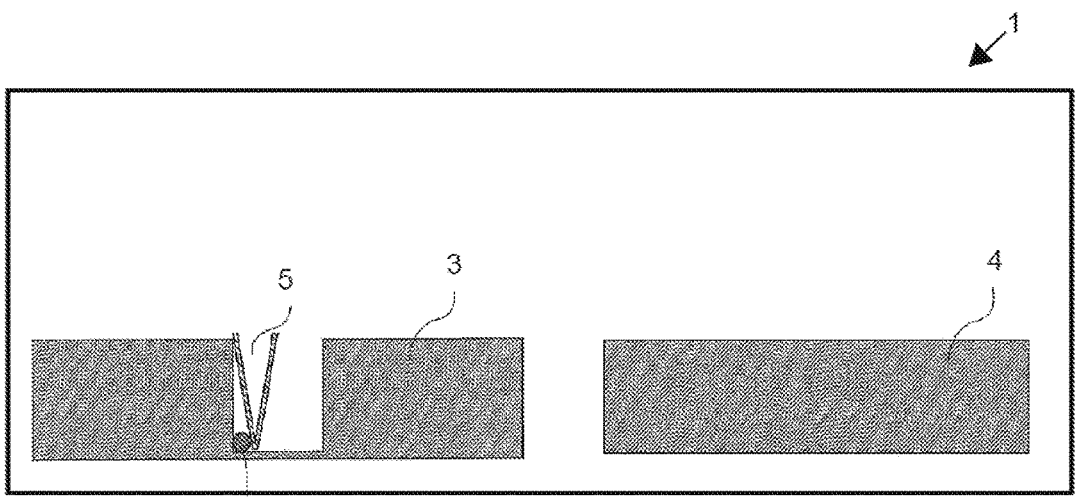
Figure 1C:
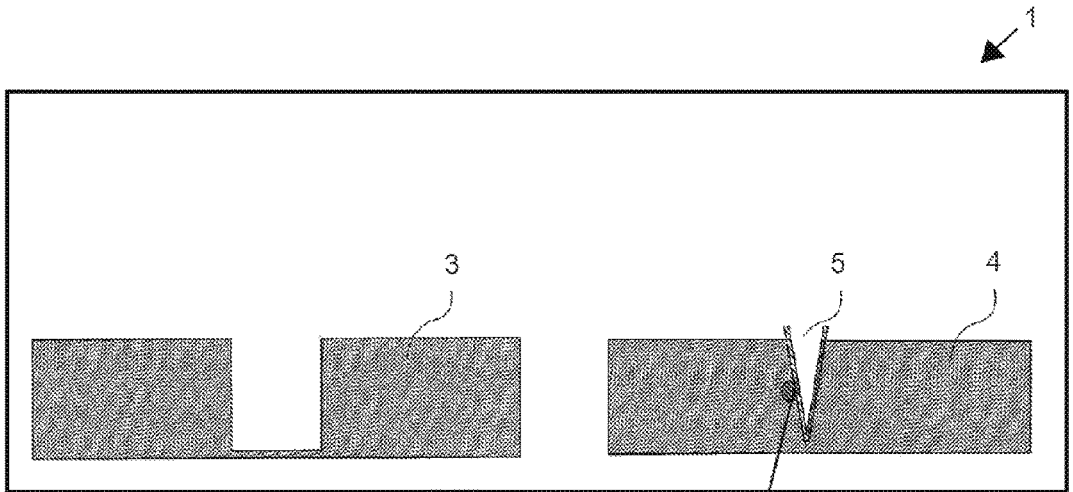

With reference to FIGS. 1A, 1B, 1C, 2, 3, 4, and 5, an exemplary device for removing particles from a substrate and transferring it to a patch will now be described. FIGS. 1A to 1C illustrate cross-sectional views of a portion of a debris removal device 1 during a sequence of surface interactions in accordance with aspects of the present disclosure. A potential sequence of surface interactions that could selectively adhere a particle 2 from a and then relocate it to a soft patch 4 is shown in figures (moving from left to right). In FIG. 1A, a particle 2 contaminates a (relatively) high surface energy substrate 3 which decreases its surface energy and increases the entropy in the whole system. Next in FIG. 1B, a tip 5 with a diffusively mobile low surface energy coating is then driven to coat the (once again relatively) higher surface energy substrate 3 and particle 2, debonding them. Subsequently, the depletion of the low surface energy material may have slightly increased the surface energy of the tip 5 (closer to its normal, uncoated value) so that there is an energy gradient to adhere the now de-bonded particle 2 to a surface of the tip 6 (additionally, materials such a fluorocarbons typically have good cohesion). These interactions should also increase the entropy of the system especially if the tip surface 6 is cleaner than the substrate. Finally, in FIG. 1C, the particle 2 is mechanically lodged into the soft patch material 4 and this mechanical action also recoats the tip surface 6 with the low surface energy material which should both decrease the energy and increase the entropy of the system.

Figure 2:
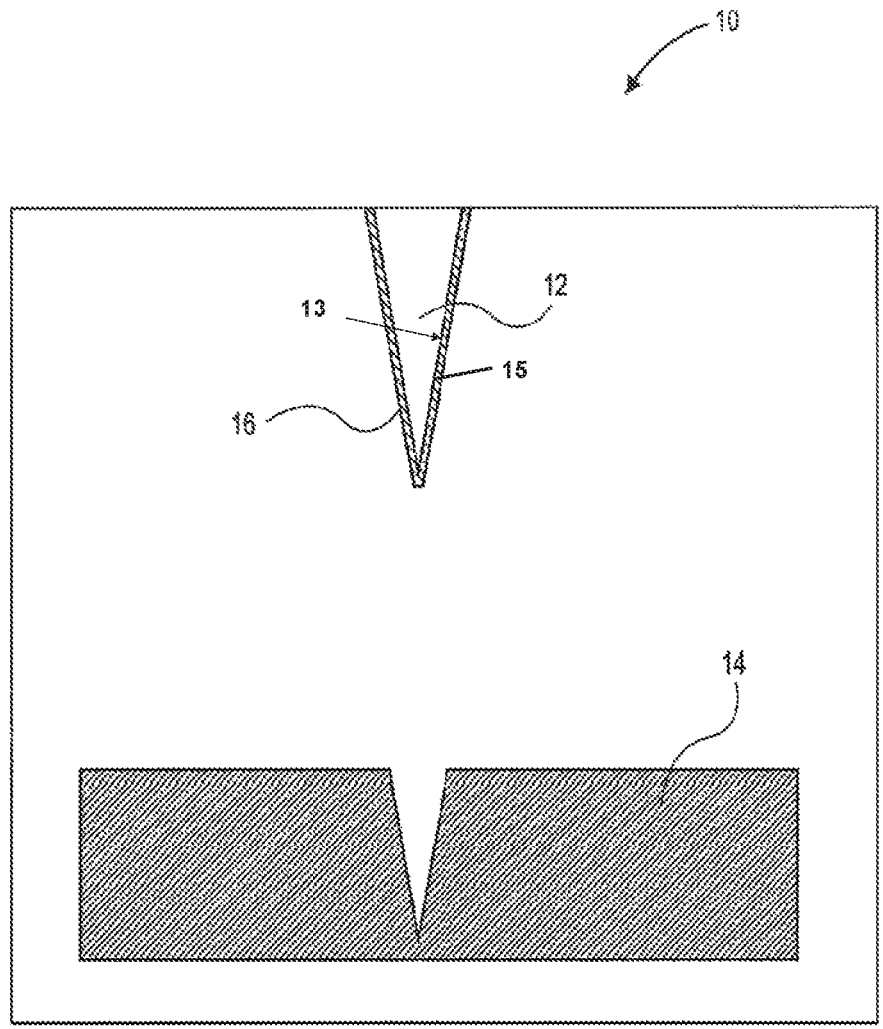
FIG. 2 illustrates a cross-sectional view of a portion of a debris removal device in accordance with aspects of the present disclosure.

FIG. 2 illustrates a cross-sectional view of a portion of a debris removal device 10 according to an embodiment of the present disclosure. The device 10 includes a nanometer-scaled tip 12 positioned adjacent to a patch or reservoir 14 of low surface energy material. The low surface energy material in the reservoir may be solid, liquid, semi-liquid or semi-solid.

Formed on the tip 12 is a coating 16. Before forming the coating 16, tip 12 may be pre-coated or otherwise surface treated to modify the surface energy of the tip 12 (e.g., to modify the capillary, wetting, and/or surface tension effects). When properly selected, the coating 16 allows the tip 12 to remain sharper for a longer period of time than an uncoated tip. For example, a PTFE-coated diamond tip can have a longer operating life than an uncoated diamond tip.

According to certain aspects of the present disclosure, the coating 16 may include the same low surface energy material found in the patch or reservoir of low energy material 14. Also, according to certain aspects of the present disclosure, the tip 12 may be in direct contact with the patch or reservoir of low energy material 14 and the coating 16 may be formed (or replenished) on the surface of tip 12 by rubbing or contacting the tip 12 against the patch or reservoir of low energy material 14. Furthermore, rubbing the tip 12 against the patch or reservoir of low energy material and/or scratching the pad 14 may enhance surface diffusion of the low surface energy material over the surface of tip 12.

According to certain aspects of the present disclosure, the coating 16 and the patch or reservoir of low energy material 14 may both be made from, or at least may include, chlorinated and fluorinated carbon-containing molecules such as Polytetrafluoroethylene (PTFE) or other similar materials such as Fluorinated ethylene propylene (FEP). According to other aspects of the present disclosure, an intermediate layer 15 of metallic material, oxide, metal oxide, or some other high surface energy material may be disposed between the surface of tip 12 and the low-surface energy material coating 16. Some representative examples of the intermediate layer may include, but is not limited to, cesium (Cs), iridium (Ir), and their oxides (as well as chlorides, fluorides, etc.). These two exemplary elemental metals are relatively soft metals with low and high surface energies respectively, and thus they represent the optimization of a surface energy gradient optimal for a given contaminate, substrate, and surrounding environment. Additionally or alternatively, the surface of tip 12 may be roughened or doped. The high surface energy material or tip treatment typically acts to bind the low-surface energy material coating 16 to the tip 12 more strongly. Since the shape of the tip also influences localized surface energy density variations (i.e., nanoscale sharpness will greatly increase surface energy density right at the apex), the shape of the tip 12 may also be modified to provide increased selective adhesion of particles to the tip. Roughening a tip surface 13 of the tip 12 may also provide greater adhesion due to the increase in surface area of contact with the particle and the number of potential binding sites (dA). The tip surface 13 may also be treated (possibly by chemical or plasma processes) so that the tip surface 13 contains highly unstable and chemically active dangling bonds that can react with a particle or some intermediary coating to increase adhesion. The tip surface 13 may also be coated with a high surface area material like high density carbon (HDC) or diamond like carbon (DLC) to increase the surface area of the tip 12 interacting with a particle.

A high-surface energy pre-treatment is used without a low-surface energy coating 16 according to certain aspects of the present disclosure. In such aspects, the particles 20 discussed below may be embedded in some other soft targets (e.g., Au, Al) using similar methods to those discussed herein, or the tip 12 may be a consumable. Also, other physical and/or environmental parameters may be modified (e.g., temperature, pressure, chemistry, humidity) to enhance tip treatment and/or particle pick-up/drop-off as will be appreciated by one skilled in the art in view of the present disclosure.

Figure 3:
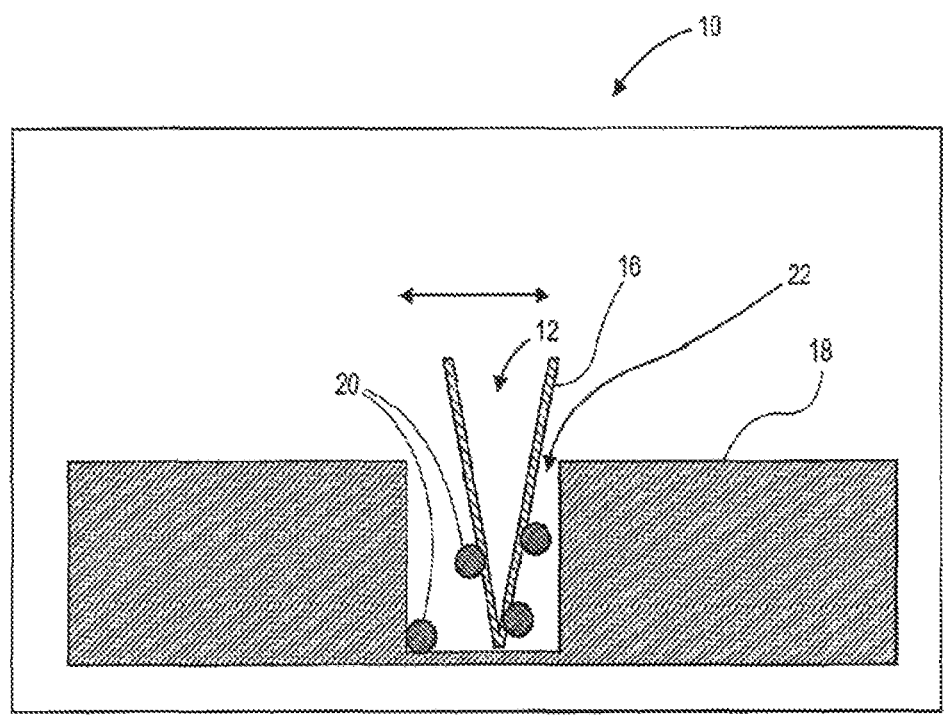
FIG. 3 illustrates a cross-sectional view of another portion of the debris removal device illustrated in FIG. 2.

According to certain aspects of the present disclosure, all of the components illustrated in FIGS. 2 and 3 are included in an AFM. In some such configurations, the patch or reservoir of low energy material 14 is substantially flat and is attached to a stage that supports the substrate 18. Also, according to certain aspects of the present disclosure, the patch or reservoir of low energy material 14 is removable from the stage and may easily be replaced or easily refillable. For example, the patch or reservoir of low energy material 14 may be affixed to the AFM with an easily releasable clamp or magnetic mount (not illustrated).

FIG. 3 illustrates a cross-sectional view of another portion of the debris removal device 10 illustrated in FIG. 2. Illustrated in FIG. 3 is a substrate 18 that may typically be positioned adjacent to the patch or reservoir of low energy material 14 illustrated in FIG. 2. Also illustrated in FIG. 3 is a plurality of particles 20 that may present in a trench 22 that is formed on the surface of the substrate 18. The particles 20 are typically attached to the surfaces of the trench 22 via Van der Waals short-range forces. In FIG. 3, the tip 12 may be moved and positioned adjacent to the substrate 18 to physically attach the particles 20 to the tip 12. In order to reach the bottom of the trench 22, the tip 12 as illustrated in FIGS. 2 and 3 may be a high aspect ratio tip. Although a trench 22 is illustrated in FIG. 3, the particles 20 may be attached to or found on other structures to be cleaned.

Figure 4:
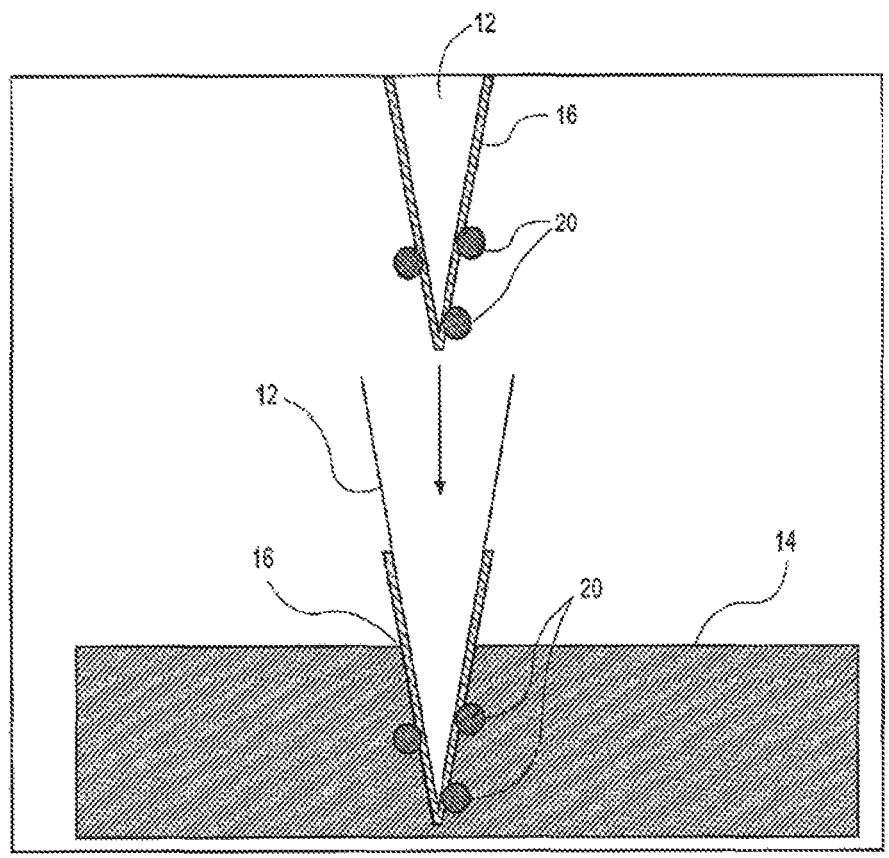
FIG. 4 illustrates a cross-sectional view of the portion of the debris removal device illustrated in FIG. 2, wherein particles are being imbedded in the patch or reservoir of low energy material.
Figure 5:
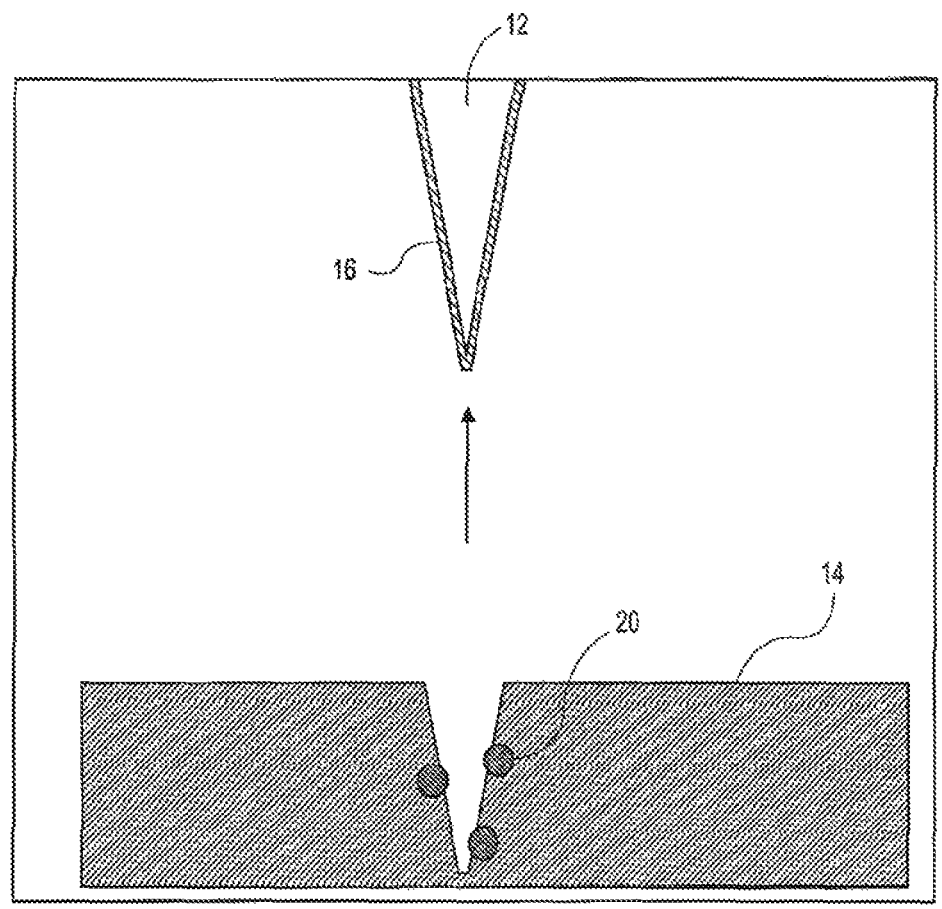
FIG. 5 illustrates a cross-sectional view of the portion of the debris removal device illustrated in FIG. 4, wherein the tip is no longer in contact with the patch or reservoir of low energy material.

FIG. 4 illustrates a cross-sectional view of the portion of the debris removal device 10 illustrated in FIG. 2, wherein the particles 20 may be transferred from the tip 12 and may be imbedded in the patch or reservoir of low energy material 14 by extending the tip 12 into or against a surface of the patch or reservoir of low energy material 14. Subsequently, as shown in the cross-sectional view of FIG. 5, the tip 12 may be retracted such that the tip 12 is no longer in contact with the patch or reservoir of low energy material 14. As the tip 12 is retracted or withdrawn from the patch or reservoir of low energy material 14, the particles 20 previously on the tip 12 remain with the patch or reservoir of low energy material 14.

According to certain aspects of the present disclosure, the device 10 illustrated in FIGS. 2-5 may be utilized to implement a method of debris removal. It should be noted that certain aspects of the present disclosure may be used in conjunction with other particle cleaning processes, either prior or pursuant to the method discussed herein. Further it should be noted that the terms particle, debris, or contaminate may be used interchangeable to describe anything foreign to the substrate surface. It should also be noted that, although only one tip 12 is discussed and shown in the figures, a plurality of tips may be used simultaneously to remove particles from multiple structures at the same time. Additionally, a plurality of tips could be used in the methods discussed herein in parallel and at the same time.

The debris method mentioned above may include positioning the tip 12 adjacent to one or more of the particles 20 (i.e., the pieces of debris) illustrated as being on the substrate 18 in FIG. 3. The method may further include physically adhering (as opposed to electrostatically adhering) the particles 20 to the tip 12 as also illustrated in FIG. 3 as well as some possible repetitive motion of the tip 12 when in contact with the particle(s) 20 and surrounding surfaces. Following the physical adherence of the particles 20 to the tip 12, the method may include removing the particles 20 from the substrate 18 by moving and/or withdrawing the tip 12 away from the substrate 18, and moving the tip 12 with the particles 20 to the patch or reservoir of low energy material 14, as illustrated in FIG. 4.

According to certain aspects of the present disclosure, the method may include forming the coating 16 on at least a portion of the tip 12. In certain aspects of the present disclosure, the coating 16 may comprise a coating material that has a lower surface energy than a surface energy of the substrate 18. Additionally or alternatively, the coating 16 may comprise a coating material that has higher surface area than the surface area of the particle 20 that is in contact with the substrate 18.

In addition to the above, some aspects of the method may further include moving the tip 12 to at least a second location of the substrate 18 such that the tip 12 is adjacent to other pieces of particles or debris (not illustrated) such that the other pieces of particles or debris are physically attached to the tip 12. The other pieces of particles debris may then be removed from the substrate 18 by moving the tip 12 away from the substrate 18 in a manner analogous to what is shown in FIG. 4.

Once debris (e.g., the particles 20 discussed above) have been removed from the substrate 18, some methods according to the present disclosure may include a step of depositing the piece of debris in a piece of material positioned away from the substrate (e.g., the above-discussed patch or reservoir of low energy material 14).

Because the tip 12 may be used repeatedly to remove large amounts of debris, according to certain aspects of the present disclosure, the method may include replenishing the coating 16 by plunging the tip 12 in the patch or reservoir of low energy material 14. Low surface energy material from the patch or reservoir of low energy material may coat any holes or gaps that may have developed in the coating 16 of the tip 12 over time. This replenishing may involve one or more of moving the tip 12 laterally within the patch or reservoir of low energy material 14 after plunging the tip 12 into the patch or reservoir of low energy material 14, rubbing a surface of the tip 12, or altering a physical parameter (e.g., temperature) of the tip 12 and/or the patch or reservoir of low energy material 14.

It should be noted that certain methods according to the present disclosure may include exposing a small area around a defect or particle to a low surface energy material before a repair in order to reduce the likelihood that the removed material will lump together and strongly adhere again to the substrate after the repair is completed. For example, a defect/particle and an approximately 1-2 micron area around the defect may be pre-coated with PTFE or FEP according to certain aspects of the present disclosure. In such instances, a tip 12 coated or constructed from a low surface energy material (e.g., a PTFE or FEP tip) can be used to apply a very generous amount of the low surface energy material to a repair area even when other repair tools (laser, e-beam) are being utilized. In addition to the coating 16 on the tip 12, a portion or an entirety of the tip 12 may comprise a low energy material such as, but not limited to, chlorinated and fluorinated carbon-containing molecules. Examples of such materials may include PTFE or FEP. Additionally or alternatively, other materials such as metals and their compounds may be used. Some representative examples include Cs, Ir, and their oxides (as well as chlorides, fluorides, etc.). These two exemplary elemental metals are relatively soft metals with low and high surface energies respectively, and thus they represent the optimization of a surface energy gradient optimal for a given contaminate, substrate, and surrounding environment. Additionally or alternatively, other carbon based compounds may be used. Some representative examples include HDC or DLC.

According to certain aspects of the present disclosure, the method includes using the patch or reservoir of low energy material 14 to push the particles away from an apex of the tip 12 and toward an AFM cantilever arm (not illustrated) that is supporting the tip 12, above the apex. Such pushing up of the particles 20 may free up space near the apex of the tip 12 physically adhere more particles 20.

According to certain aspects of the present disclosure, the tip 12 is used to remove nanomachining debris from high aspect ratio structures such as, for example, the trench 22 of the substrate 18, by alternately, dipping, inserting, and/or indenting the tip 12 into a pallet of soft material which may be found in the patch or reservoir of low energy material 14. In select aspects, the soft material of the patch or reservoir of low energy material 14 may have a doughy or malleable consistency. This soft material may generally have a greater adherence to the tip 12 and/or debris material (e.g., in the particles 20) than to itself. The soft material may also be selected to have polar properties to electrostatically attract the nanomachining debris particles 20 to the tip 12. For example, the patch or reservoir of low energy material 14 may comprise a mobile surfactant.

In addition to the above, according to certain aspects of the present disclosure, the tip 12 may include one or more dielectric surfaces (i.e., electrically insulated surfaces). These surfaces may be rubbed on a similarly dielectric surface in certain environmental conditions (e.g., low humidity) to facilitate particle pick-up due to electrostatic surface charging. Also, according to certain aspects of the present disclosure, the coating 16 may attract particles by some other short-range mechanism, which may include, but is not limited to, hydrogen bonding, chemical reaction, enhanced surface diffusion.

Figure 6:
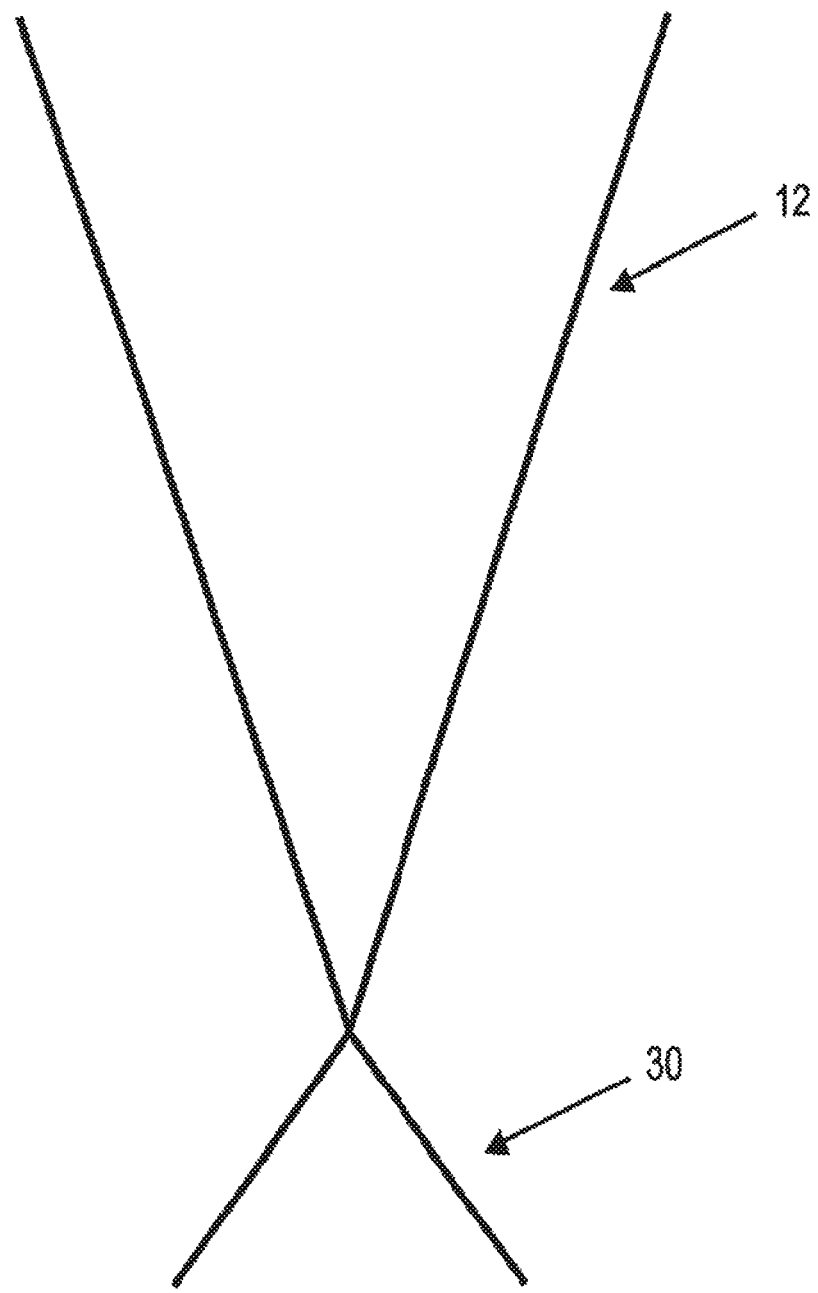
FIG. 6 illustrates a cross-sectional view of a tip with bristles or fibrils in accordance with aspects of the present disclosure.

With reference to FIGS. 6-11, exemplary aspects of the debris removal tip will now be described. Any tip that is strong and stiff enough to penetrate (i.e., indent) the soft pallet material of the patch or reservoir of low energy material 14 may be used. Hence, very high aspect tip geometries (greater than 1:1) are within the scope of the present disclosure. Once the tip is stiff enough to penetrate the soft (possibly adhesive) material, high aspect ratio tips that are strong and flexible are generally selected over tips that are weaker and/or less flexible. Hence, according to certain aspects of the present disclosure, the tip can be rubbed into the sides and corners of the repair trench 22 of the substrate 18 without damaging or altering the trench 22 or the substrate 18. A rough macro-scale analogy of this operation is a stiff bristle being moved inside a deep inner diameter. It should also be noted that, according to certain aspects of the present disclosure, the tip 12 may comprise a plurality of rigid or stiff nanofibrils bristles, as will be described in greater detail below. In one aspect as shown in FIG. 6, each bristle of the plurality of rigid or stiff nanofibrils bristles 30 may extended linearly from the tip 12. In one aspect, the plurality of rigid or stiff nanofibrils bristles 30 may be formed with carbon nanotubes, metal whiskers, etc. The tip 12 may additionally or alternatively comprise a plurality of flexible or wrap nanofibrils, as will be described in greater detail below. The plurality of flexible or wrap nanofibrils may be formed on the tip 12 using polymer materials, for example. Other materials and structures are of course contemplated.

According to certain aspects of the present disclosure, the detection of whether or not one or more particles have been picked up may be performed by employing a noncontact AFM scan of the region of interest (ROI) to detect particles. The tip 12 may then be retracted from the substrate 18 without rescanning until after treatment at the target. However, overall mass of debris material picked up by the tip 12 may also be monitored by relative shifts in the tip's resonant frequency. In addition, other dynamics may be used for the same function.

Instead of indenting in a soft material to remove particles 20 as discussed above and as illustrated in FIG. 5, the tip 12 may also be vectored into the patch or reservoir of low energy material 14 to remove the particles 20. As such, if the tip inadvertently picks up a particle 20, the particle 20 can be removed by doing another repair. Particularly when a different material is used for depositing the particles 20 by vectoring, then a soft metal such as a gold foil may be used.

In addition to the above, an ultra-violet (UV)-light-curable material, or similarly some other material susceptible to a chemically nonreversible reaction, may be used to coat the tip 12 and to form the coating 16. Before the UV cure, the material picks up particles 20 from the substrate 18. Once the tip 12 is removed from the substrate 18, the tip 12 may be exposed to a UV source where the material's properties would be changed to make the particles 20 less adherent to the tip 12 and more adherent to the material in the patch or reservoir of low energy material 14, where the particles 20 may subsequently be removed from the tip 12 and deposited with the patch or reservoir of low energy material 14. Other nonreversible process which further enhances, or enables, the selectivity of particle pick up and removal are of course contemplated.

Certain aspects of the present disclosure provide a variety of advantages. For example, certain aspects of the present disclosure allow for active removal of debris from high aspect trench structures using very high aspect AFM tip geometries (greater than 1:1). Also, certain aspects of the present disclosure may be implemented relatively easily by attaching a low surface energy or soft material pallet to an AFM, along with using a very high aspect tip and making relatively minor adjustments to the software repair sequences currently used by AFM operators. In addition, according to certain aspects of the present disclosure, a novel nanomachining tool may be implemented that could be used (like nano-tweezers) to selectively remove particles from the surface of a mask which could not be cleaned by any other method. This may be combined with a more traditional repair where the debris would first be dislodged from the surface with an uncoated tip, then picked up with a coated tip.

Generally, it should be noted that, although a low surface energy material is used in the local clean methods discussed above, other possible variations are also within the scope of the present disclosure. Typically, these variations create a surface energy gradient (i.e., a Gibbs free energy gradient) that attracts the particle 20 to the tip 12 and may be subsequently reversed by some other treatment to release the particles 20 from the tip 12.

Figure 7A:
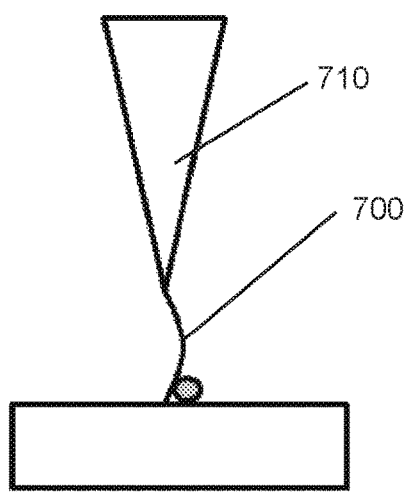
FIGS. 7A and 7B illustrates the general differences between a stiff fibril and a wrap fibril in accordance with aspects of the present disclosure.
Figure 7B:
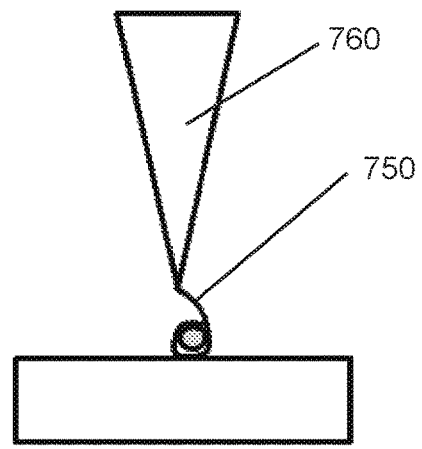

One aspect of the present disclosure involves the attachment of at least one nanofibril to the working end of an AFM tip to provide enhanced capability in high aspect structures while also allowing for less mechanically aggressive process to the underlying substrate. These fibrils can be, according to their mechanical properties and application towards nanoparticle cleaning, classified under two different labels, "stiff" fibrils, and "wrap" fibrils. To understand the differences, FIGS. 7A and 7B illustrate differences between these 2 types of fibrils, the stiff fibril 700 attached to a tip 710 and the wrap fibril 750 attached to a tip 760. Additionally, we must first understand the two critical processes required in BitClean particle cleaning: Dislodgement of the Nanoparticle, Bonding and Extraction of the Nanoparticle from the Contaminated Surface. With these most critical steps defined, the functional differences between the two different fibrils are given as follows.

With reference to FIG. 7A, the stiff fibril 700 relies more on the mechanical action, and mechanical strength, of the fibril itself to dislodge the nanoparticle. Thus, it also relies on the shear and bending strength and moduli of elasticity to accomplish the dislodgement successfully without breaking. This means there are very few materials which could exceed, or even meet, the strength and stiffness (typically referred to as its hardness) of single crystal diamond. Among these are carbon nanotubes and graphene, since both use the carbon-carbon sp3 hybrid orbital interatomic bonds (one of the strongest known) that are also found in diamond. Other contemplated materials include certain phases of boron-containing chemistries which possess properties that could possibly exceed the mechanical strength and stiffness of diamond so these materials could also be used. In general, many materials (including diamond) can become intrinsically stronger and stiffer as their dimensionality is reduced (with stiffness decreasing as the structure approaches atomic scales and its shape is determined by thermal diffusive behaviors). This is a material phenomenon that was first observed in nanocrystalline metals but has also been confirmed in molecular simulation and some experiment to also occur with single crystal nanopillars. One leading hypothesis for this behavior leads into the defect diffusion mechanism of plastic deformation. At larger scales, these crystal defects (vacancies, dislocations, etc.) diffuse and interact in bulk-dominated kinetics. It is believed that at smaller scales (all things being equal such as material and temperature), these defect movements become dominated by surface-diffusion kinetics which are much higher than in the bulk of the crystal. When considered within a material-continuum approximation, this greater surface diffusion rate translates into plastic deformation (also referred to as yield), and even failure, of materials at lower stress levels. For example, with Ti single-crystal nanopillars, the yield stress has been shown to increase with decreasing cross-section width up to a range around 8 to 14 nm (depending, in part, to the direction of the stress and the crystallographic orientation of the nanopillar), below this range, the behavior undergoes an inflection point where the yield stress actually decreases with decreasing cross-section width.

Figures 8A, 8B, 8C:
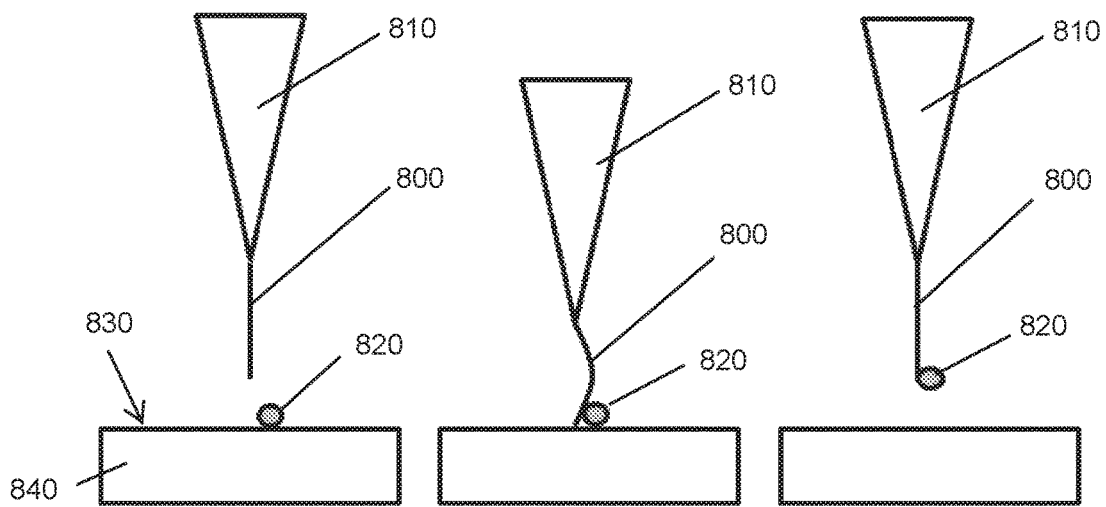
FIGS. 8A to 8C illustrate a process of dislodging and removing a nanoparticle from a target substrate using a single stiff fibril in accordance with aspects of the present disclosure.

FIGS. 8A to 8C illustrate an exemplary process of dislodging and removing a nanoparticle from a target substrate using a single stiff fibril 800 attached at or near the apex of an AFM tip 810. The tip 810 approaches the surface and scans using the same principles as an AFM scan without the stiff fibril. It will be appreciated by one skilled in the art that different operational parameters may be applied in view of the single stiff fibril 800 attached to the apex of the tip 810. Once the particle is located, the tip 810 is moved towards a surface 830 and the stiff fibril 800 is elastically deformed, as generally shown in FIG. 8B. In one aspect, the deformation of the stiff fibril 800 may be compressive, shear, bending, tensile or a combination thereof and can also be used to mechanically dislodge the nanoparticle 820 from the surface 830. Once the nanoparticle 820 is dislodged, the surface energy and area differences between the stiff fibril 800, substrate 840 and nanoparticle 820 surfaces govern whether the nanoparticle 820 adheres to the stiff fibril 800 when it is subsequently extracted from the substrate surface 830.

Figures 9A, 9B, 9C:
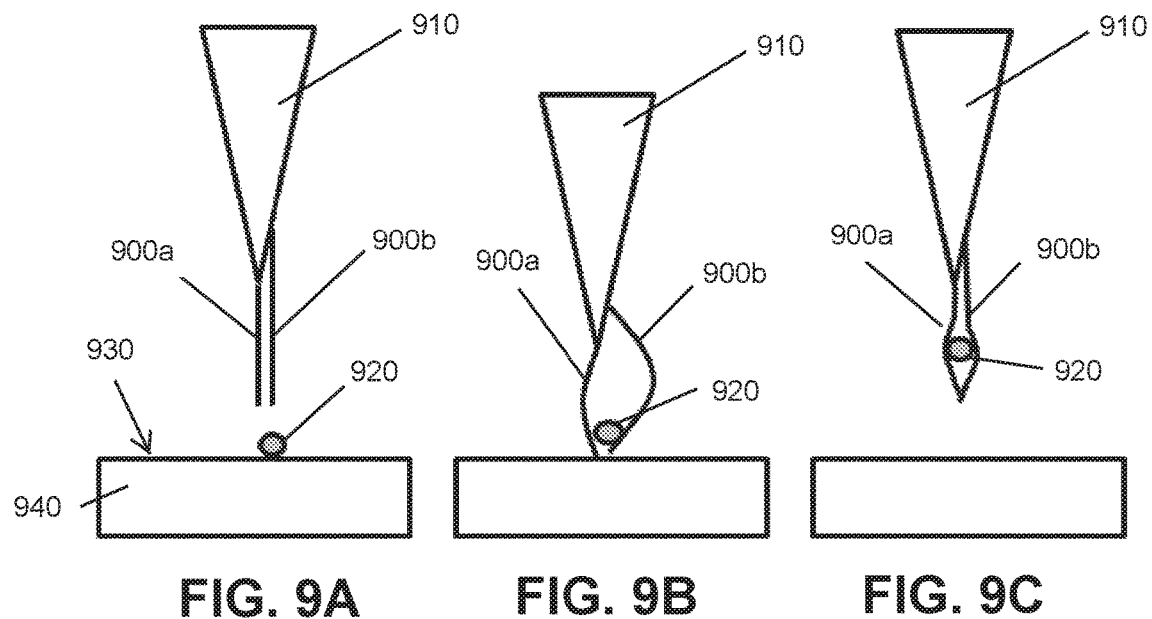
FIGS. 9A to 9C illustrate a process of dislodging and removing a nanoparticle from a target substrate using a plurality of stiff fibrils in accordance with aspects of the present disclosure.

An exception to this, unique to the stiff fibril nanoparticle clean process, is when two or more stiff fibrils are strongly attached to the tip surface at a distance less than the nanoparticle diameter (but not less than the elastic deformation limit for the stiff fibrils as determined by their shear and bending moduli and length to width ratio), as illustrated in FIGS. 9A to 9C. In accordance with aspects where two or more stiff fibrils 900a, 900b are attached to the tip 910 at a distance less than the nanoparticle diameter, the sequence is very similar to the single stiff fibril as discussed above with reference to FIGS. 8A to 8C. The differences starting in the observation that there are more strained or deformed stiff fibrils 900a, 900b around the nanoparticle 920 thus increasing the probability that one or more stiff fibrils 900a, 900b will impact the nanoparticle 920 in just the way (force and angle of applied force) needed to dislodge a nanoparticle 920 for a given cleaning scenario, as generally shown in FIG. 9B. Following the dislodgement step, the multi-fibril tip 910 may have more potential surface area for the particle 920 to adhere (i.e., wet) to. As the tip 910 is retracted from the substrate, as generally shown in FIG. 9C, another difference emerges if the length and spacing of the fibrils are within the correct range. The nanoparticle 920 with this setup has the possibility of becoming mechanically trapped within the spaces between the stiff nanofibrils 900a, 900b, which may result in greater adhesion to the multi-fibril 900a, 900b and a greater probably of extracting the nanoparticle 920 from the substrate surface 930. Similarly, if it is desired to deposit the nanoparticle 920 on another surface, the tip 910 may be re-approached to a surface and the stiff fibrils 900a, 900b again stressed to relax their mechanical entrapment of the nanoparticle 920 thus increasing the probability the nanoparticle 920 will be deposited at the desired surface location. As previously stated, this assumes that the length and spacing of the fibrils 900a, 900b are within the correct range, on the first order model, these ranges include a fibril spacing less than the minimum width of the nanoparticle 920 (assuming a strong nanoparticle that will not crumble), but large enough that the fibrils 900a, 900b will not be bent beyond their shear and bending strength limit (also determined by the relative length of the fibrils and assuming the adhesion strength of the fibril attachment is not less than this limit), as will be appreciated by those skilled in the art in view of the present disclosure. In select aspects, the two or more stiff fibrils may have different and unequal lengths.

To define what a stiff fibril is (as opposed to a wrap fibril), one must be able to define the anisotropic spring constants (related to the effective shear and bending moduli) for a specific material and nano-structure. Since this is very difficult to do in practice, it is assumed for our purposes here that these properties are roughly proportional to the tensile (a.k.a. Young's) elastic modulus and strength. The tensile modulus is a possible measure of the stiffness of a material within the stress range where it exhibits elastic (i.e., spring-like) mechanical properties. It is given as the stress divided by the strain, thus yielding units the same as stress (since stain is defined as deformation ratio of final versus initial dimension). Although it does not specifically define stiffness, tensile strength is also important since the fibril must be able to apply sufficient force to dislodge a nanoparticle without breaking-off itself and creating an additional contamination to the substrate surface. Strength is also given in units of stress (Pascals). For diamond, the intrinsic tensile modulus is on the order of 1.22 terra-Pascals (TPa) with a tensile strength ranging from 8.7 to 16.5 giga-Pascals (GPa) and provides here our general reference measure for stiffness and strength (approaching within the value for tungsten of 0.5 TPa for tensile elastic modulus, or exceeding these values). Since carbon nanotubes are, by their very nature, not intrinsic entities their tensile moduli are specific to the individual molecule and its properties (e.g., Single-walled or Multi-Walled, respectively SWNT or MWNT, chirality, etc.). For SWNT's, their tensile elastic modulus can range from 1 to 5 TPa with its tensile strength ranging from 13 to 53 GPa. For comparison with another class of materials in this range, $B_xN_y$ (boron nitride compounds of various stoichiometry) has a tensile elastic modulus which ranges from 0.4 to 0.9 TPa. For the purpose of distinguishing and defining the boundary between a wrap fibril from a stiff fibril, the standard mechanical material property most relevant and applicable is the yield stress. A stiff fibril is defined here as any material with a yield stress greater than or equal to 0.5 GPa (1 GPa=$1\times10^9$ N/m$^2$). Thus, by elimination, any material with a yield stress less than 0.5 GPa would be considered a wrap fibril. It should be noted that, especially at nanoscales, many materials can exhibit anisotropic mechanical properties so it is important that the yield stress is specified for shear stresses (or equivalent bending stresses) transverse to the fibril's major (i.e., longest) dimension.

A wrap fibril, in contrast to a stiff fibril, will have much lower spring constants (specified here as elastic tensile moduli) with sufficiently high (comparable) tensile strength. In the case of the wrap fibrils, due to the differences in how it is applied, the tensile strength is directly related to its performance since a tensile force is applied to both dislodge and extract the nanoparticle from the substrate surface. However, it should be noted, that most mechanical properties quoted in the literature are for the bulk material which should, in principle, be almost completely unrelated to the tensile properties for mono-molecular fibrils (or nano-scale fibrils approaching mono-molecular scales). For example, PTFE, is typically quoted to have very low tensile elastic modulus and strength in the bulk material (0.5 GPa and maybe <<20 MPa respectively), but since the molecule's backbone is comprised of carbon-carbon sp-hybrid orbital chemical bonds, its mono-molecular tensile strength should be more comparable to diamond than many other materials, C-nanotubes, and graphene (all of which contain the same kind of chemical bonds). Since the bulk material mechanical properties is more related to the action of single-molecule strands interacting with their neighbors, it should be more comparable to both the cohesive and mono-molecular bending and shear moduli. Since these types of materials (polymers) exemplify the mechanical properties associated with plastic deformation, their molecules are expected to deform according to more diffusive-thermal behaviors which exhibit high flexibility. If the macroscopic allegory for the stiff fibril is a sliver of glass, the comparable allegory for the wrap fibril would be thin carbon fibers (the latter can appear highly flexible at macro scales with high tensile strength).

Figures 10A, 10B, 10C:
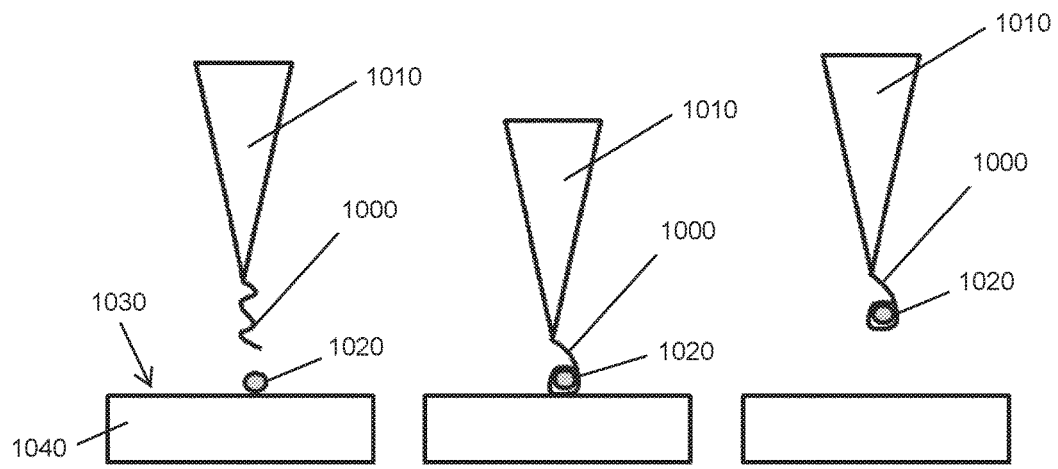
FIGS. 10A to 10C illustrate a process of removing a nanoparticle from a target substrate using a single wrap fibril in accordance with aspects of the present disclosure.

FIGS. 10A to 10C show a nanoparticle cleaning sequence using a wrap (flexible) nanofibril 1000 attached to an AFM tip 1010 near or at the apex, in accordance with an aspect of the present disclosure. Since there is no compression stress required to deform the wrap-type fibril 1000, the tip 1010 is brought into close proximity to the surface 1030 in order to bring the fibril 1000 into close enough proximity to the nanoparticle surface for short range surface energy forces to allow for the fibril 1000 to adhere to it. Since the relative surface energies of the fibril 1000, nanoparticle 1020, and substrate surfaces 1030 are targeted so that the fibril would preferentially adhere to the nanoparticle surface, once the fibril 1000 is brought into contact with enough slack given the fibril length, only time and applied agitation energies (possibly mechanical and/or thermal) are required to allow the fibril 1000 to wrap around the particle 1020. It is possible that mechanical energies (whether by the tip 1010 with the fibrils 1000 attached, or another tip in a prior processing pass) from a more rigid tip could be applied to initially dislodge the particle 1120. Once the fibril 1000 is sufficiently wrapped-around the nanoparticle 1020, as generally shown in FIG. 10B, the tip 1010 is then extracted from the substrate surface 1030. During this phase, if the adhesion of the fibrils 1000 to the nanoparticle 1020 (enhanced the more it is wrapped and entangled around the nanoparticle), the tensile strength of the fibril 1000, and its adhesion to the AFM tip 1010 are all greater than the adhesion of the nanoparticle 1020 to the substrate 1040, then the nanoparticle 1020 will be extracted from the substrate 1040 with the tip 1010, as generally shown in FIG. 10C.

Figures 11A, 11B, 11C, 11D:
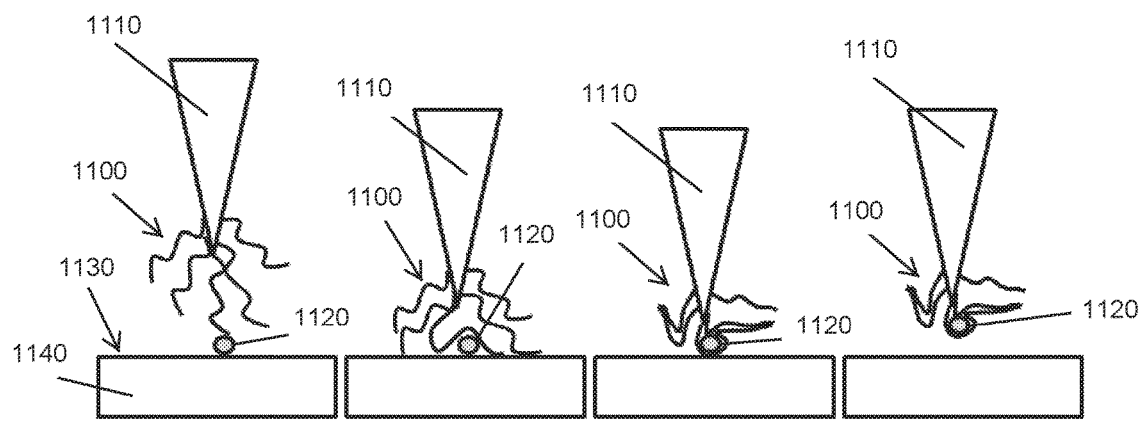
FIGS. 11A to 11D illustrate e process of removing a nanoparticle from a target substrate using a plurality of wrap fibrils in accordance with aspects of the present disclosure.

Some examples of possible materials that may be used to make wrap nano (or molecular) scale fibrils include: RNA/DNA, Actin, amyloid nanostructures, and Ionomers. RNA (ribonucleic acid) and DNA (deoxyribonucleic acid) are described together since they represent similar chemistries, preparation, and handling processes. Recently, significant progress has been made with the technology known colloquially as, "DNA-Origami", which allows for the precise chemical engineering of how DNA molecules link together. It is believed that similar processes, applied to these or similar chemistries, could allow for long polymer chain molecules to detach and link-together on queue. Given the most common process, specific DNA sequences would be chemically produced, or obtained commercially from well-known single-stranded viral DNA sequences, and a properly chemically-functionalized (such as is done in Chemical Force Microscopy practices) AFM tip 1110 is immersed in the aqueous solution, or placed in AFM-contact to a surface, containing the DNA sequences so that the latter bind as designed. The tip 1110 may then be functionalized for particle removal from a substrate surface 1130, as shown in FIGS. 11A to 11D. Moving from left to right in the figures, the functionalized tip 1110 may be moved or actuated to approach near (closer than the length of the DNA strands 1100) the particle 1120 and substrate surfaces 1130, as shown in FIG. 11A. A higher temperature may be applied (possibly ~90° C.) with an activating chemistry (either helper DNA strands, also available commercially, or some other ionic activator such as a magnesium salt) while the tip 1110 is near the dislodged particle 1120 as shown in FIG. 11B. The environment may then cooled (possibly to ~20° C.) allowing the targeted sequences in the strands 1100 to link up as shown in FIG. 11C (the linking strands 1100 are at the opposite free ends of the molecules). Once the DNA coating 1100 has solidified to the point where the nanoparticle 1120 is securely attached, the tip 1110 may then be extracted from the substrate surface 1130 as shown in FIG. 11D. At these small scales, it is possible to describe this bonding between the nanoparticle and the tip to be mechanical, however if the particle is on the molecular scale, it could also be described as a steric bond. Steric effects may be created by atomic repulsion at close enough proximity. If an atom or molecule is surrounded by atoms in all possible diffusion directions, it will be effectively trapped and unable to chemically of physically interact with any other atoms or molecules in its environment. RNA can similarly be manipulated as will be appreciated by those skilled in the art in view of the present disclosure The next possible wrap nano-fibril candidate is a family of similar globular multi-function proteins that forms filaments in eukaryotic cells, one of which is known as actin. Actin is used inside cells for scaffolding, anchoring, mechanical supports, and binding, which would indicate it is a highly adaptable and sufficiently strong protein filament. It would be applied and used in methods very similar to the DNA-origami related process discussed above. Experiments indicate that this protein can be crystalized to a molecule of dimensions of 6.7×4.0×3.7 nm.

Research into the mechanisms in which certain marine organisms (barnacles, algae, marine flatworms, etc.) can strongly bond to a large range of substrate materials biomimetically (or directly) provides another wrap fibril candidate. These marine organisms secrete a substance, commonly referred to by the acronym DOPA (3, 4-dihydroxyphenylalanine), which bonds to these substrate surfaces with functional amyloid nanostructures. The adhesive properties of amyloid molecules are due to β-strands that are oriented perpendicular to the fibril axis and connected through a dense hydrogen-bonding network. This network results in supramolecular β-sheets that often extend continuously over thousands of molecular units. Fibrillar nanostructures like this have several advantages including: underwater adhesion, tolerance to environmental deterioration, self-healing from self-polymerization, and large fibril surface areas. As previously discussed, large fibril surface areas enhance adhesion by increasing the contact area in the adhesive plaques of barnacles. Amyloid nanostructures also have possible mechanical advantages such as cohesive strength associated with the generic amyloid intermolecular β-sheet structure and adhesive strength related to adhesive residues external to the amyloid core. These properties make amyloid structures a basis for a promising new generation of bio-inspired adhesives for a wide range of applications. Advances in the use of molecular self-assembly have allowed for the creation of synthetic amyloid and amyloid-analogue adhesives for nanotechnological applications although a fully rational design has not yet been demonstrated experimentally, in part, due to limits in understanding of the underlying biological design principles.

The final example of a wrap fibril material is a class of polymers known as ionomers. In brief, these are long thermoplastic polymer molecules that strongly bind at targeted ionic charged sites along the molecular chain. A common example of an ionomer chemistry is poly(ethylene-co-methacrylic acid). According to one aspect of the present disclosure, the ionomer may be functionalized to the surface of a scanning thermal probe. The process for cleaning a nanoparticle would then be very similar to that shown for the DNA-origami process discussed above except that an aqueous environment would not necessarily be required especially when used with the scanning thermal probe. An ionomer functionalization coating may also be paired with an ionic surfactant for preferential conjugate bonding within an aqueous (or similar solvent) environment. It should be mentioned that these examples (especially DNA/RNA and actin) are highly biocompatible for removal and manipulation of nano-particulate entities inside living structures such as cells.

For example, one variation that may be used includes using a high surface energy tip coating. Another variation includes pretreating the particles with a low surface energy material to debond the particles and then contacting the particles with a high surface energy tip coating (sometimes on a different tip). Still another variation includes making use of a chemical energy gradient that corresponds to a chemical reaction occurring between a tip surface coating and the particle surface to bond the two. This may either be performed until a tip is exhausted or reversed with some other treatment.

According to still other aspects of the present disclosure, adhesives or sticky coatings are used in combination with one or more of the above-listed factors. Also, the surface roughness or small scale (e.g., nanometer-scale) texture can be engineered to maximize particle clean process efficiency.

In addition to the above, mechanical bonding may be used, typically when the tip 12 includes fibrils that, analogously to a mop, are capable of mechanically entangling the particles 20. The mechanical entanglement, according to certain aspects of the present disclosure, is driven by and/or enhanced by surface energy or chemical changes with contact or environment.

According to still other aspects of the present disclosure, the tip 12 may be coated with molecular tweezers (i.e., molecular clips). These tweezers may comprise noncyclic compounds with open cavities capable of binding guests (e.g., the above-discussed particles 20). The open cavity of the tweezers typically binds guests using non-covalent bonding including hydrogen bonding, metal coordination, hydrophobic forces, van der Waals forces, π-π interactions, and/or electrostatic effects. These tweezers are sometimes analogous to macrocyclic molecular receptors except that the two arms that bind the guest molecules are typically only connected at one end.

In addition to the above, the particles 20 may be removed by the tip using diffusion bonding or Casmir effects. Also, as in the aspects of the present illustrated in FIG. 6, bristles or fibrils 30 can be attached to the end of the tip 12. Whether strategically or randomly placed, these bristles or fibrils 30 can enhance local clean in several ways. For example, an associated increase in surface area may be used for surface (short range) bonding to the particles.

According to some of aspects of the present disclosure, fibrils 30 are engineered to be molecules that selectively (e.g., by either surface or environment) coil around and entangle a particle 20, thus maximizing surface contact. Also, dislodging of the particles 20 occurs according to certain aspects of the present disclosure, typically when stiff bristles 30 are attached to the tip 12. However, fibrils 30 may also entangle a particle 20 and dislodge the particle 20 mechanically by pulling on the particle 20. In contrast, relatively rigid bristles 30 typically allow the tip 12 to extend into hard-to-reach crevices. Then, by impact deformation stress of the bristles 30, by surface-modification of the tip 12 to repel particles 20, or by some combination, the particle 20 is dislodged. In addition, certain aspects of the present disclosure mechanically bond the particles 20 to the tip 12. When fibrils are on the tip 12, entanglement of one or more of either the whole or frayed fibrils may occur. When bristles are on the tip 12, the particle 20 may be wedged between (elastically) stressed bristles.

According to still other aspects of the present disclosure, methods of debris removal include changing the environment to facilitate local clean. For example, gas or liquid media may be introduced or the chemistry and/or physical properties (e.g., pressure, temperature, and humidity) may be changed.

In addition to the components discussed above, certain aspects of the present disclosure include an image recognition system that identifies debris to be removed. As such, an automatic debris-removal device is also within the scope of the present disclosure.

According to certain aspects of the present disclosure, a relatively soft cleaning tip is used to avoid unwanted damage to inside contours, walls, and/or bottom of a complex shape. When appropriate, a stronger force is used to bring the relatively soft tip into much stronger contact with the surface while also increasing the scan speed.

It should also be noted that a tip exposed to and/or coated with a low surface energy material may be used for other purposes besides removing debris (cleaning) of nanometer level structures. For example, such tips can also be used, according to certain aspects of the present disclosure, to periodically lubricate micron level or smaller devices (like MEMS/NEMS) to contain chemical reactions.

This method may be performed in a variety of environments according to the requirements of the application and to further enhance differential adhesion of the particle from the substrate surface to the patch or reservoir of low energy material. These environments may include, but are not limited to, vacuum, shield gasses of various composition and pressure, and fluids of variable composition (including fluids with varying ionic strengths and/or pHs).

Since there are many other factors influencing the Gibbs free energy gradients between the substrate, tip, debris, and soft patch, these other factors may also be manipulated to create a down-hill gradient to move particles from the substrate to the soft patch. One factor is temperature. It would be possible to use a scanning thermal probe in conjunction with temperature of the substrate and soft patch material to create a desired gradient. The fundamental equation for Gibbs free energy indicates that if the debris is successively contacted by surfaces of greater relative temperature (since the T*S term is negative in the equation) may provide a possible driving force of $\Delta G<0$. From the equation for AG of a deformed rod under high temperature, we can also see another factor is stress applied to the tip would potentially increase debris adhesion. This could be accomplished by external hardware (i.e., biomaterial strips with different coefficients of thermal expansion) or by compression or shear with the substrate below the threshold for nanomachining or tip breakage. The deformation of the tip material may also provide a mechanism of mechanical entrapment of the debris especially if it is roughened (or covered in nano-bristles) and/or if it has a high microstructural defect (i.e., void) density at the surface. The final factor that will be discussed will be chemical potential energy. It is possible to modify the chemical state of the tip and/or soft patch surfaces to create preferential chemical reactions to bond the debris material to the tip. These chemical bonds may be covalent or ionic in nature (with the sp3-hybrid orbital covalent bond being the strongest). The debris may be coated with one component of a targeted lock-and-key chemically bonding pair of chemistries. The tip (or another tip) may be coated with the other chemical and brought in contact with the debris surface to bond it to the tip. One non-limiting example of a lock-and-key pair of chemistries is streptavidin and biotin which is often used in Chemical Force Microscopy (CFM) experiments. Another example using an ionic bond would be two surfactant polar molecular chemistries where the exposed polar ends of the molecules on the debris and tip surface are of opposite charge. There are additional related aspects to the surface chemical interaction adhesion mechanisms including depleted solvation and steric-interacting coatings or surfaces. Chemical changes to the tip surface would also allow for targeted changes to its surface energy as well as phase changes (in particular from fluid to solid) that may surround (to maximize surface area dA) and mechanically entrap the debris at the tip surface in order to bond it. These chemical changes (whether to the tip material surface or some intermediary coating) may be catalyzed by external energy sources such as heat (temperature), ultraviolet light, and charged particle beams.

Figure 12:
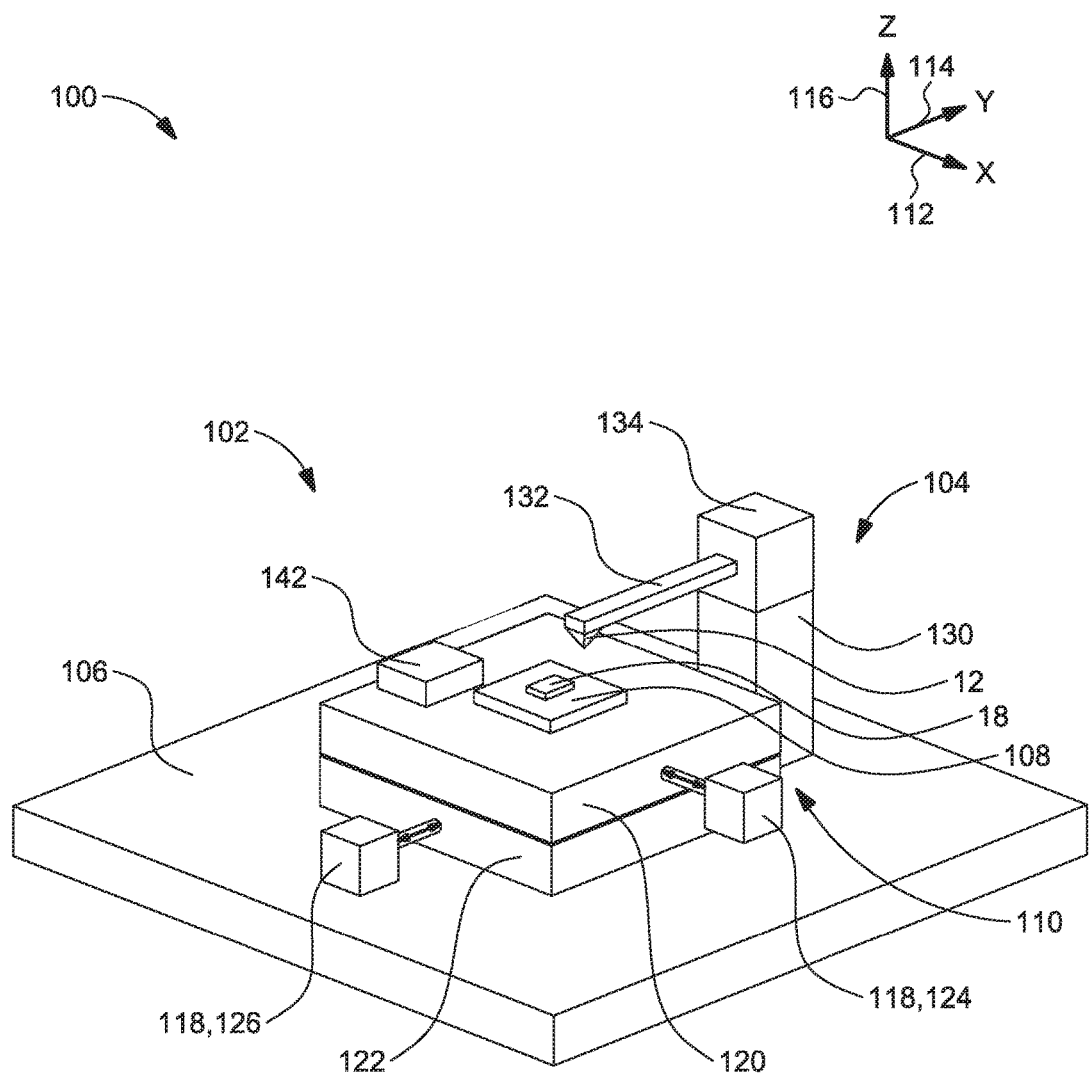
FIG. 12 illustrates a perspective view of a debris collection apparatus including at least one patch in accordance with aspects of the present disclosure.

Turning to FIGS. 12-38, exemplary aspects of debris detection and collection systems will now be discussed. FIG. 12 illustrates a perspective view of a debris collection apparatus 100 for extracting debris 20 from a substrate 18, according to an aspect of the disclosure. The apparatus 100 includes a substrate support assembly 102 and a tip support assembly 104, each being supported by or coupled to a base 106. The base 106 may be a unitary slab, such as a unitary metallic slab, a unitary stone slab, a unitary concrete slab, or any other unitary slab structure known in the art. Alternatively, the base 106 may include a plurality of slabs that are fixed relative to one another. The plurality of slabs may include a metal slab, a stone slab, a concrete slab, combinations thereof, or any other slab assembly known in the art. According to an aspect of the disclosure, the base 106 may be a unitary stone slab, such as a unitary granite slab or a unitary marble slab, for example.

The substrate support assembly 102 may include a fixture 108 configured to support the substrate 18, fix the substrate 18 to the substrate support assembly 102, or both. The substrate support assembly 102 may further include a substrate stage assembly 110 that is configured to move the fixture 108 relative to the base 106. The substrate stage assembly 110 may include one or more motion stages, such as linear translation stages, rotational motion stages, combinations thereof, or any other motion stage known in the art. For example, the substrate stage assembly 110 may be configured to move the fixture 108 relative to the base 106 in translation along an x-direction 112, in translation along a y-direction 114, in translation along a z-direction 116, in rotation about the x-direction 112, in rotation about the y-direction 114, in rotation about the z-direction 116, or combinations thereof. The x-direction 112, the y-direction 114, and the z-direction 116 may be mutually orthogonal to one another, however, it will be appreciated that x-direction 112, the y-direction 114, and the z-direction 116 need not be mutually orthogonal to one another.

The one or more motion stages of the substrate stage assembly 110 may include one or more actuators 118 that are configured to effect a desired relative motion between the fixture 108 and the base 106. For example, the one or more actuators 118 may include a rotational motor coupled to the substrate stage assembly 110 via a threaded rod or a worm gear, a servo motor, a magnetic actuator configured to assert a force on the substrate stage assembly 110 via a magnetic field, a pneumatic or hydraulic piston coupled to the substrate stage assembly 110 via a piston rod, a piezoelectric actuator, or any other motion actuator known in the art. The one or more actuators 118 may be fixed to the base 106.

According to an aspect of the disclosure, the substrate stage assembly 110 may include a first stage 120 and a second stage 122, where the first stage 120 is configured to move the fixture 108 relative to the second stage 122 via a first actuator 124, and the second stage is configured to move the first stage 120 relative to the base via a second actuator 126. The first actuator 124 may be configured to translate the first stage 120 along the x-direction 112, and the second actuator 126 may be configured to translate the second stage 122 along the y-direction 114. However, it will be appreciated that the first stage 120 and the second stage 122 may be configured to move relative to the base 106 in translation along or rotation about other axes to suit other applications.

The tip support assembly 104 may include a tip 12 coupled to a tip stage assembly 130 via a tip cantilever 132. The tip 12 may be a Scanning Probe Microscopy (SPM) tip, such as a tip for an AFM or a Scanning Tunneling Microscopy (STM). It will be appreciated that the tip 12 illustrated in FIG. 12 may embody any of the tip structures or attributes previously discussed herein. Accordingly, the tip stage assembly 130 may be an SPM scanner assembly. The tip stage assembly 130 may be fixed to the base 106, and configured to move the tip 12 relative to the base 106 in translation along the x-direction 112, in translation along the y-direction 114, in translation along the z-direction 116, in rotation about the x-direction 112, in rotation about the y-direction 114, in rotation about the z-direction 116, or combinations thereof.

Similar to the substrate stage assembly 110, the tip stage assembly 130 may include one or more actuators 134 to effect the desired motion of the tip 12 relative to the base 106. According to an aspect of the disclosure, the one or more actuators may include a rotary actuator system operatively coupled to the tip 12 in order to rotate the tip 12 about a first axis. According to an aspect of the disclosure, the one or more actuators 134 may include one or more piezoelectric actuators, however, it will be appreciated that other actuator structures may be used for the one or more actuators 134 to meet the needs of a particular application, without departing from the scope of the present disclosure.

The substrate stage assembly 110 may be configured to effect motions with greater magnitude and lower precision than motions effected by the tip stage assembly 130. Thus, the substrate stage assembly 110 may be tailored to effect coarse relative motion between the fixture 108 and the tip 12, and the tip stage assembly 130 may be tailored to effect finer relative motion between the fixture 108 and the tip 12.

Figure 13:
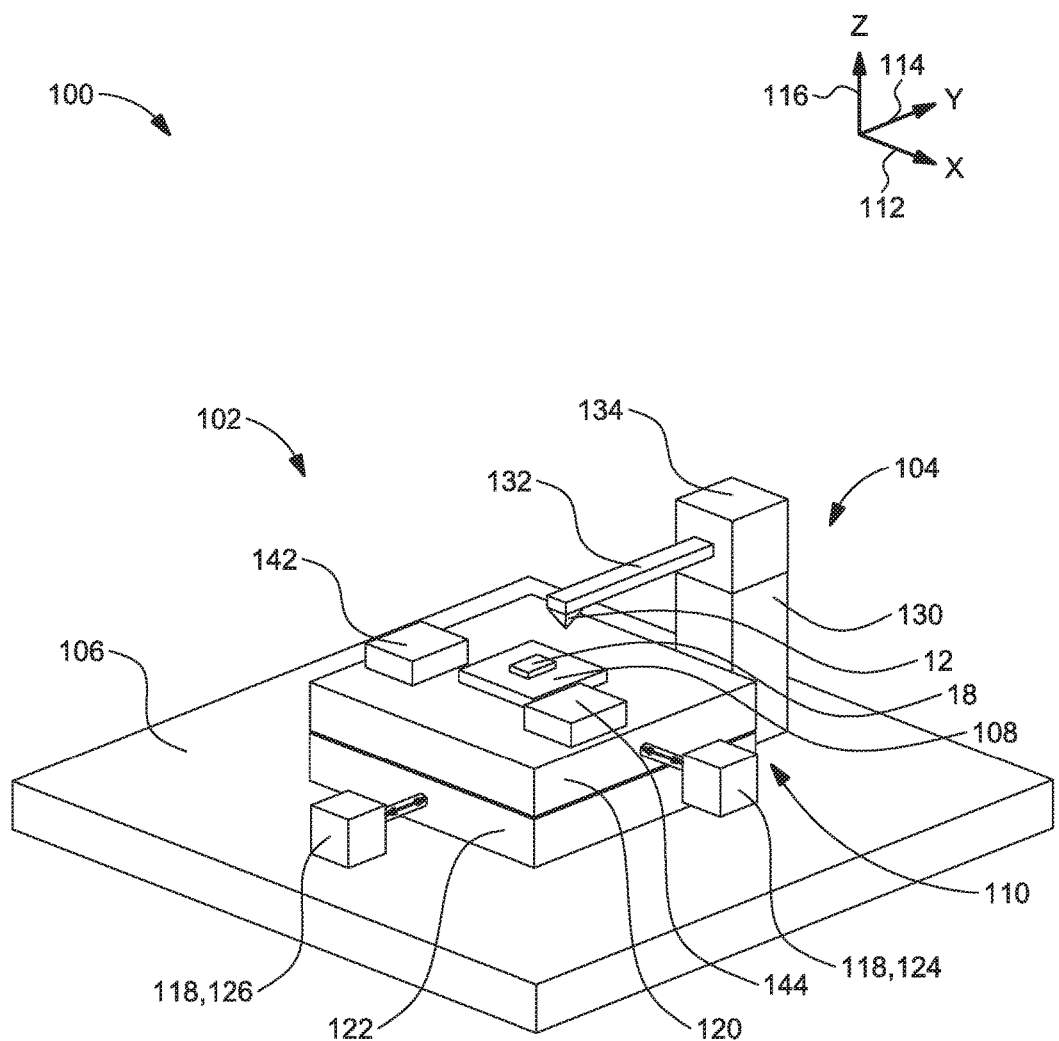
FIG. 13 illustrates a perspective view of a debris collection apparatus including at least two patches in accordance with aspects of the present disclosure.

In accordance with one aspect, the apparatus 100 of FIG. 12 may include a first patch 142 disposed on the substrate support assembly 102, the base 106, or both. In accordance with another aspect, as shown in FIG. 13, the apparatus 100 may include a first patch 142 and a second patch 144 disposed on the substrate support assembly 102, the base 106, or both. The first patch 142, the second patch 144, or both, may embody any of the structures, materials, or attributes of the patch 14 previously discussed. According to an aspect of the disclosure, the second patch 144 may embody structures and materials that are similar or identical to that of the first patch 142, where the second patch 144 is used predominately to receive and hold debris 20 collected from the substrate 18 via the tip 12, and the first patch is used predominately to treat or prepare the tip 12 for subsequent collection of debris 20 from the substrate 18. Alternatively, the second patch 144 may embody structures or materials different from the first patch 142, such that the first patch 142 may be better tailored to treating the tip 12 before collecting debris 20 from the substrate 18, and the second patch 144 may be better tailored to receive and hold debris 20 collected from the substrate 18 and deposited onto the second patch 144 via the tip 12.

In one aspect, the second patch 144 may be configured as a collection pocket or collection through-hole for collecting debris or contaminate from the tip 12, as will be described in further detail with reference to FIGS. 30-37. However, it will be appreciated that either the first patch 142 or the second patch 144 may be used alone to both treat the tip 12 prior to collecting debris 20 from the substrate 18 and to receive and hold debris 20 collected from the substrate 18 using the tip 12. As shown in FIG. 13, the second patch 144 may be disposed or mounted to the first stage 120 opposite of the first patch 142. However, the second patch 144 may be located adjacent to the first patch 142, or may be located on any other location of the first stage 120 or on the debris collection apparatus 100 to promote capture of debris when configured as a collection pocket or collection through-hole.

Figure 14:
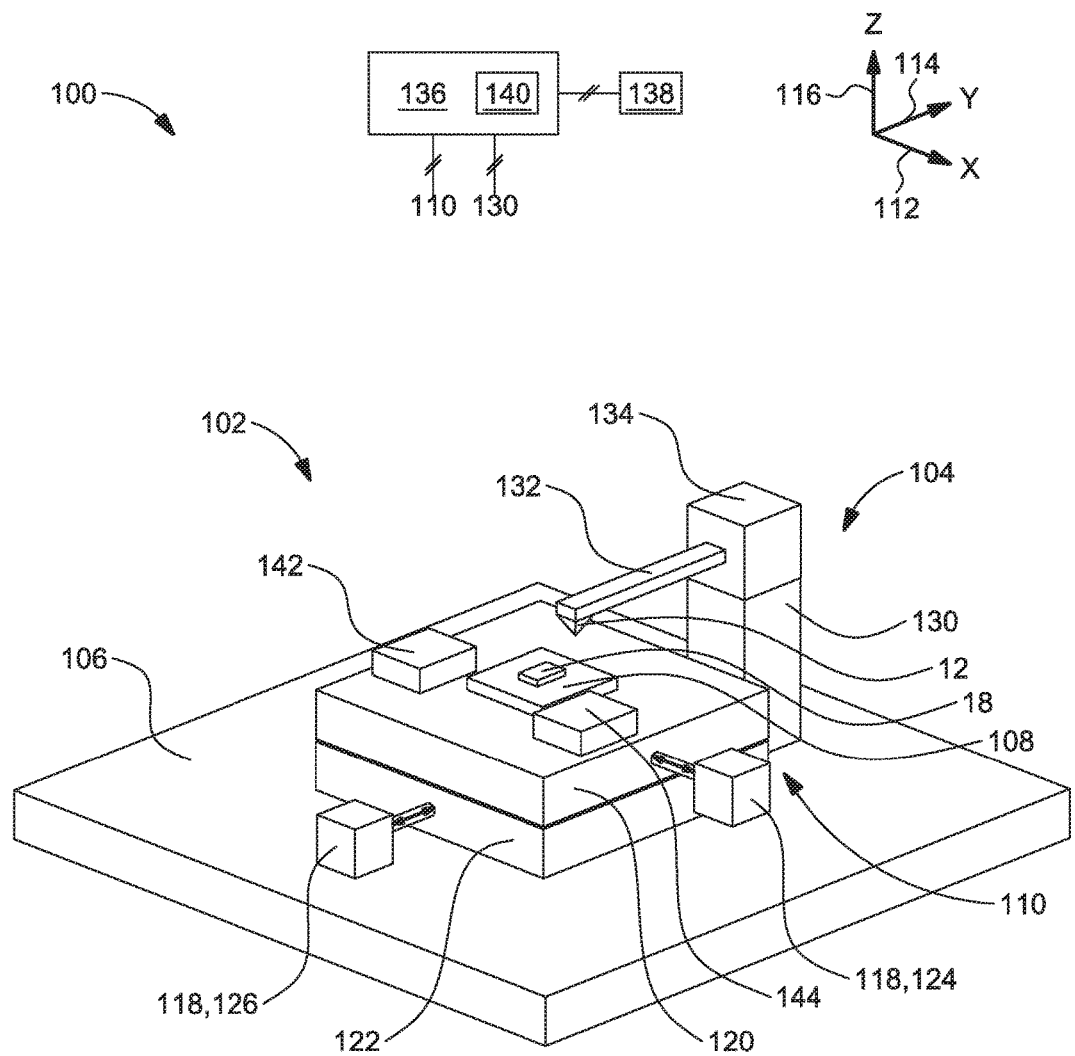
FIG. 14 illustrates a perspective view of a debris collection apparatus including a controller in accordance with aspects of the present disclosure.

In accordance with aspects of the disclosure, as shown in FIG. 14, any or all of the actuators 118 for the substrate stage assembly and the actuators 134 for the tip stage assembly from the debris collection apparatus 100 of FIG. 12 or 13, respectively, may operatively be coupled to a controller 136 for control thereof. Accordingly, the controller 136 may effect relative motion between the fixture 108 and the base 106, and the tip 12 and the base 106 through control of the actuators 118, 134, respectively. In turn, the controller 136 may effect relative motion between the tip 12 and the fixture 108 through control of the actuators 118, 134.

Further, the controller 136 may effect relative motion between the fixture 108 and the base 106 in response to manual user inputs 138, procedures or algorithms pre-programmed into a memory 140 of the controller 136, combinations thereof, or any other control inputs known in the art. It will be appreciated that pre-programmed control algorithms for the controller 136 may include closed-loop algorithms, open-loop algorithms, or both.

Figure 15:
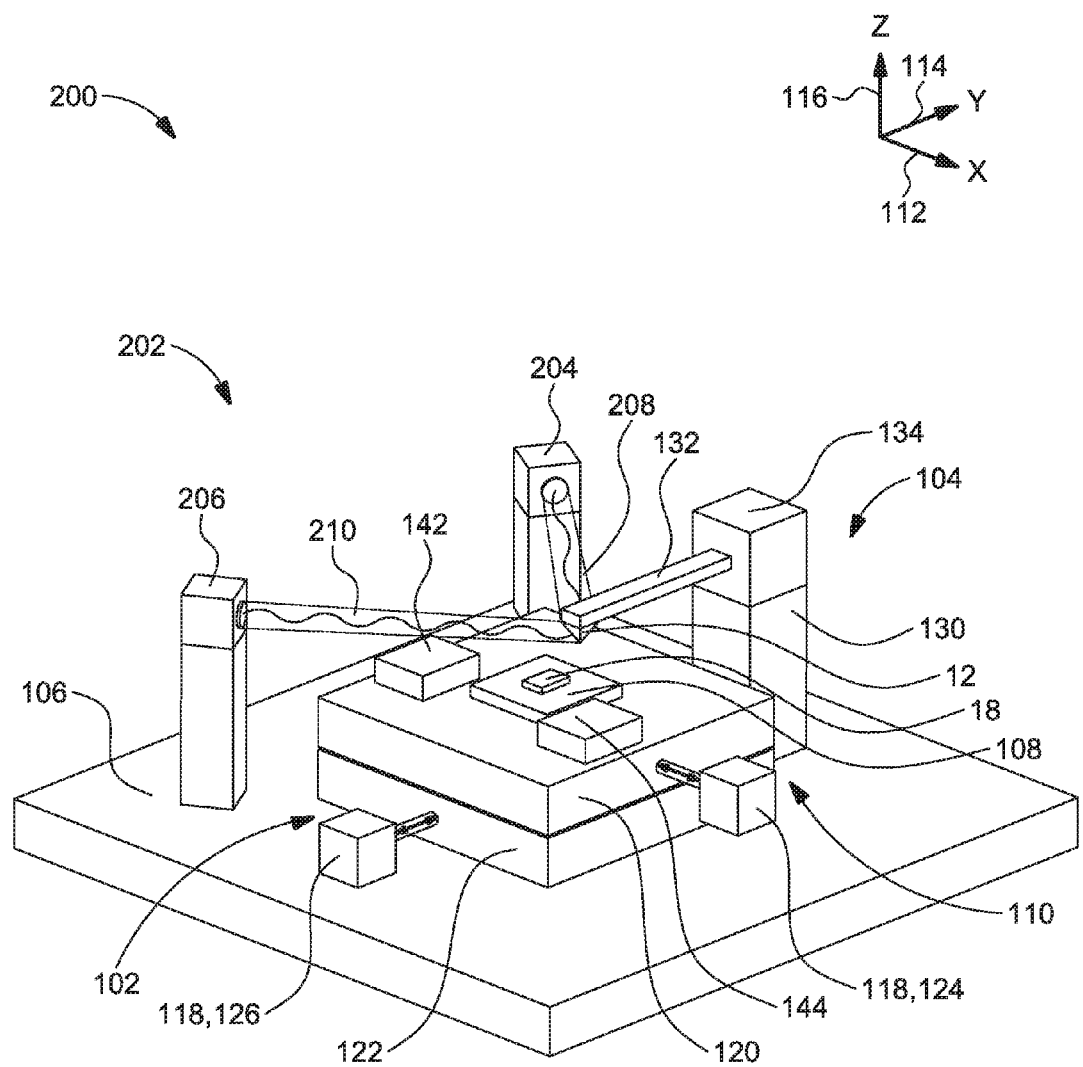
FIG. 15 illustrates a perspective view of a debris collection apparatus including a metrology system in accordance with aspects of the present disclosure.

FIG. 15 illustrates a perspective view of a debris collection and metrology apparatus 200 for extracting debris 10 from a substrate 18 and analyzing properties of the debris 20, according to an aspect of the disclosure. Similar to the debris collection apparatus 100 of FIG. 12, the debris collection and metrology apparatus 200 includes a substrate support assembly 102, a tip support assembly 104, and a base 106. However, the debris collection and metrology apparatus 200 further includes a metrology system 202. In accordance with aspects of the present disclosure, the metrology system 202 may be a nano-scale metrology system.

The metrology system 202 may include an energy source 204 and an energy detector 206. The energy source 204 may be an x-ray source, a visible light source, an infrared light source, an ultraviolet light source, an electron beam source, a laser source, combinations thereof, or any other electromagnetic energy source known in the art. It will be appreciated that visible light sources may include a visible light laser, infrared light sources may include an infrared laser, and ultraviolet light sources may include an ultraviolet laser.

The energy source 204 may be directed towards and trained on the tip 12 such that an incident energy beam 208 generated by the energy source 204 is incident upon the tip 12. At least a portion of the incident energy beam 208 may be reflected, refracted, or absorbed and re-emitted by the tip 12 or debris 20 disposed on the tip 12. According to an aspect of the disclosure, the energy source 204 may be an irradiation source configured and arranged to direct an incident irradiation onto the tip 12, such as an SPM tip, and the energy detector 206 may be an irradiation detector configured and arranged to receive a sample irradiation from the tip 12, the sample radiation being generated as a result of the incident irradiation being applied and reflected, refracted, or absorbed and re-emitted by the tip 12 or debris 20 disposed on the tip 12.

The energy detector 206 may also be directed towards and trained on the tip 12 such that a sample energy beam 210 is incident upon the energy detector 206. The sample energy beam 210 may include contributions from the incident energy beam 208 reflected by the tip 12 or debris 20 disposed on the tip 12, refracted by the tip 12 or debris 20 disposed on the tip 12, absorbed and re-emitted by the tip 12 or debris 20 disposed on the tip 12, combinations thereof, or any other energy beam that may result from an interaction between the incident energy beam 208 and either the tip 12 or debris 20 disposed on the tip 12. Accordingly, the energy detector 206 may be a light detector, such as a photomultiplier tube or a photodiode, for example, an x-ray detector; an electron beam detector; combinations thereof; or any other electromagnetic radiation detector known in the art.

According to an aspect of the disclosure, the energy source 204 includes an electron beam source, and the energy detector 206 includes an x-ray detector. According to another aspect of the disclosure, the energy source 204 includes an x-ray source, and the energy detector 206 includes an electron beam detector. According to another aspect of the disclosure, the energy source 204 includes a light source, including but not limited to, visible light and infrared light.

Figure 16:
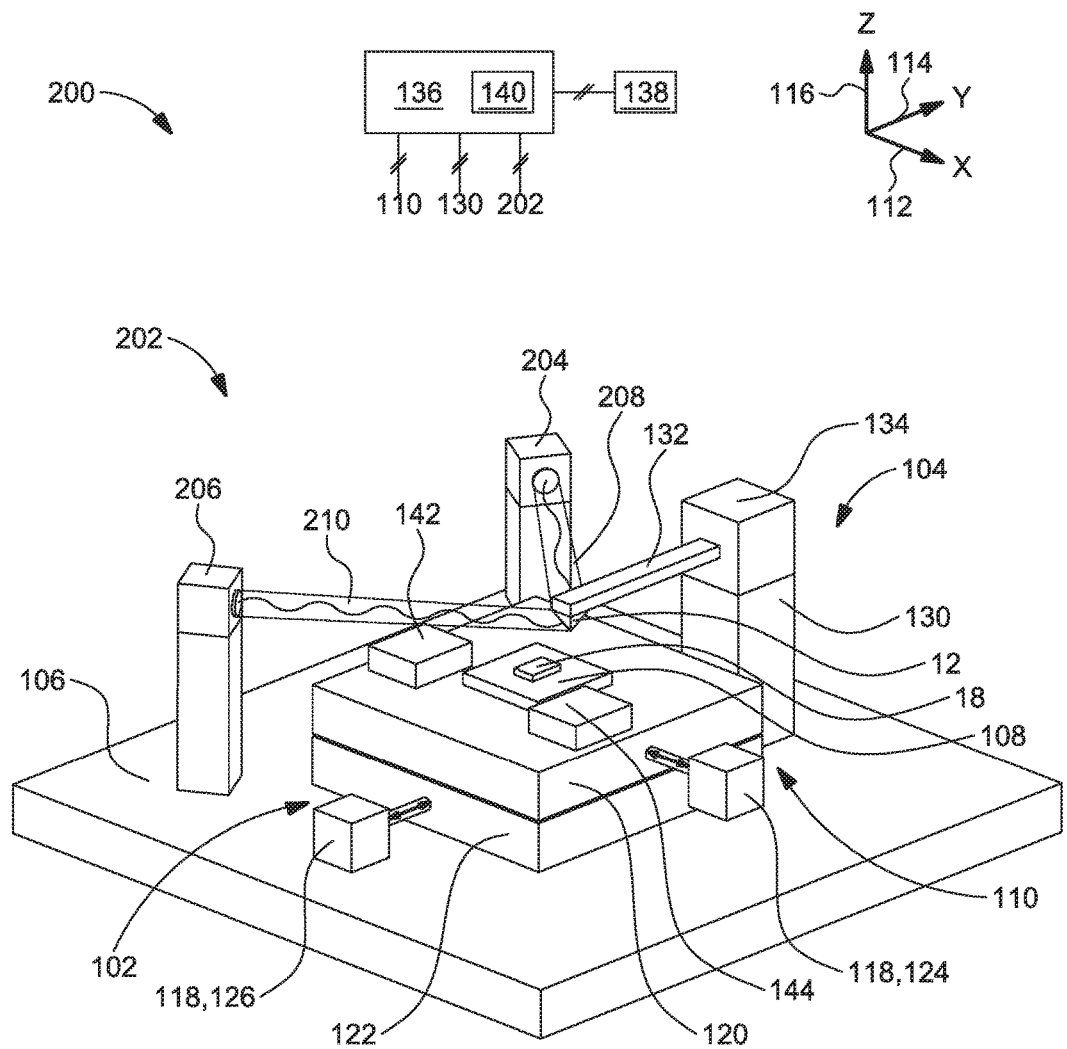
FIG. 16 illustrates a perspective view of a debris collection apparatus including a metrology system and a controller in accordance with aspects of the present disclosure.

The energy detector 206 may be configured to generate an output signal based on an intensity of the sample energy beam 210, a frequency of the sample energy beam 210, combinations thereof, or any other electromagnetic radiation property of the sample energy beam 210 known in the art. Further, in accordance with aspects of the present disclosure, the energy detector 206 may be coupled to the controller 136, as shown in FIG. 16, such that the controller 136 receives the output signal from the energy detector 206 in response to the sample energy beam. Accordingly, as described later herein, the controller 136 may be configured to analyze the output signal from the energy detector 206 in response to the sample energy beam 210 and identify one or more material attributes of the tip 12 or debris 20 disposed on the tip 12. Optionally, the energy source 204 may operatively be coupled to the controller 136 of FIG. 16, such that the controller 136 may control attributes of the incident energy beam 208 that is generated by the energy source 204, such as, but not limited to an intensity of the incident energy beam 208, a frequency of the incident energy beam 208, or both. In one aspect, a direction of the energy source 204, the sample energy beam 210, and/or the energy detector 206 may be adjusted in response to the output signal from the energy detector 206.

According to an aspect of the disclosure, the controller 136 may operatively be coupled to an actuator system including the one or more actuators 134 and the energy detector 206, the controller 136 being configured to receive a first signal based on a first response of the energy detector to a sample irradiation, such as the sample energy beam 210, and being configured to effect relative motion between the tip 12 and the at least one energy detector 206 via the one or more actuators 134 based on the first signal. In one aspect, the controller 136 may be configured to generate a first frequency domain spectrum of the sample irradiation based on a first response of the irradiation detector to a sample irradiation, and generate a second frequency domain spectrum by subtracting a background frequency domain spectrum from the first frequency domain spectrum. In response to the second frequency domain spectrum, the controller 136 may effect relative motion between the tip 12 and at least one of the energy source 204 and the energy detector 206 via the one or more actuators 134. In one aspect, the controller 136 may further be configured to generate the background frequency domain based on a response of the energy detector 206 on the tip 12 when the tip 12 is free of or substantially free of contamination. In one aspect, the controller 136 may be configured to receive a second signal based on a second response of the energy detector 206 to the sample irradiation, and the controller 136 may be configured to effect relative motion between the tip 12 and at least one of the energy detector 206 and the energy source 204 via the one or more actuators 134 based on a difference between the first signal and the second signal. In one aspect, the controller 136 is configured to effect a magnitude of relative motion between the tip 12 and at least one of the energy detector 206 and the energy source 204 based on a difference between the first signal and the second signal.

Figure 17A:
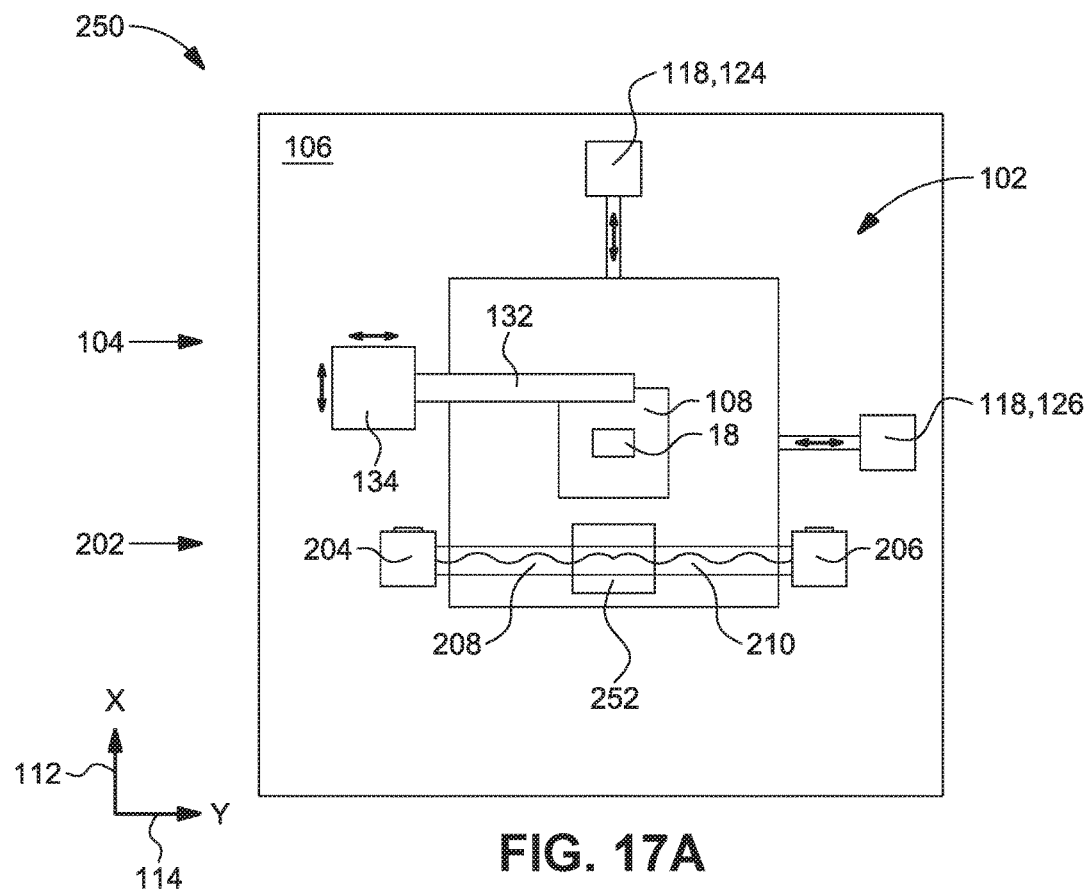
FIGS. 17A and 17B illustrate a top and a side view, respectively, of a debris collection apparatus including a metrology apparatus in accordance with aspects of the present disclosure.
Figure 17B:
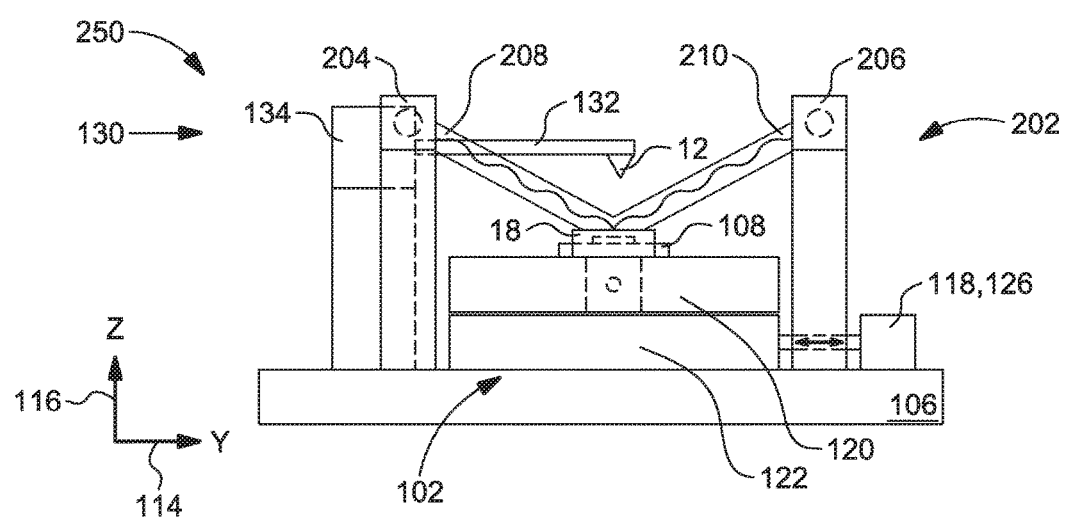
Figure 18A:
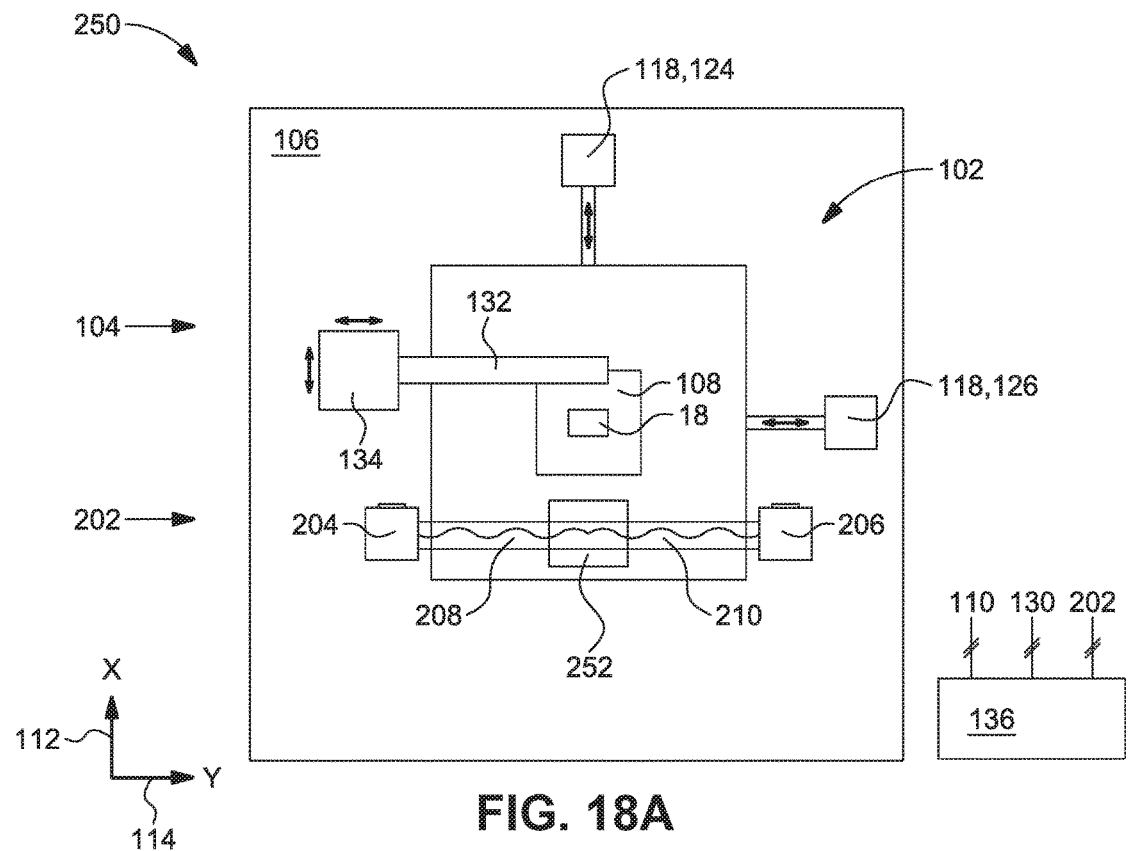
FIGS. 18A and 18B illustrate a top and a side view, respectively, of a debris collection apparatus including a metrology apparatus and a controller in accordance with aspects of the present disclosure.
Figure 18B:
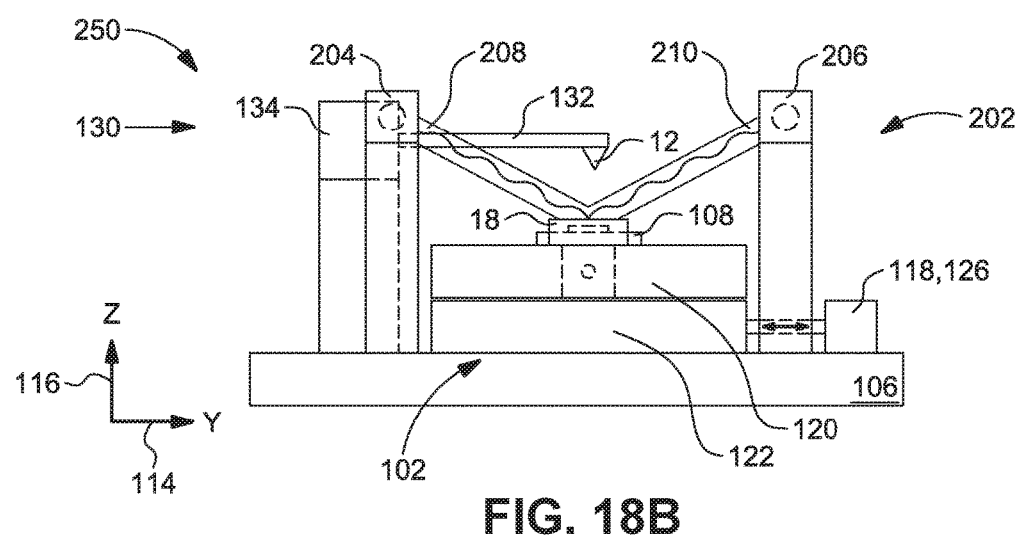

Referring now to FIGS. 17A, 17B, 18A and 18B, it will be appreciated that FIGS. 17A and 18A illustrate top views of a debris collection and metrology apparatus 250, and FIGS. 17B and 18B illustrate side views of a debris collection and metrology apparatus 250, according to aspects of the disclosure. Similar to the debris collection and metrology apparatus 200, illustrated in FIGS. 15 and 16, respectively, the debris collection and metrology apparatus 250 may include a substrate support assembly 102, a tip support assembly 104, a base 106, and a metrology system 202. However, in the debris collection and metrology apparatus 250, the energy source 204 and the energy detector 206 may each be directed towards and trained on a patch 252 instead of the tip 12.

The patch 252 may embody any of the structures or attributes of the first patch 142 or the second patch 144 previously discussed, or the patch 252 may include or be configured as a collection pocket or collection through-hole for collecting debris or contaminate from the tip 12, as will be described in further detail with reference to FIGS. 30-37. Accordingly, the debris collection and metrology apparatus 250 may be configured to analyze a material property of the patch 252, debris 20 disposed on the patch 252, or combinations thereof, using the metrology system 202.

Actuation and/or adjustment of the substrate stage assembly 110, the tip stage assembly 130, or both, is capable of effecting at least three procedures using the debris collection and metrology apparatus 250. During a first procedure, actuation and/or movement of the substrate stage assembly 110, the tip assembly 130, or both, effects contact between the tip 12 and a substrate 18 disposed on the fixture 108, such that debris 20 is transferred from the substrate 18 to the tip 12. During a second procedure, actuation and/or movement of the substrate stage assembly 110, the tip stage assembly 130, or both, effects contact between the tip 12 and the patch 252 to transfer debris 20 from the tip 12 to the patch 252. During a third procedure, actuation and/or movement of the substrate stage assembly 110 directs and trains each of the energy source 204 and the energy detector 206 onto the patch 252, such that an incident energy beam 208 from the energy source 204 is incident upon the patch 252, and a sample energy beam 210 emanating from the patch 252 is incident up on the energy detector 206.

As shown in FIGS. 18A and 18B, the energy detector 206 may be coupled to the controller 136, such that the controller 136 receives the output signal from the energy detector 206 in response to the sample energy beam. Accordingly, as described later herein, the controller 136 may be configured to analyze the output signal from the energy detector 206 in response to the sample energy beam 210 and identify one or more material attributes of the patch 252 or debris 20 disposed on the patch 252. Optionally, the energy source 204 may operatively be coupled to the controller 136 of FIGS. 18A and 18B, such that the controller 136 may control attributes of the incident energy beam 208 that is generated by the energy source 204, such as, but not limited to an intensity of the incident energy beam 208, a frequency of the incident energy beam 208, or both. In one aspect, a direction of the energy source 204, the sample energy beam 210, and/or the energy detector 206 may be adjusted in response to the output signal from the energy detector 206.

Figure 19A:
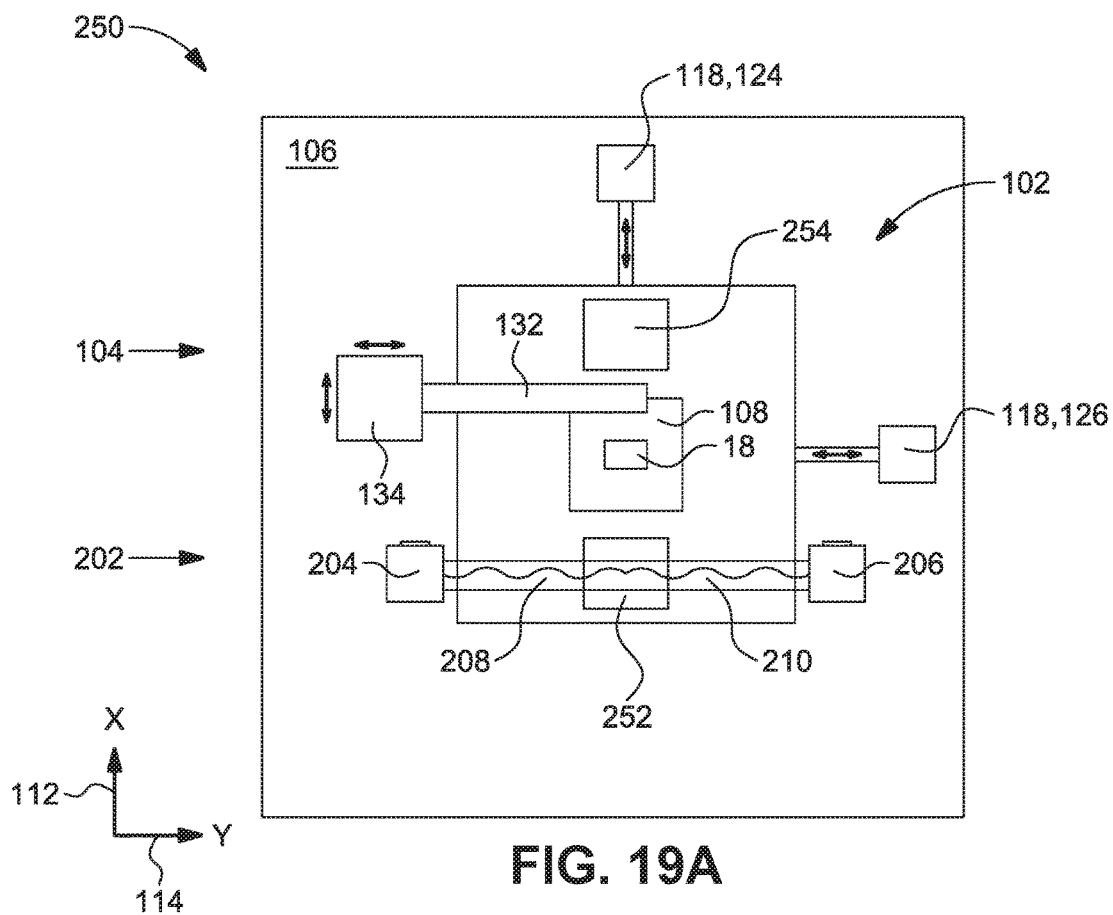
FIGS. 19A and 19B illustrate a top and a side view, respectively, of a debris collection apparatus including a metrology apparatus and a plurality of patches and/or debris collectors in accordance with aspects of the present disclosure.
Figure 19B:
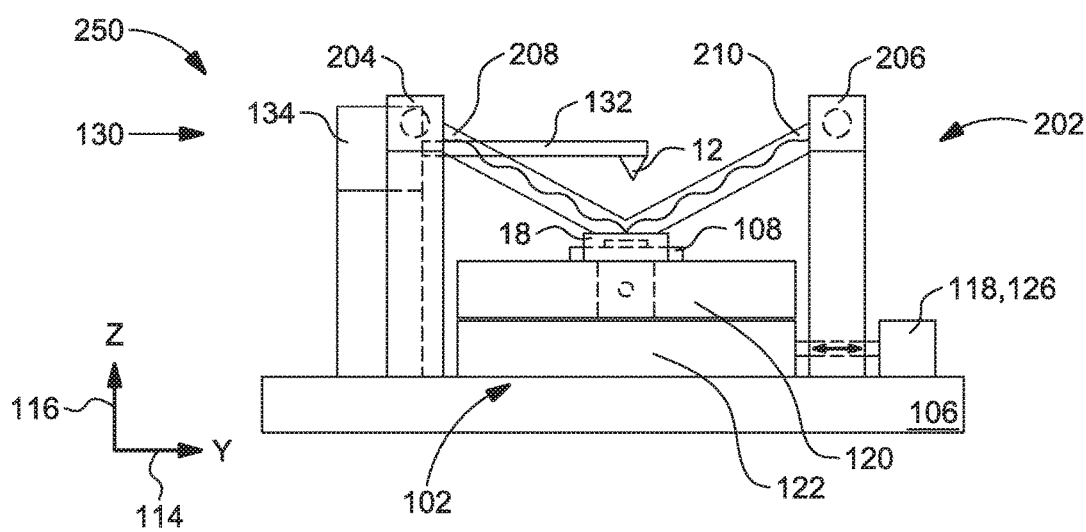
Figure 20A:
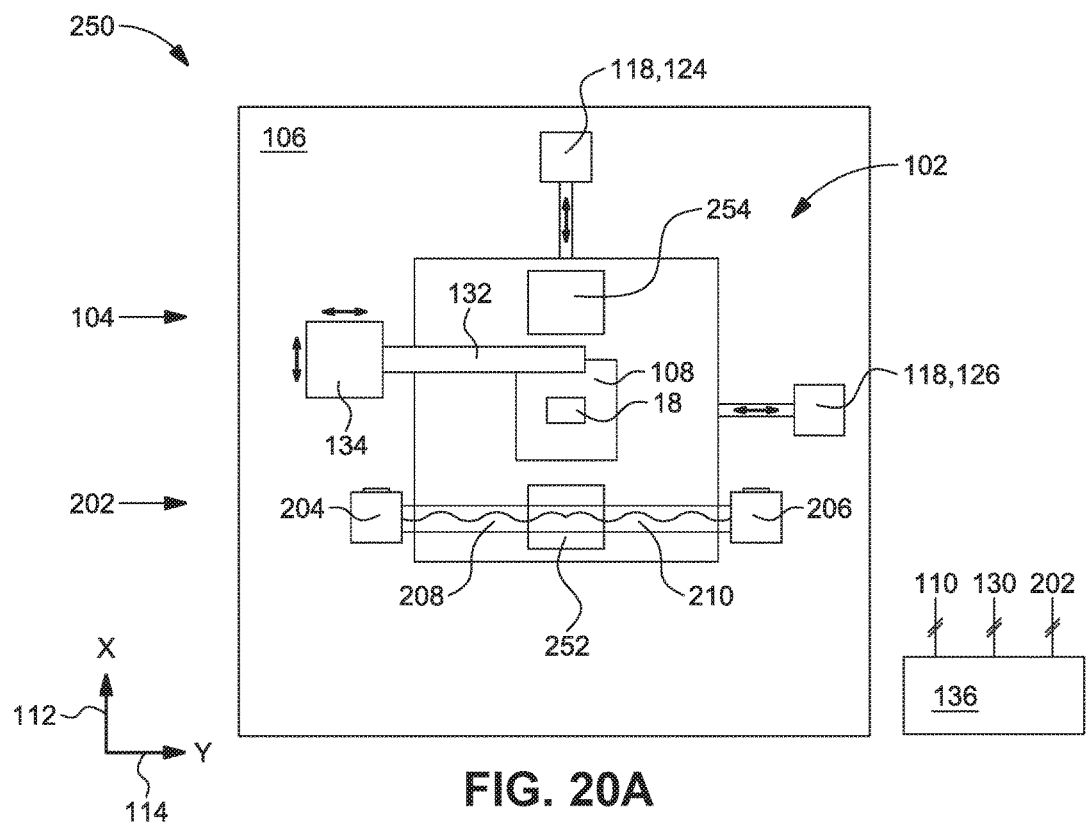
FIGS. 20A and 20B illustrate a top and a side view, respectively, of a debris collection apparatus including a metrology apparatus with a controller and a plurality of patches and/or debris collectors in accordance with aspects of the present disclosure.
Figure 20B:
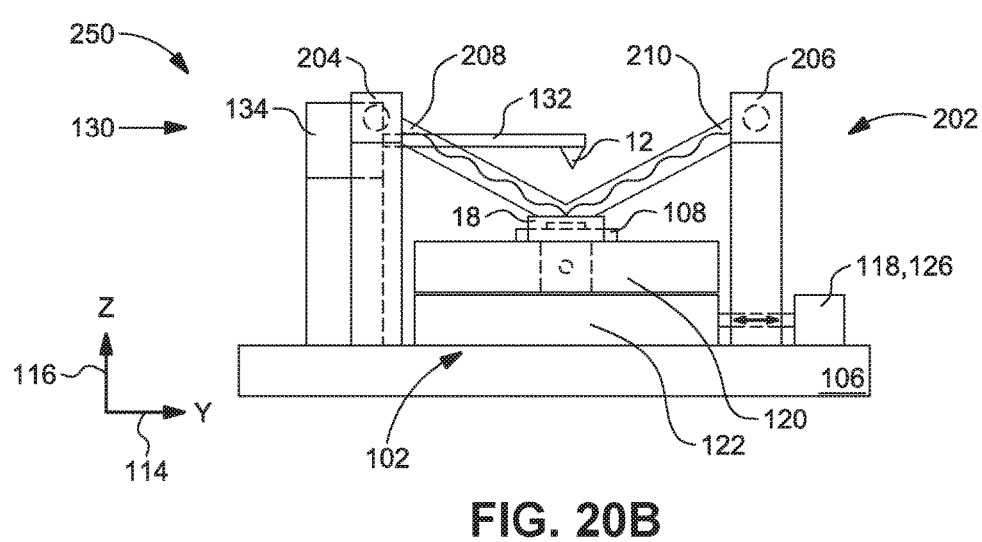

Referring now to FIGS. 19A, 19B, 20A and 20B, it will be appreciated that FIGS. 19A and 20A illustrate top view of a debris collection and metrology apparatus 250, and FIGS. 19B and 20B illustrate side views of a debris collection and metrology apparatus 250, according to aspects of the disclosure. Similar to the debris collection and metrology apparatuses 250 of FIGS. 17A, 17B, 18A and 18B, the debris collection and metrology apparatus 250 may include a substrate support assembly 102, a tip support assembly 104, a base 106, a metrology system 202, an energy source 204, and an energy detector 206. The debris collection and metrology apparatus 250 of FIGS. 17A, 17B, 18A and 18B may further include a first patch 252 and a second patch 254. In one aspect, the first patch 252 and the second patch 254 may be disposed on opposite sides of the substrate 18 and mounted to the fixture 108. The energy source 204 and the energy detector 206 may each be directed towards and trained on at least one of the first patch 252 and the second patch 254. The first patch 252 and the second patch 254 may embody any of the structures or attributes previously described. Additionally, or alternatively, the first patch 252 and the second patch 254 may include or may be configured as a collection pocket or collection through-hole for collecting debris or contaminate from the tip 12, as will be described in further detail with reference to FIGS. 30-37. For example, the debris collection and metrology apparatus 250, the energy source 204 and the energy detector 206 may each be directed towards the collection pocket or collection through-hole to analyze a material property of debris or contaminate 20 collected on the collection pocket or collection through-hole using the metrology system 202.

Actuation and/or adjustment of the substrate stage assembly 110, the tip stage assembly 130, or both, is capable of effecting at least three procedures using the debris collection and metrology apparatus 250. In accordance with an aspect of the present disclosure, debris may be removed from the substrate 18 and collected using a collection pocket or a collection through-hole as will be described in further detail below. The collection pocket or the collection through-hole may be a part of the first patch 252 and the second patch 254, or may be mounted or positioned at a location of the first patch 252 and the second patch 254.

During a first procedure, actuation and/or movement of the substrate stage assembly 110, the tip stage assembly 130, or both, effects contact between the tip 12 and a substrate 18 disposed on the fixture 108, such that debris 20 is transferred from the substrate 18 to the tip 12. During a second procedure, actuation and/or movement of the substrate stage assembly 110, the tip stage assembly 130, or both, effects contact between the tip 12 and the collection pocket or the collection through-hole of the first patch 252, thereby transferring debris 20 from the tip 12 to the collection pocket or the collection through-hole of the first patch 252. In one aspect, the actuation and/or movement of the tip 12 relative to the collection pocket or the collection through-hole of the first patch 252 may following a predetermined trajectory as will be described in further detail below with references to FIGS. 33 and 34. During a third procedure, actuation and/or movement of the substrate stage assembly 110 directs and trains each of the energy source 204 and the energy detector 206 onto the collection through-hole of the first patch 252, such that an incident energy beam 208 from the energy source 204 is incident upon the patch 252, and a sample energy beam 210 emanating from the patch 252 is incident up on the energy detector 206.

Turning to FIGS. 20A and 20B, the energy detector 206 may be coupled to the controller 136, such that the controller 136 receives the output signal from the energy detector 206 in response to the sample energy beam. The controller 136 may be configured to analyze the output signal from the energy detector 206 in response to the sample energy beam 210 and identify one or more material attributes of the collection pocket or the collection through-hole of the first patch 252, or debris disposed on the collection pocket or the collection through-hole of the first patch 252. Optionally, the energy source 204 may operative be coupled to the controller 136 of FIGS. 20A and 20B, such that the controller 136 may control attributes of the incident energy beam 208 that is generated by the energy source 204, such as, but not limited to an intensity of the incident energy beam 208, a frequency of the incident energy beam 208, or both. In one aspect, a direction of the energy source 204, the sample energy beam 210, and/or the energy detector 206 may be adjusted in response to the output signal from the energy detector 206.

Figure 21A:
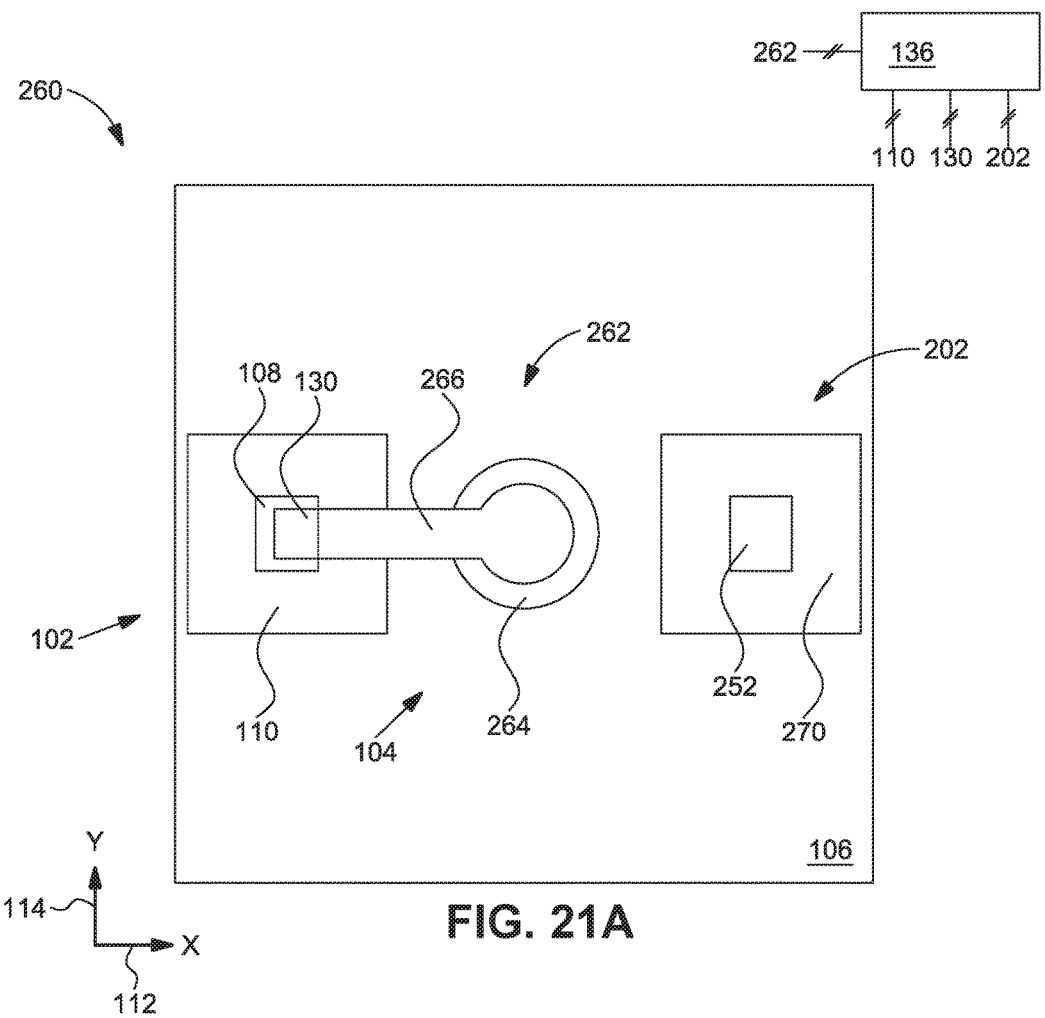
FIGS. 21A and 21B illustrate a top and a side view, respectively, of a debris collection apparatus including a robotic arm in accordance with aspects of the present disclosure.
Figure 21B:
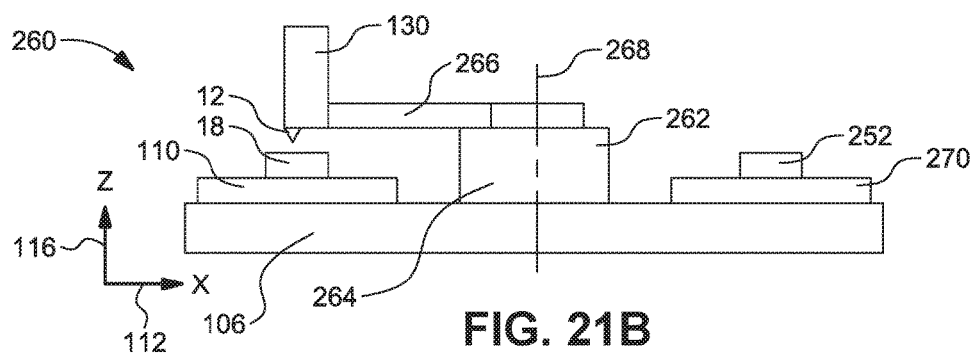

Referring now to FIGS. 21A and 21B, it will be appreciated that FIG. 21A illustrates a top view of a debris collection and metrology apparatus 260, according to an aspect of the disclosure, and FIG. 21B illustrates a side view of a debris collection and metrology apparatus 260, according to an aspect of the disclosure. Similar to the debris collection and metrology apparatus 200 and 250, illustrated in FIGS. 15-20, the debris collection and metrology apparatus 260 includes a substrate support assembly 102, a tip support assembly 104, a base 106, and a metrology system 202. However, in the debris collection and metrology apparatus 260, the tip support assembly 104 further includes a robot 262.

The robot 262 may include a motor 264 and a robotic arm 266. A proximal end of the robotic arm 266 may operatively be coupled to the base 106 via a motor 264, and the tip stage assembly 130 may operatively be coupled to a distal end of the robotic arm 266, such that operation of the motor 264 effects relative motion between the tip 12 and the base 106. According to an aspect of the disclosure, operation of the motor 264 effects rotational motion of the tip 12 relative to the base 106 about a rotational axis 268 of the robot 262.

The metrology system 202 includes a patch 252 and may include a metrology stage assembly 270 to support the patch 252. Alternatively, the patch 252 may be supported directly on or by the base 106, absent a metrology stage assembly 270. The metrology stage assembly 270 may be configured to effect relative motion between the patch 252 and the base 106 in translation along the x-direction 112, in translation along the y-direction 114, in translation along the z-direction 116, in rotation about the x-direction 112, in rotation about the y-direction 114, in rotation about the z-direction 116, combinations thereof, or any other relative motion known in the art. Further, the metrology stage assembly 270 may embody any of the structures or attributes described previously for the substrate stage assembly 110, the tip stage assembly 130, or both.

In FIGS. 21A and 21B, the robotic arm 266 is shown in a first position, such that the tip 12 is located proximal to the fixture 108. When the robotic arm 266 is located in the first position, motion of the substrate stage assembly 110, the tip stage assembly 130, or both, is sufficient to effect contact between the tip 12 and a substrate 18 mounted to the fixture 108. Accordingly, when the robotic arm 266 is located in its first position, the debris collection and metrology apparatus 260 may effect a transfer of debris 20 from the substrate 18 to the tip 12.

Figure 22A:
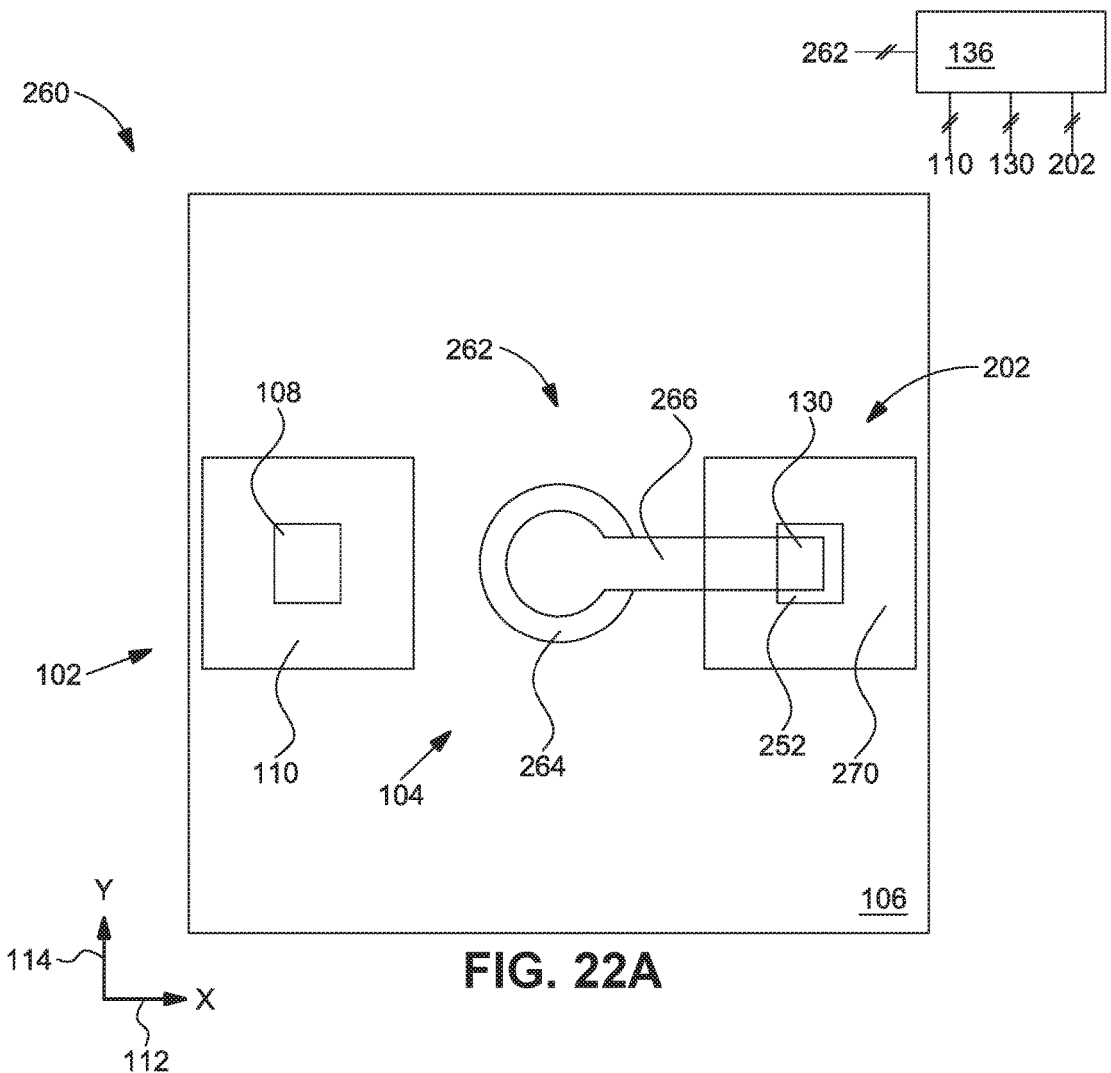
FIGS. 22A and 22B illustrate a top and a side view, respectively, of the debris collection apparatus of FIGS. 21A and 21B with the robotic arm in a second position.
Figure 22B:
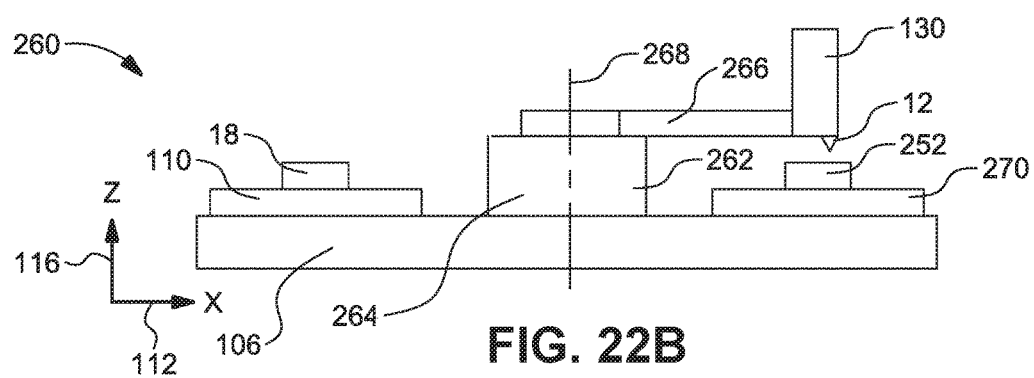

In FIGS. 22A and 22B, the robotic arm 266 is shown in a second position, such that the tip 12 is located proximal to a metrology system 202. When the robotic arm 266 is located in its second position, motion of the tip stage assembly 130, or combined motion of the tip stage assembly 130 and the metrology stage assembly 270, is sufficient to effect contact between the tip 12 and the patch 252. Accordingly, when the robotic arm 266 is located in the second position, the debris collection and metrology apparatus 270 may effect a transfer of debris 20 from the tip 12 to the patch 252. In accordance with an aspect of the present disclosure, the patch 252 may include or be configured as a collection pocket or collection through-hole for collecting debris or contaminate from the tip 12, as will be described in further detail with reference to FIGS. 30-37. Although not shown in FIGS. 21A and 21B, the debris collection and metrology apparatus 270 may include an energy source 204 and an energy detector 206 directed towards and trained on the patch 252, similar or identical to those illustrated in FIGS. 17A and 17B to perform metrology analysis on the patch 252, debris 20 disposed on the patch 252, or both.

According to an aspect of the disclosure, any one or more of the robot 262, the substrate stage assembly 110, the tip stage assembly 130, and the metrology stage assembly 270 in the debris collection and metrology apparatus 260 may operatively be coupled to the controller 136 for control thereof. Accordingly, the controller 136 may be configured to actuate the robot 262 to switch configurations between the aforementioned first position shown in FIGS. 21A and 21B and the second position shown in FIGS. 22A and 22B.

Figure 23A:
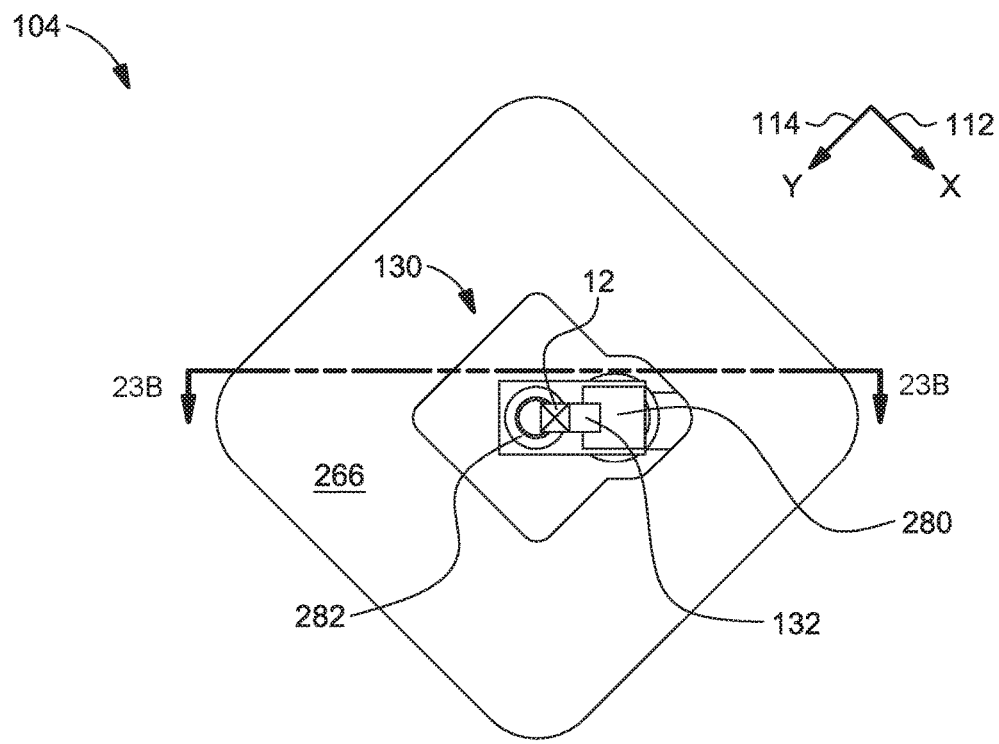
FIGS. 23A and 23B illustrate a top and a side view, respectively, of a tip support assembly in accordance with aspects of the present disclosure.
Figure 23B:
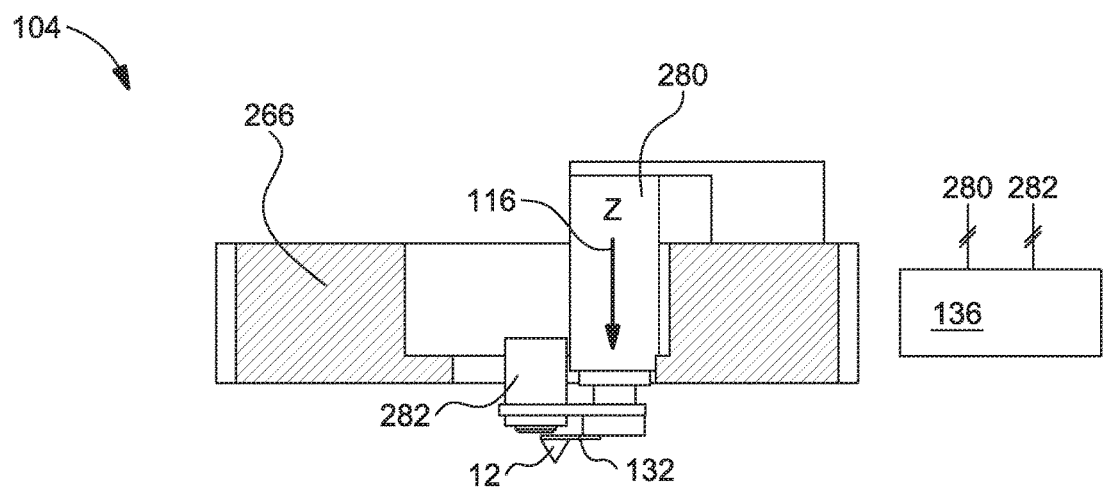

Referring now to FIGS. 23A and 23B, it will be appreciated that FIG. 23A illustrates a bottom view of a tip support assembly 104, according to an aspect of the disclosure, and FIG. 23B illustrates a partial cross-sectional side view of a tip support assembly 104 taken along section line 23B-23B according to an aspect of the disclosure. The tip support assembly 104 illustrated in FIGS. 23A and 23B may be especially suited for integration into the robotic arm 266, as shown in FIGS. 21A, 21B, 22A and 22B. However, it will be appreciated that the tip support assembly 104 may be advantageously incorporated into other debris collection and/or metrology systems to satisfy particular needs, as will be appreciated by one skilled in the art in view of the present disclosure.

The tip support assembly 104 illustrated in FIGS. 23A and 23B includes a z-actuator 280, a camera 282, or both, however, it will be appreciated that the tip support assembly 104 may embody any other structures or attributes previously discussed for tip support assemblies, not limited to means for translational motion along the x-direction 112 or the y-direction 114, as well as rotational motion about any of the x-direction 112, the y-direction 114, and the z-direction 116.

A proximal end of the z-actuator 280 may operatively be coupled to the robotic arm 266, and a distal end of the z-actuator 280 may operatively be coupled to the tip 12 via the tip cantilever 132, the camera 282, or both. Accordingly, operation of the z-actuator 280 effects relative motion between the tip 12, the camera 282, or both along the z-direction 116. The z-actuator 280 may include a rotary motor and a screw structure, a linear servo-motor structure, a pneumatic or hydraulic piston structure, a piezoelectric structure, or any other linear actuator structure known in the art.

It will be appreciated that the z-actuator 280 may operatively be coupled to the controller 136 to control a relative motion between the robotic arm 266 and the tip 12, the camera 282, or both. Further the camera 282 may also be coupled to the controller 136 to provide images of a substrate proximate to the tip 12 to a user display, a machine vision algorithm for control of the tip 12, or both.

Figure 24A:
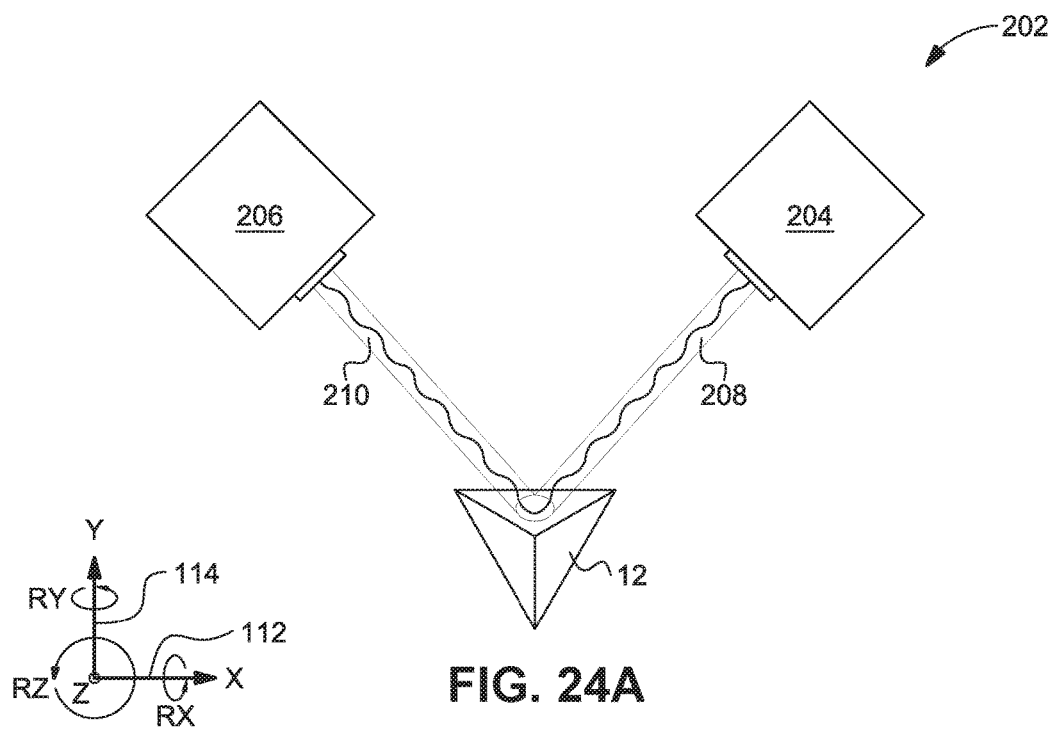
FIGS. 24A and 24B illustrate a bottom and a side view, respectively, of a metrology system usable with a tetrahedral tip in accordance with aspects of the present disclosure.
Figure 24B:
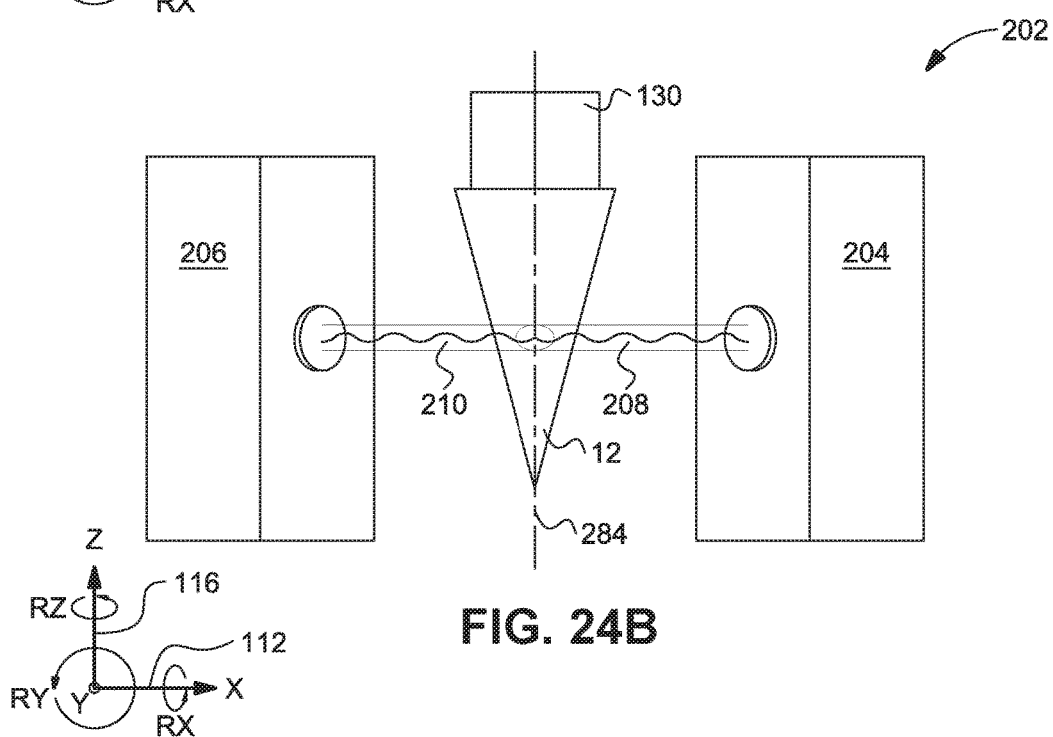

Referring now to FIGS. 24A and 24B, it will be appreciated that FIG. 24A illustrates a bottom view of a metrology system 202, which may be the same or a similar the metrology system 202 previously described with reference to FIGS. 15-20, although it will be appreciated by one skilled in the art that the metrology system 202 of FIGS. 24A and 24B may be representative of other systems including at least a tip 12, a tip stage assembly 13, an energy source 204, and an energy detector 206. FIG. 24B illustrates a side view of a metrology system 202, according to an aspect of the disclosure. The structure of the metrology system 202 illustrated in FIGS. 24A and 24B may be applicable to the debris collection and metrology apparatus 200 illustrated in FIGS. 15 and 16, where metrology procedures are performed directly on the tip 12, debris 20 disposed on the tip 12, or both. However, it will be appreciated that the metrology system 202 illustrated in FIGS. 24A and 24B may be advantageously applicable to other metrology systems and apparatus. In one aspect, the specific tip 12 shown in FIGS. 24A and 24B may include a tetrahedral shape. As shown in FIGS. 24A and 24B, the tip 12 with the tetrahedral shape is free of any debris 20. Accordingly, the metrology system 202 may be used to analyze attributes of the tip 12 absent any debris 20 attached to the tip 12.

The energy source 204 may be directed towards and trained on the tip 12, such that an incident energy beam 208 generated by the energy source 204 is incident upon the tip 12, and the energy detector 206 may be directed towards and trained on the tip 12, such that a sample energy beam 210 generated in response to the incident energy beam 208 on the tip 12 is received by the energy detector 206. The tip stage assembly 130 may operatively be coupled to the tip 12, such that the tip stage assembly 130 may move the tip 12 relative to the energy source 204, the energy detector 206, or both, in translation along or rotation about any of the x-direction 112, the y-direction 114, and the z-direction 116. According to an aspect of the disclosure, the tip stage assembly 130 is configured to at least rotate the tip 12 about a tip longitudinal axis 284 extending through the tip 12. According to an aspect of the present disclosure, the tip 12 specifically illustrated in FIGS. 24A and 24B includes a tetrahedral shape.

The tip stage assembly 130, the energy source 204, the energy detector 206, or combinations thereof, may operatively be coupled to the controller 136 for control thereof. Accordingly, the controller 136 may selectively direct the incident energy beam 208 onto different surfaces of the tip 12 by actuating the tip stage assembly 130, and the controller 136 may receive one or more signals from the energy detector 206 that are indicative of an attribute of the resulting sample energy beam 210. As shown in FIGS. 24A and 24B, the tip 12 may be free of any debris 20. Accordingly, the metrology system 202 may be used to analyze attributes of the tip 12 absent any debris 20 attached to the tip 12.

Figure 25A:
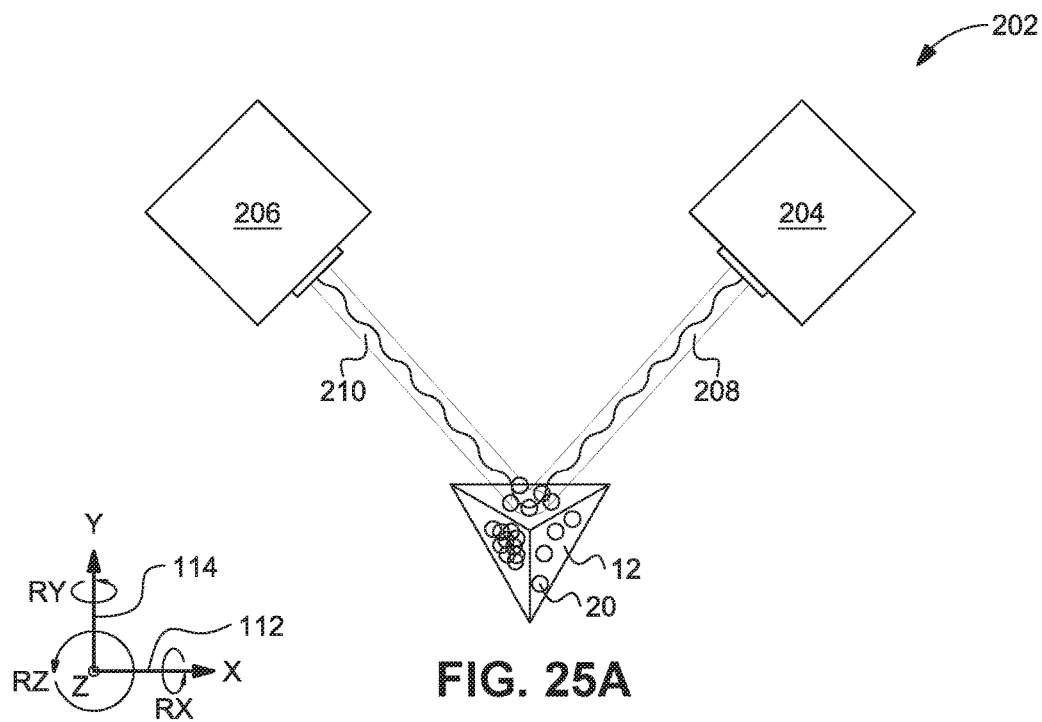
FIGS. 25A and 25B illustrate a bottom and a side view, respectively, of the metrology system of FIGS. 24A and 24B with debris attached to the tetrahedral tip.
Figure 25B:
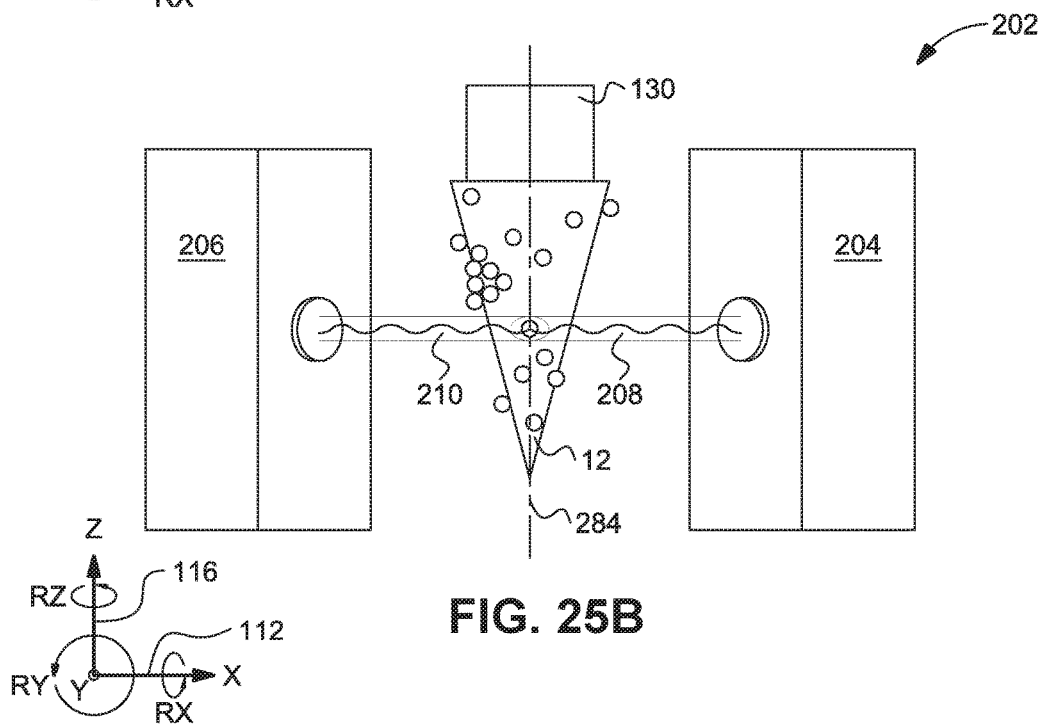

Referring now to FIGS. 25A and 25B, it will be appreciated that FIG. 25A illustrates a bottom view of a metrology system 202, and FIG. 25B illustrates a side view of a metrology system 202, according to an aspect of the disclosure. The metrology system 202 illustrated in FIGS. 25A and 25B may embody any of the structures or attributes described for the metrology system 202 illustrated in FIGS. FIGS. 15-20, 24A and 24B. However, the metrology system 202 illustrated in FIGS. 25A and 25B shows debris 20 attached to the tip 12 with the tetrahedral shape. Accordingly, the metrology system 202 may be used to analyze attributes of the tip 12, debris 20 attached to the tip 12, or both.

Figure 26A:
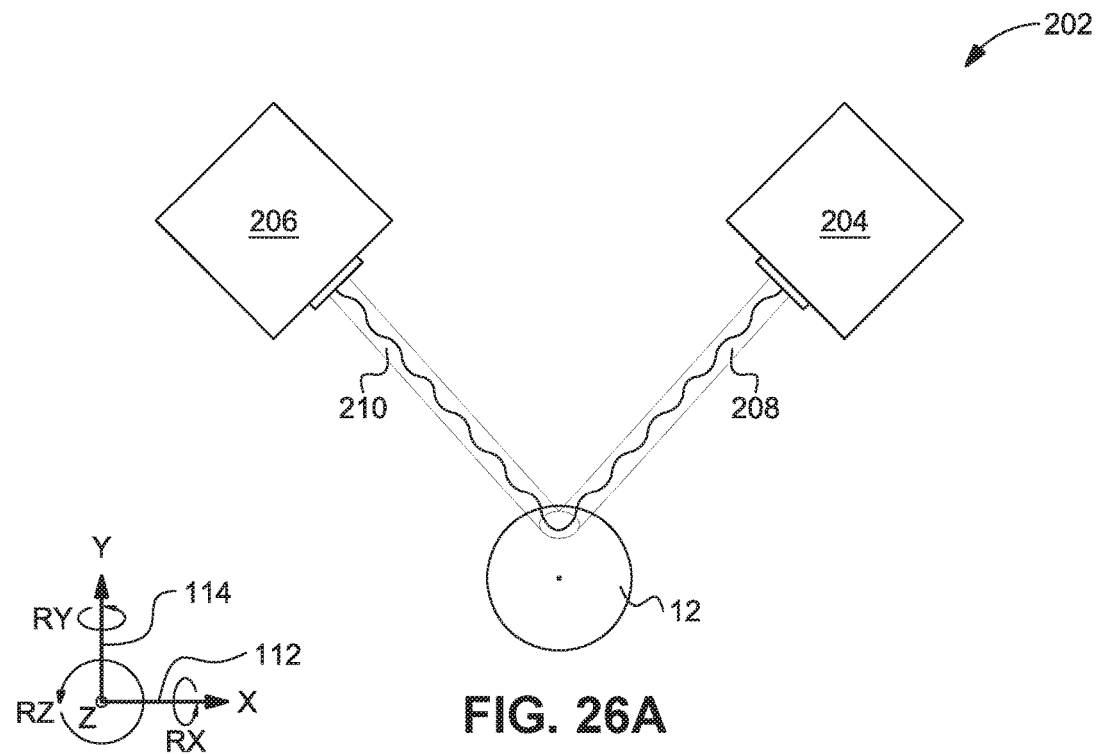
FIGS. 26A and 26B illustrate a bottom and a side view, respectively, of a metrology system usable with a circular conical tip in accordance with aspects of the present disclosure.
Figure 26B:
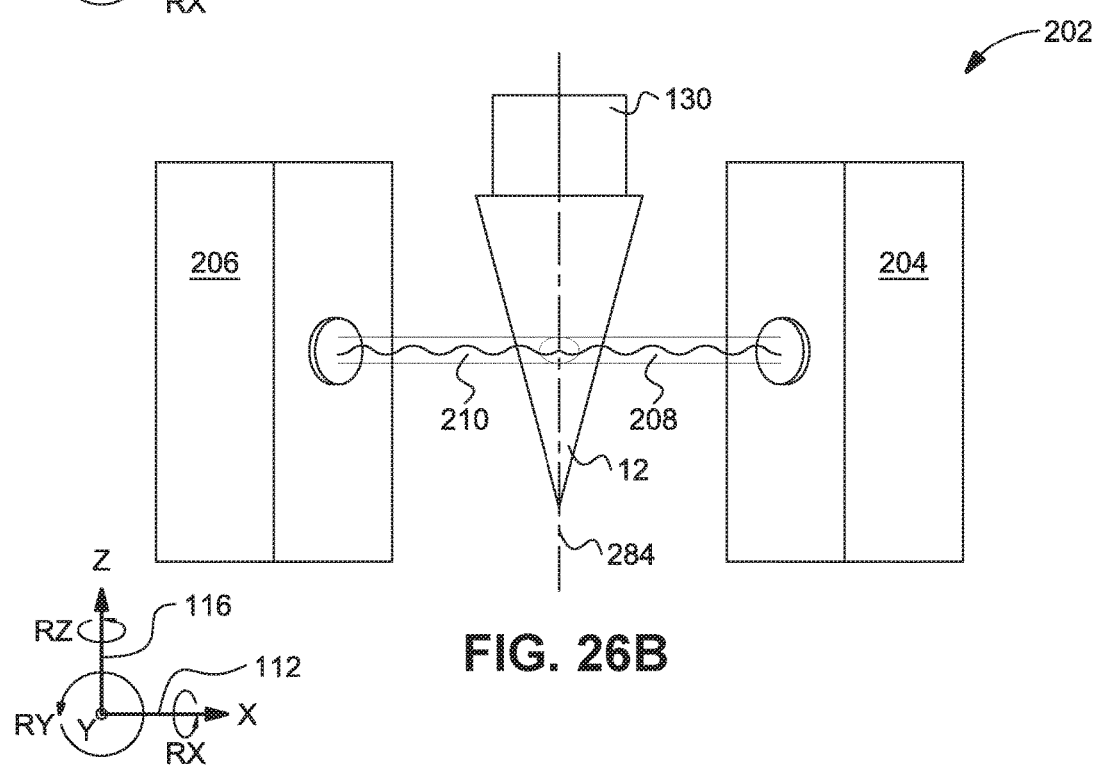

Referring now to FIGS. 26A and 26B, it will be appreciated that FIG. 26A illustrates a bottom view of a metrology system 202, and FIG. 26B illustrates a side view of a metrology system 202, according to an aspect of the disclosure. The metrology system 202 illustrated in FIGS. 26A and 26B may embody any of the structures or attributes of the metrology system 202 illustrated in FIGS. 24A and 24B. However, unlike FIGS. 24A and 24B, the specific tip 12 illustrated in FIGS. 26A and 26B includes a circular conical shape. As shown in FIGS. 26A and 26B, the tip 12 with the circular conical shape is free of any debris 20. Accordingly, the metrology system 202 may be used to analyze attributes of the tip 12 absent any debris 20 attached to the tip 12.

Figure 27A:
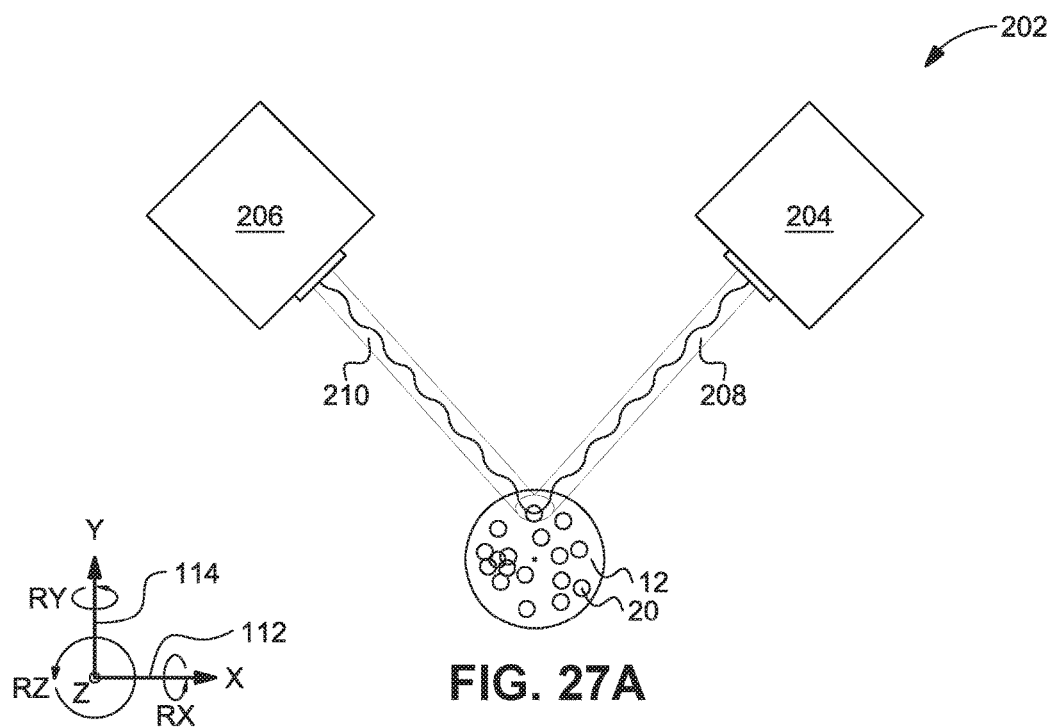
FIGS. 27A and 27B illustrate a bottom and a side view, respectively, of the metrology system of FIGS. 26A and 26B with debris attached to the circular conical tip.
Figure 27B:
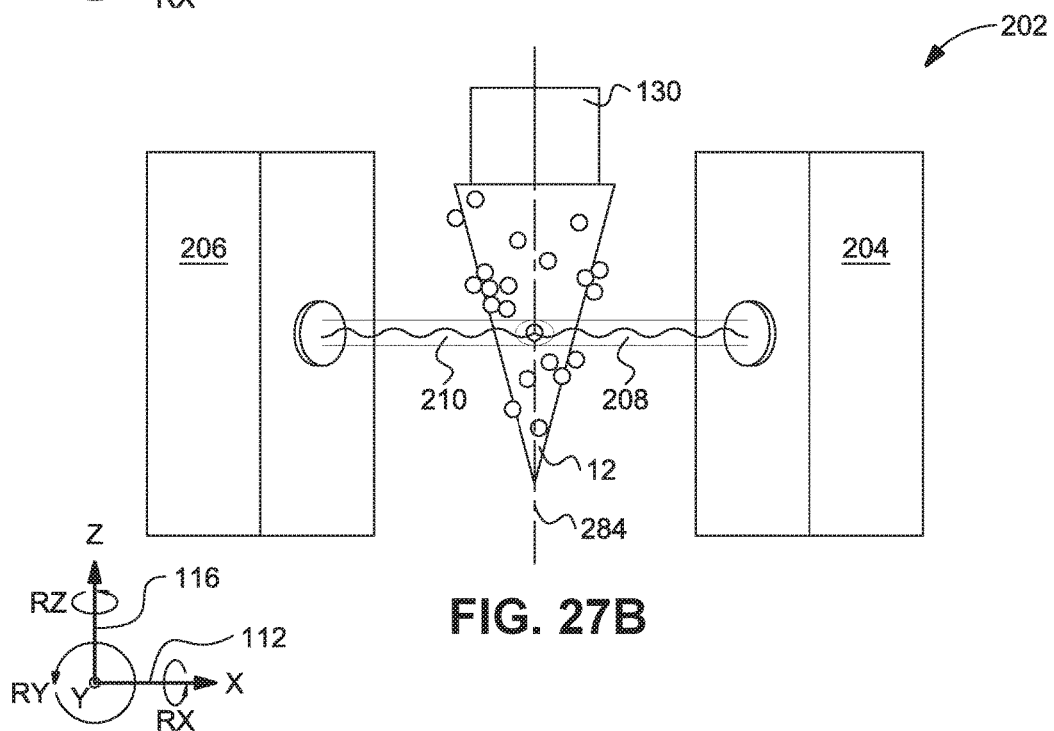

Referring now to FIGS. 27A and 27B, it will be appreciated that FIG. 27A illustrates a bottom view of a metrology system 202, and FIG. 27B illustrates a side view of a metrology system 202, according to an aspect of the disclosure. The metrology system 202 illustrated in FIGS. 27A and 27B may embody any of the structures or attributes described for the metrology system 202 illustrated in FIGS. 26A and 26B. However, the metrology system 202 illustrated in FIGS. 27A and 27B shows debris 20 attached to the tip 12 with the circular conical shape. Accordingly, the metrology system 202 may be used to analyze attributes of the tip 12, debris 20 attached to the tip 12, or both.

Figure 28A:
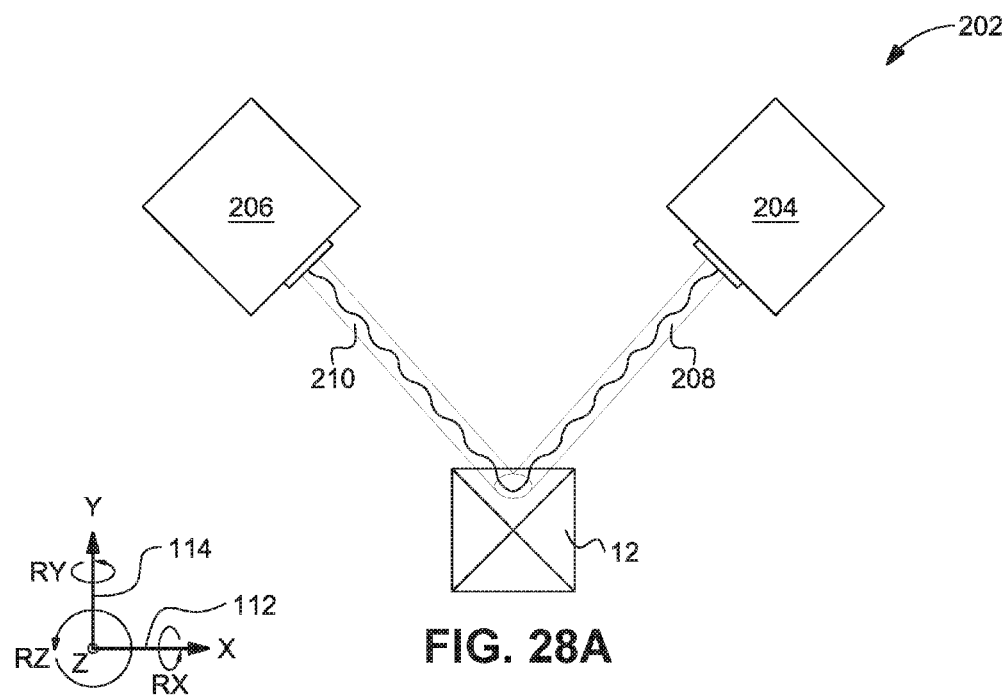
FIGS. 28A and 28B illustrate a bottom and a side view, respectively, of a metrology system usable with a pyramidal tip in accordance with aspects of the present disclosure.
Figure 28B:
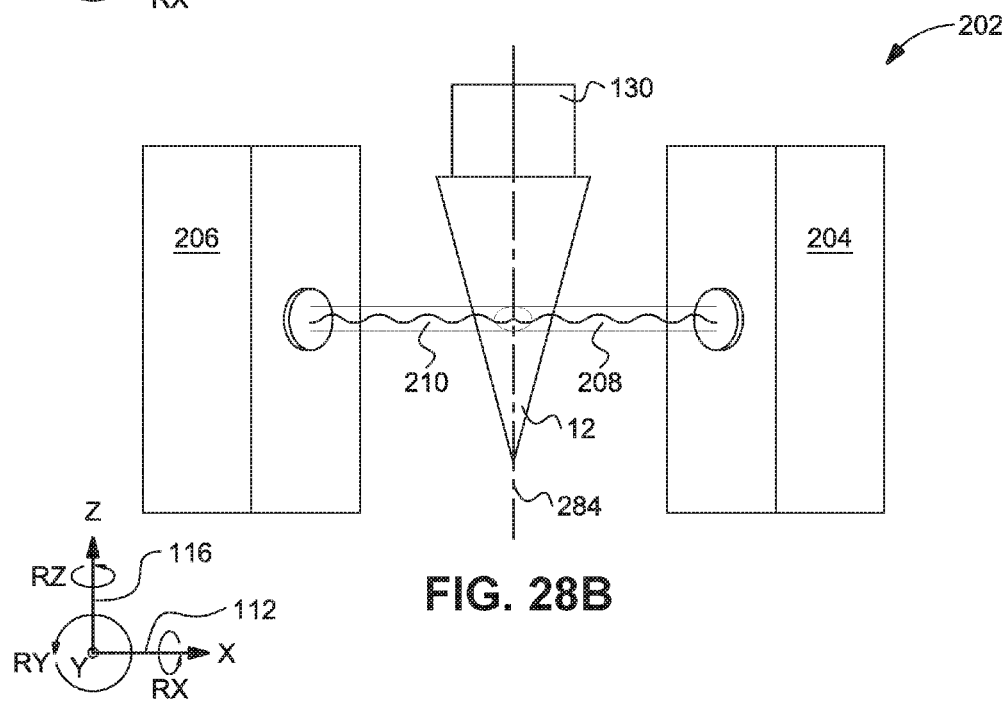

Referring now to FIGS. 28A and 28B, it will be appreciated that FIG. 28A illustrates a bottom view of a metrology system 202, according to an aspect of the disclosure, and FIG. 28B illustrates a side view of a metrology system 202, according to an aspect of the disclosure. The metrology system 202 illustrated in FIGS. 28A and 28B may embody any of the structures or attributes of the metrology system 202 illustrated in FIGS. 24A and 24B. However, unlike FIGS. 24A and 24B, the specific tip 12 illustrated in FIGS. 28A and 28B includes a pyramidal shape. As shown in FIGS. 28A and 28B, the tip 12 with the pyramidal shape is free of any debris 20. Accordingly, the metrology system 202 may be used to analyze attributes of the tip 12 absent any debris 20 attached to the tip 12.

Figure 29A:
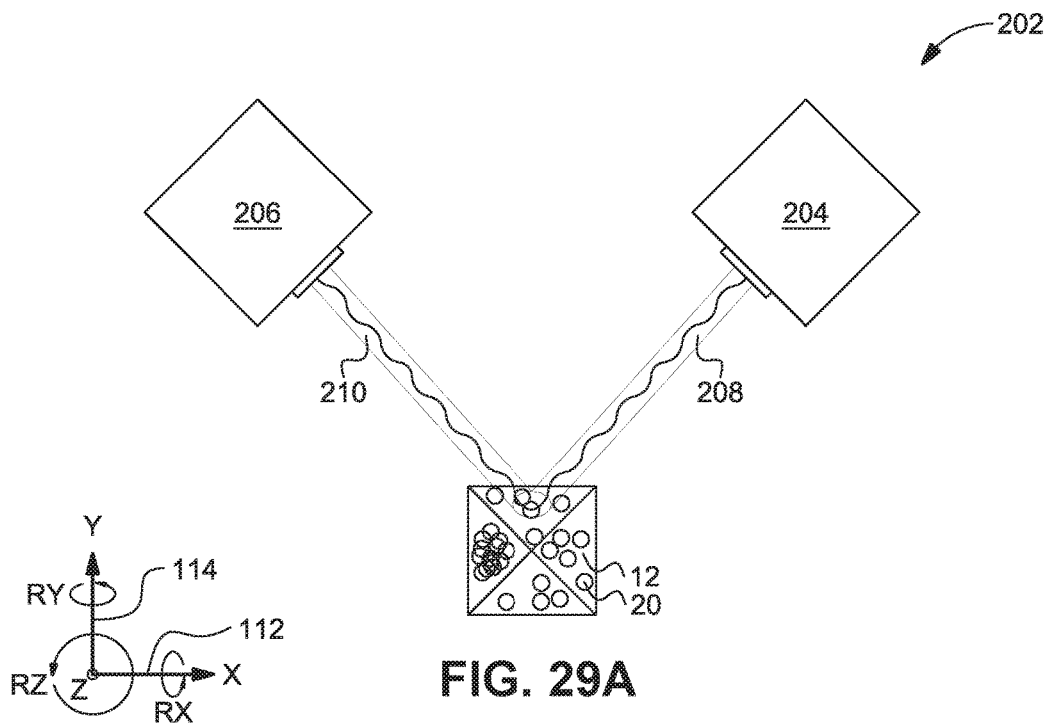
FIGS. 29A and 29B illustrate a bottom and a side view, respectively, of the metrology system of FIGS. 28A and 28B with debris attached to the pyramidal tip.
Figure 29B:
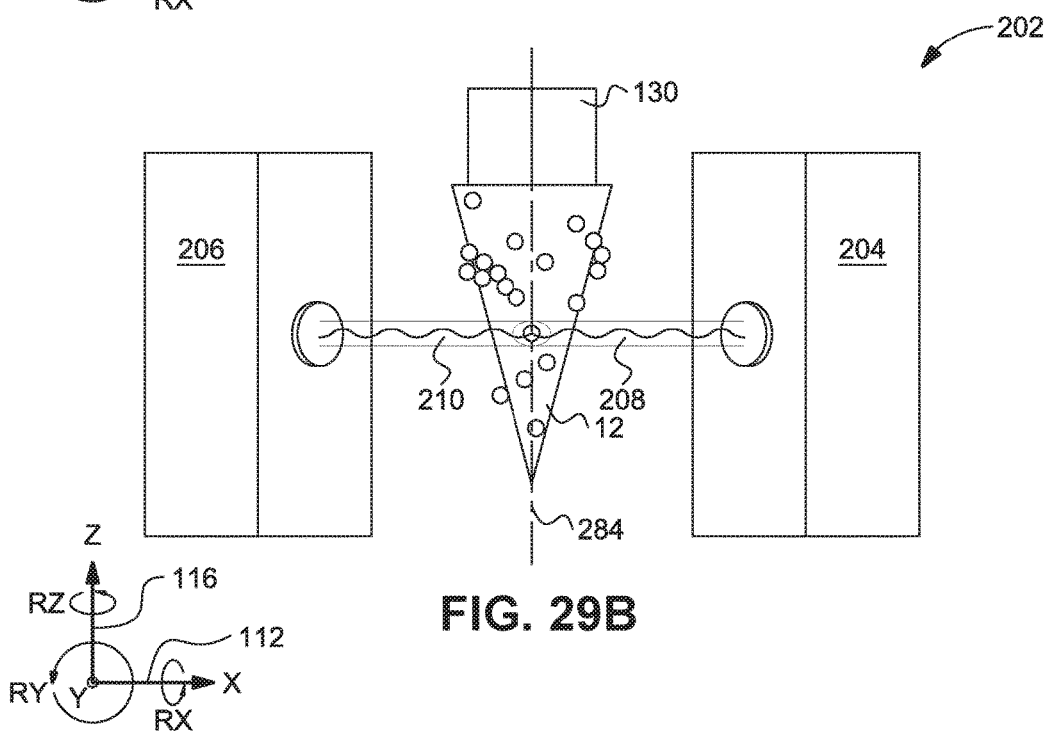

Referring now to FIGS. 29A and 29B, it will be appreciated that FIG. 29A illustrates a bottom view of a metrology system 202, according to an aspect of the disclosure, and FIG. 29B illustrates a side view of a metrology system 202, according to an aspect of the disclosure. The metrology system 202 illustrated in FIGS. 29A and 29B may embody any of the structures or attributes described for the metrology system 202 illustrated in FIGS. 28A and 28B. However, the metrology system 202 illustrated in FIGS. 29A and 29B shows debris 20 attached to the tip 12 with the pyramidal shape. Accordingly, the metrology system 202 may be used to analyze attributes of the tip 12, debris 20 attached to the tip 12, or both.

Turning to FIGS. 30-37, exemplary contaminate collectors with a collection pocket or a collection through-hole will now be described. Referring now to FIGS. 30A and 30B, FIG. 30A illustrates a cross-sectional side view (taken at 30A-30A of FIG. 30B) of a contaminate collector 30 for collecting contaminate samples 33 from a tip 12, and the tip 12 may be the same or similar to those previously described with respect to exemplary debris detection and collection systems. The contaminate samples 33 may include one or more pieces of debris or particles 20 described above. The contaminate collector 30 may define a collection pocket 32 including at least three sidewalls 34 extending from a first upper surface 36 to a second upper surface 38. The height (h) of the sidewalls 34 may be selected such that at least a portion of the tip 12 may be inserted into a depth of the collection pocket 32. In one aspect, the height (h) of the sidewalls 34, which defines the depth of the collection pocket 32, may be between 25% to 200% a length (L) of the tip 12. In one aspect, the height (h) of the sidewalls may be selected to promote refraction for spectroscopy to analyze the contaminate samples 33 that may be deposited in or on the contaminate collector 30.

In one aspect, an intersection between the first upper surface 36 and the sidewalls 34 forms a first set of internal edges, and an intersection between the second upper surface 38 and the sidewalls 34 forms a second set of internal edges. The sidewalls 34 may define at least one internal surface extending from the first upper surface 36 to the second upper surface 38. In one aspect, an irradiation source, such as the energy source 204 described above, may be configured and arranged to direct an incident irradiation onto the internal surface or surfaces of the contaminate collector 30. In one aspect, an irradiation detector, such as the energy detector 206 described above, may be configured and arranged to receive a sample irradiation from the one or more internal surfaces of the contaminate collector 30, the sample irradiation being generated by the incident irradiation being directed onto and reflect back from onto the one or more internal surface or surfaces of the contaminate collector 30.

Figure 30A:
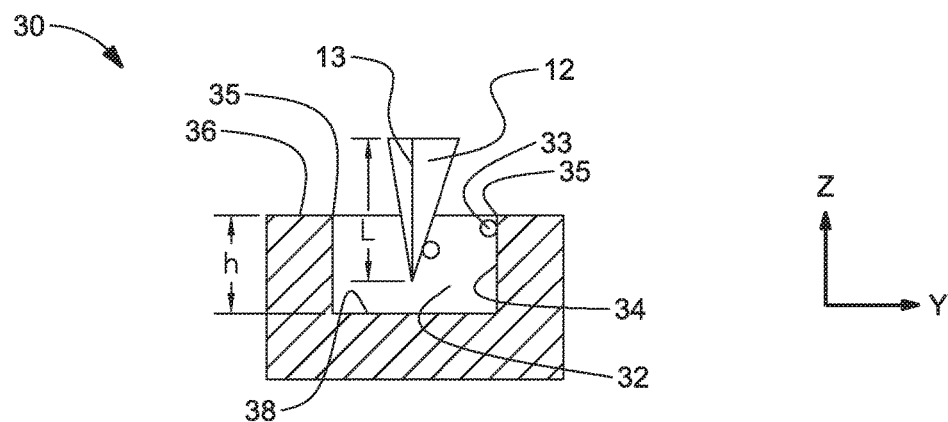
FIGS. 30A and 30B illustrate a side cross-sectional view and a top view, respectively, of a contaminate collector with a collection pocket having a triangular layout in accordance with aspects of the present disclosure.
Figure 30B:
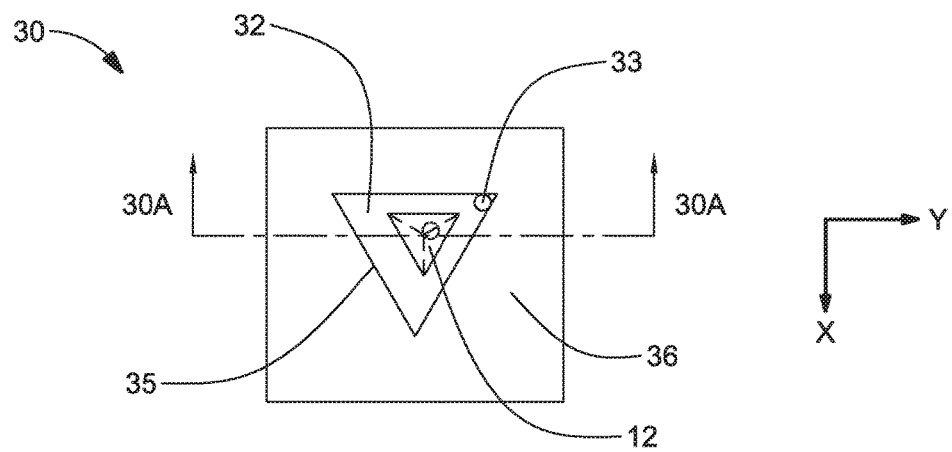

As shown in FIG. 30B, the three sidewalls 34, and the corresponding first internal edge, may form an equilateral triangle outline when viewed from the top. Each set of adjacent sidewalls 34 may form a set of contaminate collection edges 35. In one aspect, a tip 12 having a tetrahedral shape may be used with the contaminate collector 30 of FIGS. 30A and 30B. One or more edges 13 of the tip 12 may be maneuvered near, adjacent to, brushed against, or dragged against the one or more contaminate collection edges 35 of the collection pocket 32 such that contaminate samples 33 may be transferred from the tip 12 to the collection pocket 32. In select aspects, the contaminate collector 30 may include three sidewalls 34 that form a non-equilateral triangular outline (e.g., isosceles, scalene, acute-angled, right-angled, or obtuse-angled triangles) when viewed from the top. The non-equilateral triangular cross-section define the contaminate collection edges 35 that are non-equal and may therefore be adapted to extract contaminate samples 33 from tips of various sizes and/or shapes, as will be appreciated by one skilled in the art in view of the present disclosure. In one aspect, each edge of the contaminate collection edges 35 may have a length of less than or equal to 10 mm to reduce the amount of travel needed for the tip 12 to transfer contaminate samples 33 to the collection pocket 32, particularly when the contaminate samples 33 are nanometer level structures.

Figure 31A:
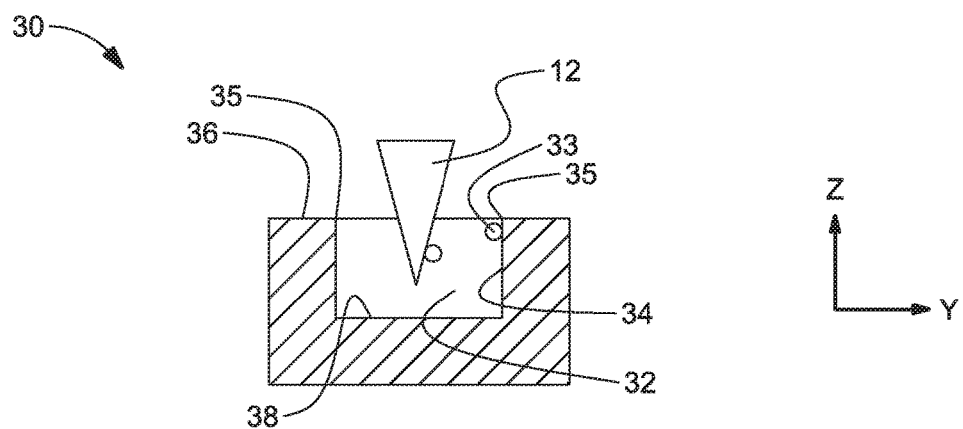
FIGS. 31A and 31B illustrate a side cross-sectional view and a top view, respectively, of a contaminate collector with a collection pocket having a circular layout in accordance with aspects of the present disclosure.
Figure 31B:
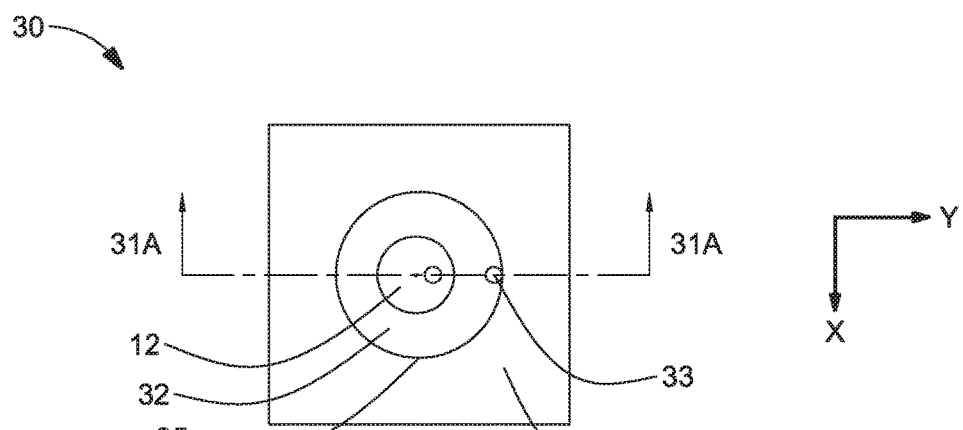

Referring now to FIGS. 31A and 31B, FIG. 31A illustrates a cross-sectional side view (taken at 31A-31A of FIG. 31B) of a contaminate collector 30 for collecting contaminate samples 33 from a tip 12, and the tip 12 may be the same or similar to those previously described with respect to exemplary debris detection and collection systems. The contaminate collector 30 may define a collection pocket 32 including sidewalls 34 extending from a first upper surface 36 to a second upper surface 38. The height (h) of the sidewalls 34 may be selected such that at least a portion of the tip 12 may be inserted into a depth of the collection pocket 32. In one aspect, the height (h) of the sidewalls 34, which defines the depth of the collection pocket, may be between 25% to 200% a length (L) of the tip 12. In one aspect, the height (h) of the sidewalls may be selected to promote refraction for spectroscopy to analyze the contaminate samples 33 that may be deposited in or on the contaminate collector 30.

In one aspect, as shown in FIG. 31B, the contaminate collector 30 may include a cylindrical sidewall 34 forming a circular outline when view from the top. A contaminate collection internal edge 35 may be formed at an intersection between the first upper surface 36 and the sidewall 34. In one aspect, a tip 12 having a circular conical shape may be used with the contaminate collector 30 of FIGS. 31A and 31B. A surface of the conical tip 12 may be maneuvered near, adjacent to, brushed against, or dragged against the contaminate collection edge 35 of the collection pocket 32 such that contaminate samples 33 may be transferred from the tip 12 to the collection pocket 32. In select aspects, the contaminate collector 30 may include a sidewall 34 that defines an oval or elliptical outline when viewed from the top, and may therefore be adapted to extract contaminate samples 33 from tips of various sizes and/or shapes, as will be appreciated by one skilled in the art in view of the present disclosure. In one aspect, a diameter of the contaminate collection edge 35 may be less than 10 mm wide. In select aspects, the diameter of the contaminate collection edge 35 may be less than or equal to 500 microns wide to reduce the amount of travel needed for the tip 12 to transfer contaminate samples 33 to the collection pocket 32, particularly when the contaminate samples 33 are nanometer level structures.

Figure 32A:
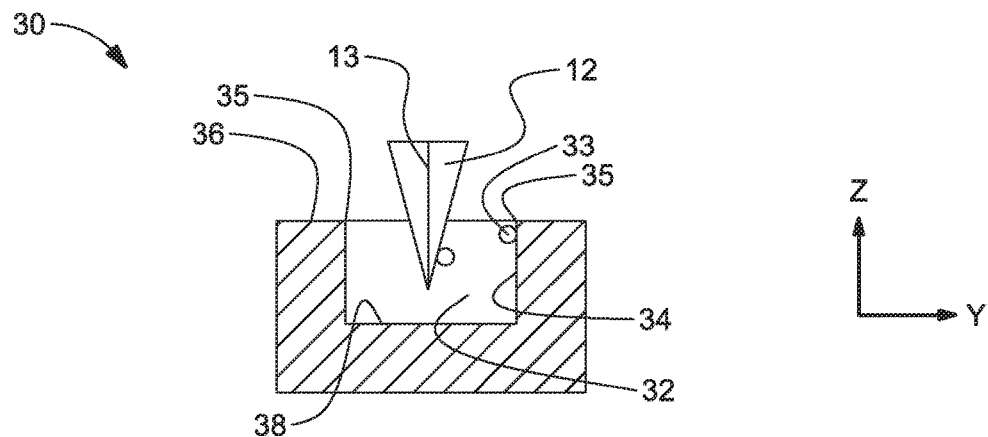
FIGS. 32A and 32B illustrate a side cross-sectional view and a top view, respectively, of a contaminate collector with a collection pocket having a square layout in accordance with aspects of the present disclosure.
Figure 32B:
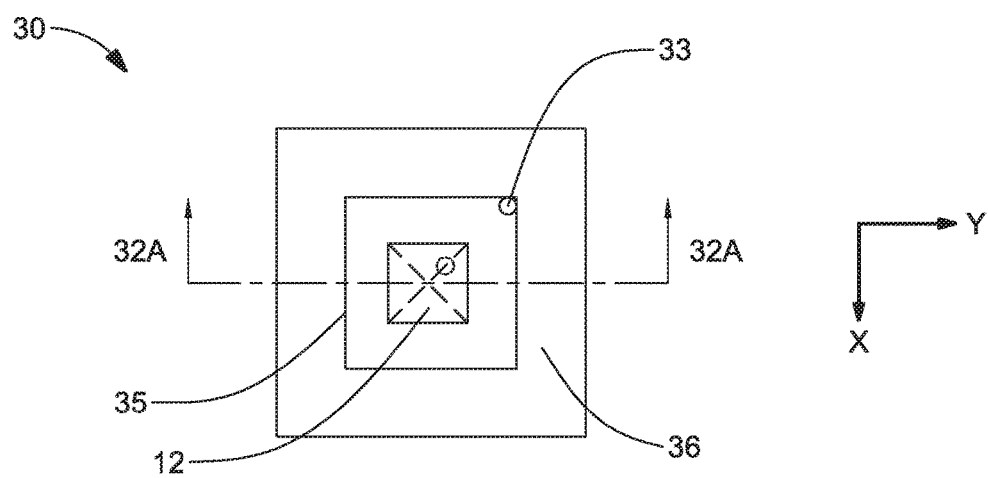

Referring now to FIGS. 32A and 32B, FIG. 32A illustrates a cross-sectional side view (taken at 32A-32A of FIG. 32B) of a contaminate collector 30 for collecting contaminate samples 33 from a tip 12, and the tip 12 may be the same or similar to those previously described with respect to exemplary debris detection and collection systems. The contaminate collector 30 may define a collection pocket 32 including sidewalls 34 extending from a first upper surface 36 to a second upper surface 38. The height (h) of the sidewalls 34 may be selected such that at least a portion of the tip 12 may be inserted into a depth of the collection pocket 32. In one aspect, the height (h) of the sidewalls 34, which defines the depth of the collection pocket, may be between 25% to 200% a length (L) of the tip 12. In one aspect, the height (h) of the sidewalls may be selected to promote refraction for spectroscopy to analyze the contaminate samples 33 that may be deposited in or on the contaminate collector 30.

In one aspect, as shown in FIG. 32B, the contaminate collector 30 may include four sidewalls 34 forming a rectangular or square outline when view from the top. Each set of adjacent sidewalls 34 may form a contaminate collection internal edge 35. In one aspect, a tip 12 having a pyramidal shape may be used with the contaminate collector 30 of FIGS. 32A and 32B. One or more edges 13 of the tip 12 may be maneuvered near, adjacent to, brushed against, or dragged against one or more collection internal edges 35 of the collection pocket 32 such that contaminate samples 33 may be transferred from the tip 12 to the collection pocket 32. In one aspect, each edge of the contaminate collection edges 35 may have a length of less than or equal to 10 mm to reduce the amount of travel needed for the tip 12 to transfer contaminate samples 33 to the collection pocket 32, particularly when the contaminate samples 33 are nanometer level structures.

Although particular parings of tip and collection pocket 32 shapes are discussed above in reference to FIGS. 30A, 30B, 31A, 31B, 32A and 32B, it will be appreciated that any combination of tips 12 and collection pocket 32 shapes may be utilized together or interchangeably. For example, the conical tip 12 of FIGS. 31A and 31B may be used with the triangular collection pocket 32 of FIGS. 30A and 30B. Additionally, although exemplary triangular, rectangular and circular contaminate collectors are shown in FIGS. 30-32, contaminate collectors with five or more sidewalls may also be used.

Figure 33A:
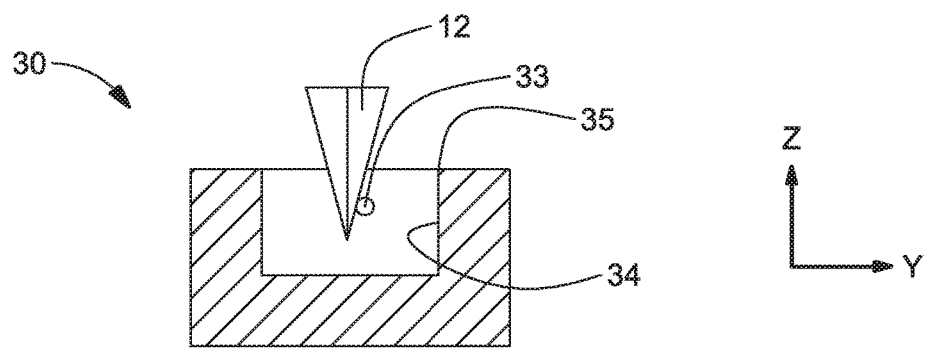
FIGS. 33A to 33C illustrate an exemplary debris collection process using a contaminate collector with a collection pocket in accordance with aspects of the present disclosure.
Figure 33B:
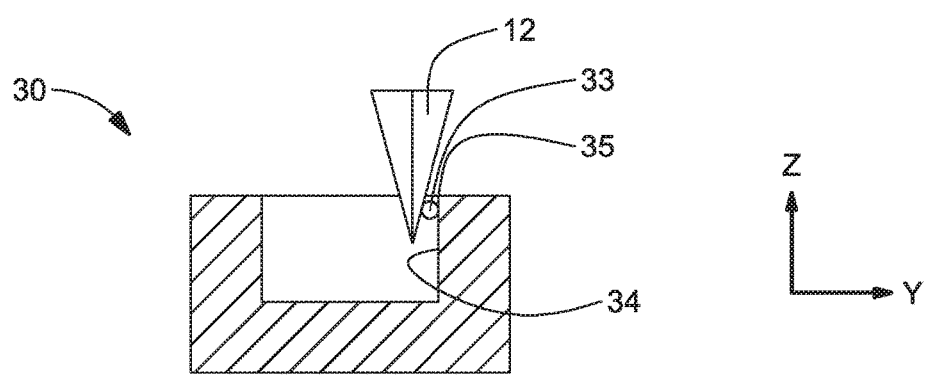
Figure 33C:
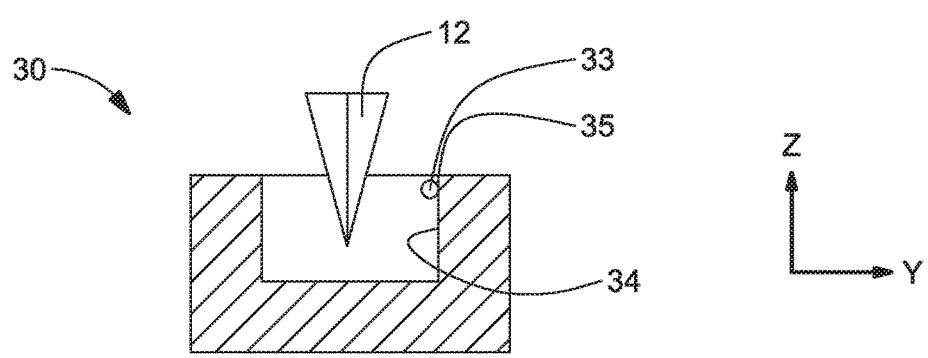

Turning to FIGS. 33A to 33C, an exemplary process of maneuvering the tip 12 and transferring contaminate samples 33 from a tip 12 to the contaminate collector 30, such as those described above with reference to FIGS. 30-32, will now be described. It will be appreciated that similar step may also be applied for transferring contaminate samples to a contaminate collector 40, as generally described with reference FIGS. 35-37. As shown in FIG. 33A, a tip 12 may first be positioned centrally above an opening of the collection pocket 32 in the x- and y-directions. The tip 12 may then be lowered at least partially in the z-direction into the collection pocket 32 without contacting the sidewalls 34 of the collection pocket 32. Next, as shown in FIG. 33B, the tip 12 may then be maneuvered towards one of the sidewalls 34 in the x- and/or y-directions. The tip 12 may simultaneously be maneuvered upward in the z-direction such that contaminate samples 33 may brush against or come in close contact with a contaminate collection edge 35 of the collection pocket 32, whereby contaminate samples 33 may be transferred from the tip 12 to at least a side portion of the contaminate collection edge 35.

In one aspect, the travel of the tip 12 from the position shown in FIG. 33A to FIG. 33B may be defined as a quadratic function such that the tip 12 moves towards and past the contaminate collection edge 35 via a parabolic trajectory, a scraping motion and/or wiping motion. The tip 12 may continue to travel upward and to the right of the contaminate collection edge 35, from the position shown in FIG. 33B, before being maneuvered back to a starting position as shown in FIG. 33A. In one aspect, the travel of the tip 12 may be defined as a linear function depending on the size and shape of the tip 12 and the collection pocket 32.

Other trajectories and travel paths for the tip 12 will be appreciated by those skilled in the art in view of the present disclosure.

Figure 34A:
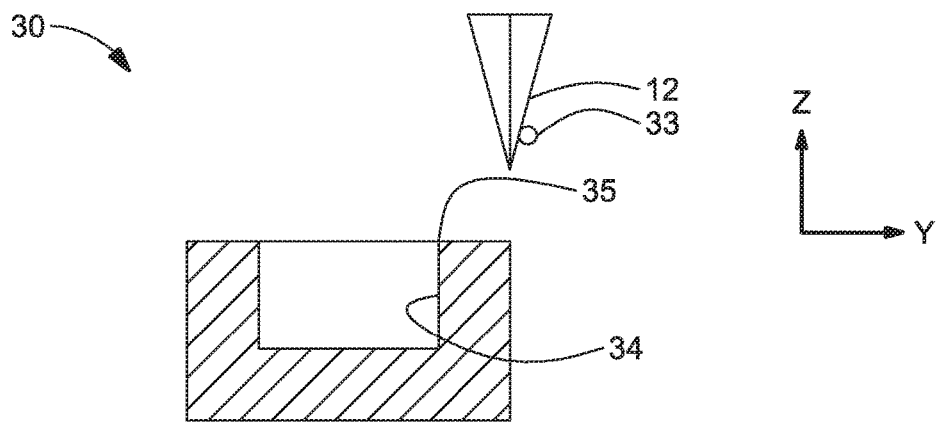
FIGS. 34A to 34C illustrate another exemplary debris collection process using a contaminate collector with a collection pocket in accordance with aspects of the present disclosure.
Figure 34B:
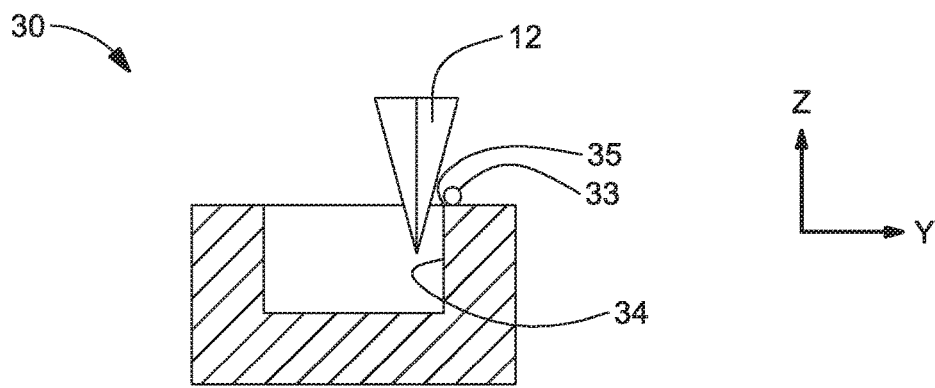
Figure 34C:
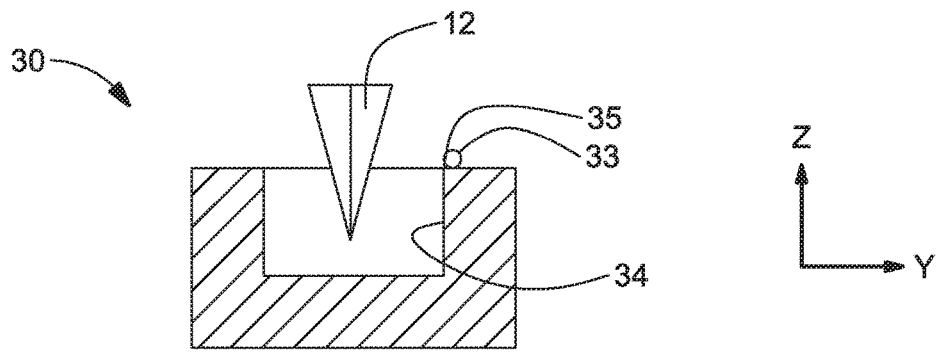

Additionally or alternatively, as shown in FIG. 34A to FIG. 34C, the tip 12 may initially be positioned above and offset from a center of the collection pocket 32 in the x- and y-directions. The tip 12 may then be moved downward in the z-direction while also being moved towards the center of the collection pocket 32 in the x- and/or y-directions until at least a portion of the tip 12 is located at least partially within the collection pocket 32. In moving the tip 12 into the collection pocket 32, contaminate samples 33 may brush against or come in close contact with the contaminate collection edge 35 of the collection pocket 32, whereby contaminate samples 33 are transferred from the tip 12 to at least a top portion of the contaminate collection edge 35.

In one aspect, the travel of the tip 12 from the position shown in FIG. 34A to FIG. 34C may be defined as a quadratic function such that the tip 12 moves towards and past the contaminate collection edge 35 via a parabolic trajectory, a scraping motion and/or wiping motion. In one aspect, the travel of the tip 12 may be defined as a linear function depending on the size and shape of the tip 12 and the collection pocket 32. Other trajectories and travel paths for the tip 12 will be appreciated by those skilled in the art in view of the present disclosure.

In accordance with an aspect of the disclosure, the above tip maneuvers of FIGS. 33A-33C and/or 34A-34C may be repeated such that the tip 12 contacts different portions of the contaminate collection edge 35. For example, where the contaminate collection edge 35 has a circular geometry, as described above with reference to FIGS. 31A and 31B, the tip 12 may be maneuvered to contact the 12 o'clock and 6 o'clock locations of the contaminate collection edge 35 (based on a top view orientation shown in FIG. 31B) in order to transfer contaminate samples 33 from different corresponding portions of the tip 12. In view of the present disclosure, it will be appreciated by one skilled in the art that the tip, maneuver may be repeated to contact additional portions or all portions of the contaminate collection edge 35. In one aspect, the tip 12 may be maneuvered to transfer contaminate samples 33 from the tip 12 to the contaminate collection edge 35 by brushing against or coming in close contact with a contaminate collection edge 35 at the 12 o'clock, 3 o'clock, 6 o'clock, and 9 o'clock locations. By collecting contaminate samples 33 at different locations on the contaminate collection edge 35, compositions of collected contaminate samples derived from different portions of the tip 12 can be determined by defining the metrology location at different corresponding portions of the contaminate collection edge 35.

In accordance with an aspect of the disclosure, the above tip maneuvers of FIGS. 33A-33C and/or 34A-34C may be repeated such that different portions of the tip 12 may contact or come in close contact with a same location of the contaminate collection edge 35, thereby depositing all or most of the contaminate samples 33 from the tip 12 to the same location on the contaminate collection edge 35. For example, the tip 12 may be rotated about the z-axis after transferring contaminate samples 33 to the contaminate collection edge 35, as shown in FIG. 33B or 34B, and successively maneuvered to pass a same common location on the contaminate collection edge 35. Additionally, or alternatively, the contaminate collection edge 35, as shown in FIG. 33B or 34B, may be rotated about the z-axis after transferring contaminate samples 33 from the tip 12 to the contaminate collection edge 35. Furthermore, in addition to the collection pockets 32 and collection through-holes 46 described in the present disclosure (which have collection edges that completely encircle a tip 12), a collection edge or a set of collection edges that do not completely encircle the tip 12 may also be used. For example, the collection edge may consist of a single linear edge or a single C-shaped edge. In one aspect, where a set of collection edges is used, the collection edges together may encircle less than 75% of the tip 12, and in select aspects, the collection edges together may encircle less than 50% of the tip 12. By collecting contaminate samples 33 at the same common location on the contaminate collection edge 35, an entire composition of the collected contaminate samples 33 from the tip 12 can be determined by defining the common location on the contaminate collection edge 35 as the metrology location.

In one aspect, the above tip maneuvers of FIGS. 33A-33C and/or 34A-34C may be combined and used successively such that an upward and laterally outward motion may be followed by a downward and laterally inward motion, or vice versa, to transfer contaminate samples 33 from the tip 12 to the contaminate collection edge 35. The successive motions may assist in improving the speed of collecting contaminate samples 33 from the tip 12.

Figure 35A:
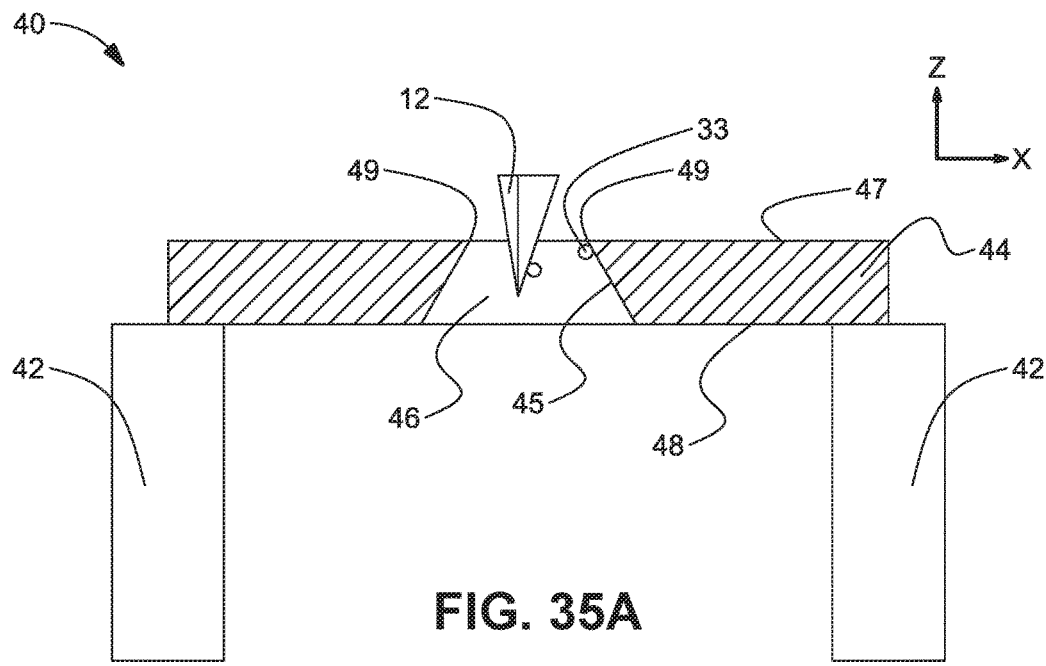
FIGS. 35A and 35B illustrate a side cross-sectional view and a top view, respectively, of a contaminate collector with a collection through-hole defining a truncated tetrahedron passage in accordance with aspects of the present disclosure.
Figure 35B:
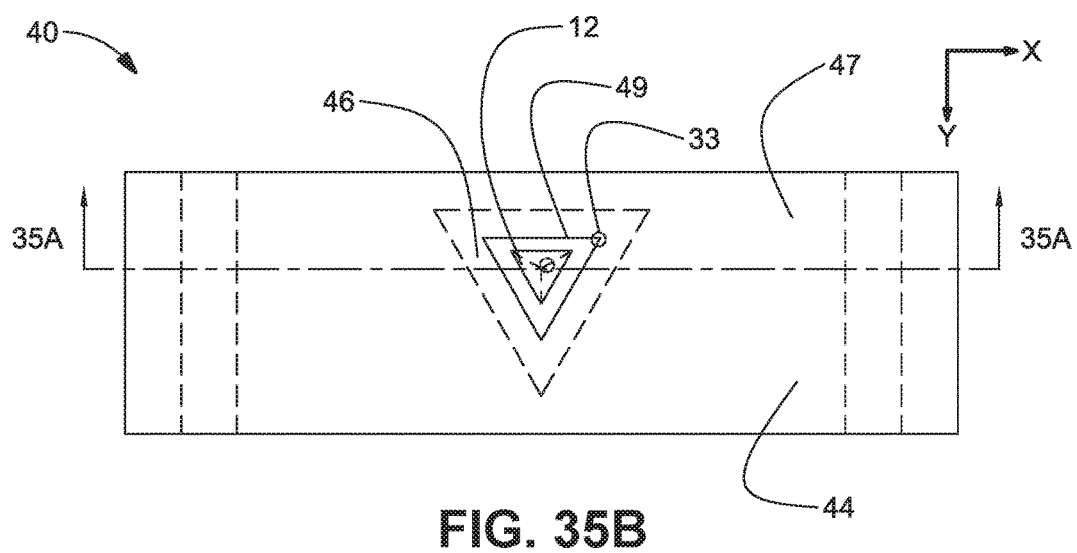

Turning to FIGS. 35-37, exemplary contaminate collectors with a collection through-hole will now be described. Referring now to FIGS. 35A and 35B, FIG. 35A illustrates a cross-sectional view (taken at 35A-35A of FIG. 35B) of a contaminate collector 40 for collecting contaminate samples 33 from a tip 12, and the tip 12 may be the same or similar to those previously described with respect to exemplary debris detection and collection systems of the present disclosure. The contaminate collector 40 may include at least a stand 42 and a platform 44, and the platform 44 may include an internal cut out having a sidewall 45 to define a collection through-hole 46. In one aspect, the platform 44 may include an upper surface 47 and a lower surface 48, and the sidewall 45 may extend from the upper surface 47 to the lower surface 48. A collection lip edge 49 may be defined at an intersection between the sidewall 45 and the upper surface 47. The stand 42 and the platform 44 may be fixed together, or they may be provided as separate components.

In one aspect the contaminate collector 40 may be transported from one location to another, particularly when the collection and metrology systems are separate units, are not integrated together, and/or are not located in the same location. The contaminate collector 40, or the platform 44 individually, may be moved from the collection system to the metrology system for analysis of the collected contaminate samples 33.

As shown in FIGS. 35A and 35B, the sidewall 45 of the contaminate collector may be beveled such that the collection through-hole 46 narrows in a direction towards a tip entry location. In accordance with an aspect of the present disclosure, the sidewall 45 may be beveled such that the through-hole 46 defines a truncated tetrahedron passage with a generally triangular outline when viewed from above, as shown in FIG. 35B. In operation, as shown in FIGS. 35A and 35B, a tetrahedron shaped tip 12 may be positioned to enter the collection through-hole 46 of the contaminate collector 40 from above in the z-direction. The tip 12 may be maneuvered at least downwardly in the z-direction to enter into the collection through-hole 46. Once at least a portion of the tip 12 has entered into the through-hole 46, the tip 12 may then be maneuvered laterally in an x- and/or y-directions towards sidewall 45 and the collection lip edge 49 of the contaminate collector 40. While moving laterally, the tip 12 may simultaneously be maneuvered upward in the z-direction such that contaminate samples 33 may brush against or come in close contact with the collection lip edge 49 and/or the sidewall 45, whereby contaminate samples 33 are transferred from the tip 12 to the collection lip edge 49 and/or the sidewall 45. The trajectory and travel of the tip 12 may be the same or similar to those described above with reference to FIGS. 33A-33C.

Additionally, or alternatively, contaminate samples 33 may be removed from the tip 12 by initially positioning the tip 12 above the collection through-hole 46 of the contaminate collector 40 in the z-direction and offset from a center of the through-hole 46 in the x- and/or y-directions. The tip 12 may then be moved downward in the z-direction while also being moved towards the center of the through-hole 46 in the x- and/or y-directions until at least a portion of the tip 12 is located at least partially within the through-hole 46. In moving the tip 12 in the through-hole 46, contaminate samples 33 may brush against or come in close contact with the collection lip edge 49 of the through-hole 46, whereby contaminate samples 33 are transferred from the tip 12 to at least a top portion of the collection lip edge 49. The trajectory and travel of the tip 12 may be the same or similar to those described above with reference to FIGS. 34A-34C.

Figure 36A:
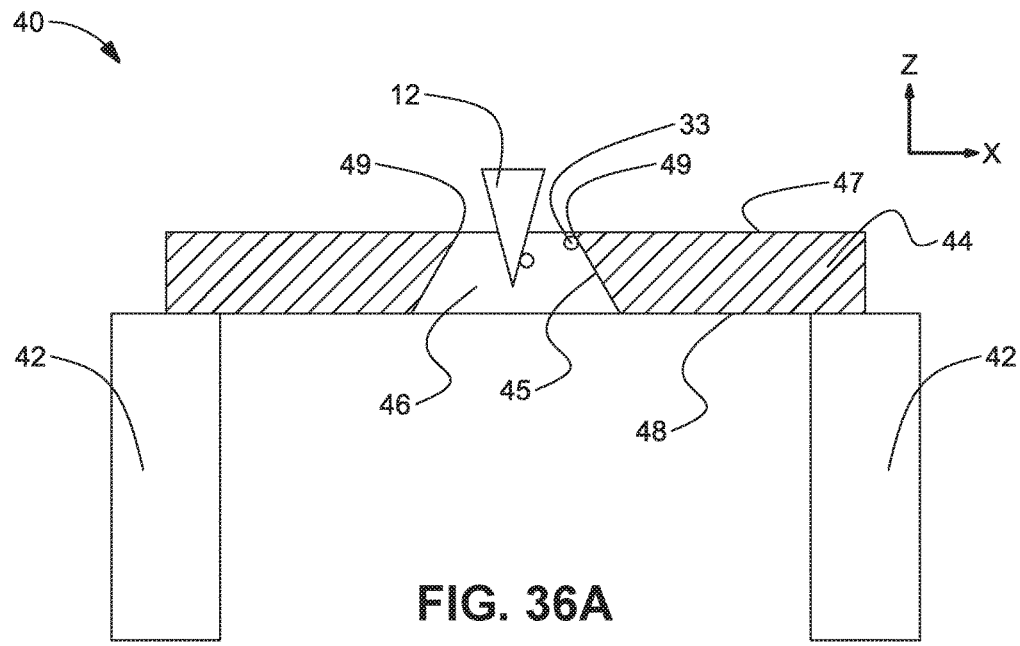
FIGS. 36A and 36B illustrate a side cross-sectional view and a top view, respectively, of a contaminate collector with a collection through-hole defining a truncated conical passage in accordance with aspects of the present disclosure.
Figure 36B:
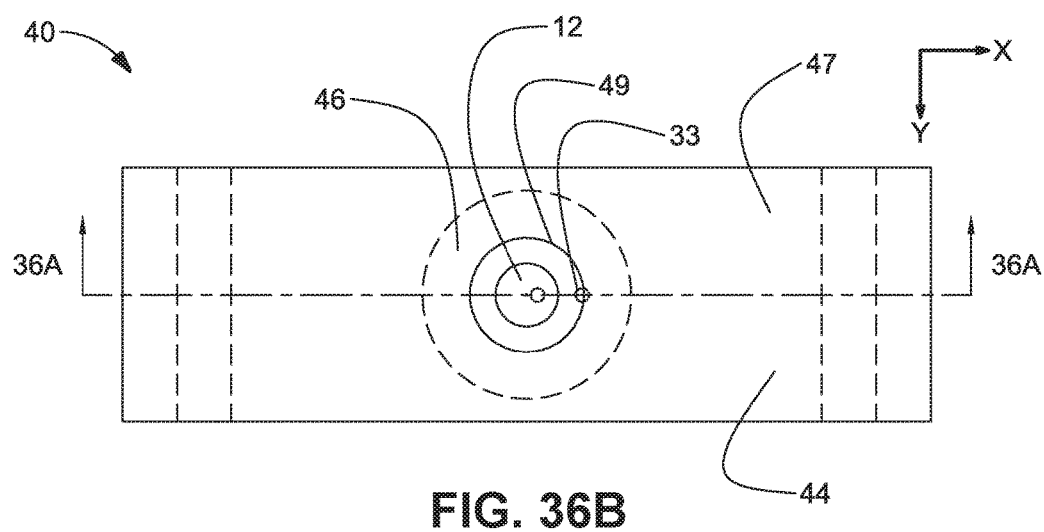

Similar to FIGS. 35A and 35B, the contaminate collector 40 of FIGS. 36A and 36B may include at least a stand 42 and a platform 44. However, unlike FIGS. 35A and 35B where the sidewalls 45 define a through-hole 46 with a truncated tetrahedron passage, the platform 44 of FIGS. 36A and 36B includes an internal cutout having a sidewall 45 that defines a truncated conical passage, including circular, oval, and elliptical conical passages. In operation, the removal of contaminate samples 33 from the tip 12 would follow the same procedure as described above with reference to FIGS. 35A and 35B, with the through-hole 46 being replaced with the truncated conical passage.

Figure 37A:
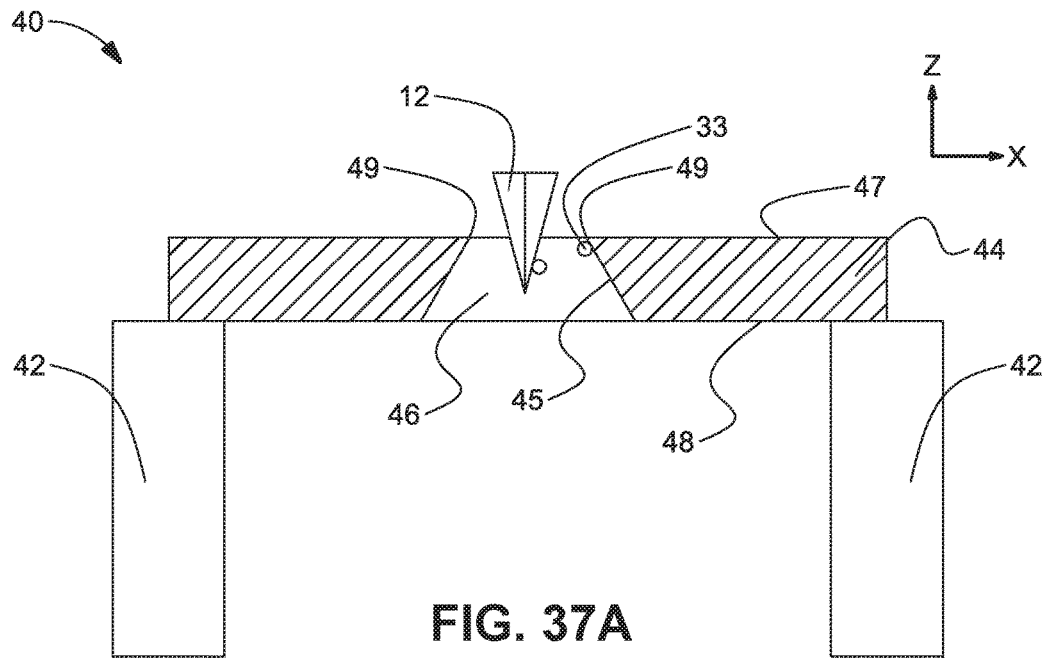
FIGS. 37A and 37B illustrate a side cross-sectional view and a top view, respectively, of a contaminate collector with a collection through-hole defining a truncated pyramidal passage in accordance with aspects of the present disclosure.
Figure 37B:
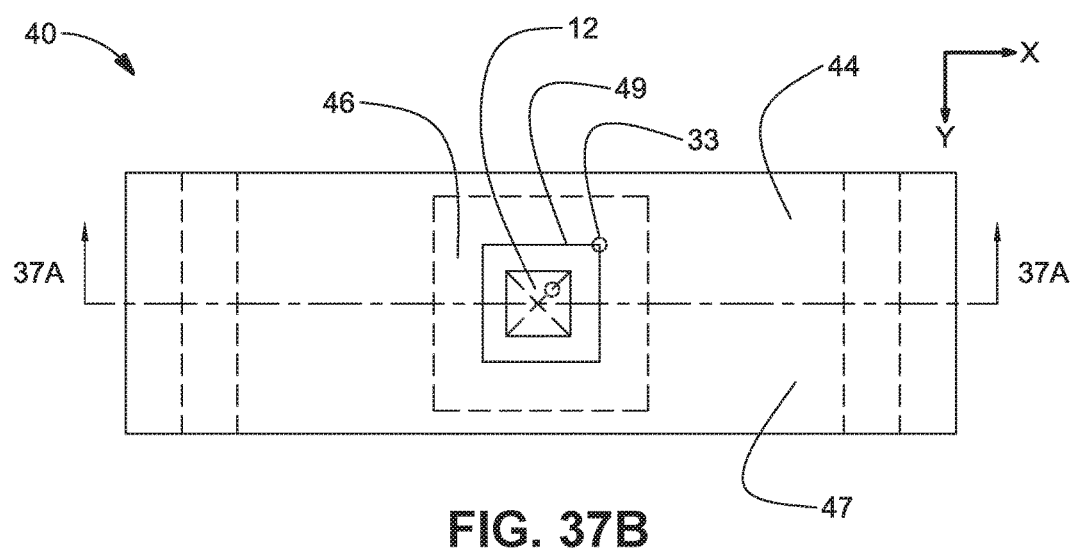

Similar to FIGS. 36A and 36B, the contaminate collector 40 of FIGS. 37A and 37B may include at least a stand 42 and a platform 44. However, unlike FIGS. 36A and 36B where the sidewall 45 defines a through-hole 46 with a truncated conical passage, the platform 44 of FIGS. 37A and 37B includes an internal cutout having a plurality of sidewalls 45 to define a collection through-hole 46. In accordance with an aspect of the present disclosure, the platform 44 may be provided with four sidewalls 45 to define a through-hole 46 with a truncated pyramidal passage. In operation, the removal of contaminate samples 33 from the tip 12 would follow the same procedure as described above with reference to FIGS. 35A and 35B, with the through-hole 46 being replaced with the truncated pyramidal passage.

Although truncated tetrahedron passage, truncated conical passages, and truncated pyramidal passages are described above with reference to FIGS. 35-37, other passage shapes for the through-hole 46 are contemplated, and the passage shapes may be selected based on a corresponding shape of the tip 12, including non-uniform shapes and where the through-hole may have three or more sidewalls. Of course, it would be apparent to one skilled in the art that other shapes and sizes of tips may be utilized with the contaminate collectors 40 of FIGS. 35-37.

Figure 38:
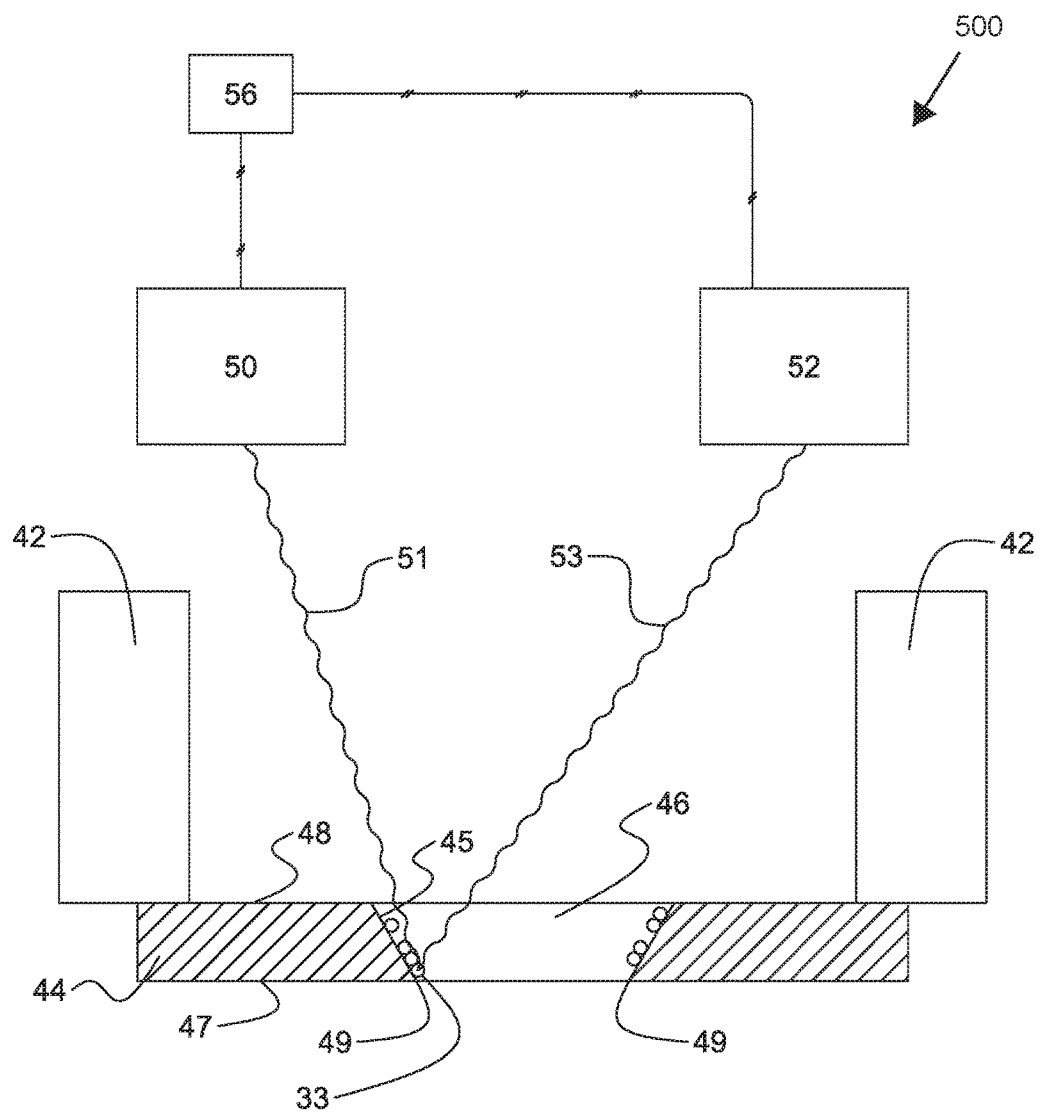
FIG. 38 illustrates a side cross-sectional view of a contaminate collector with a collection through-hole and a metrology system in accordance with aspects of the present disclosure.

The collection pockets 32 of FIGS. 30-32 and/or contaminate collectors 40 of FIGS. 35-37 may be usable together with the debris collection apparatus 100 of FIGS. 12-23 as described above, or they may be examined using a contamination analysis system 500 of FIG. 38, separate from the tip 12 and the associated actuation and control mechanisms. The collection pockets 32 of FIGS. 30-32 and/or the contaminate collectors 40 of FIGS. 35-37 may be used to collect debris while mounted at a first location, removed, transported to a second location, analyzed in a debris detection process, cleaned, and reused, as will be appreciated by one skilled in the art in view of the present disclosure.

As shown in FIG. 38, the contamination analysis system 500 may include an energy source 50 and an energy detector 52. When a contaminate collector 40 is ready to be examined or analyzed, the contaminate collector 40 may be placed or mounted onto the stand 42. The energy source 50 and the energy detector 52 may be co-located in a single unit, or they may be provided in separate units. The energy source 50 and the energy detector 52 may each be coupled to one or more actuators in order to move the energy source 50 and the energy detector 52 in one or more of the x-, y-, and z-directions, and/or rotate the energy source 50 and the energy detector 52 about the x-, y-, and z-directions. The energy source 50 and the energy detector 52 may be located above, below, or side-by-side with the contaminate collector 40 such that the energy source 50 and the energy detector 52 are operable to be trained on the collection lip edge 49 or the sidewall 45 of the contaminate collector 40.

During or after a contamination collection process whereby contaminate samples 33 are collected on the collection lip edge 49 and/or the sidewall 45 of the contaminate collector 40, the energy source 50 may be directed towards and trained on the collection lip edge 49 and/or the sidewall 45, such that an incident energy beam 51 generated by the energy source 50 is incident upon the lip edge 49 and/or the sidewall 45, and the energy detector 52 may be directed towards and trained on the lip edge 49 and/or the sidewall 45, such that a sample energy beam 53 generated in response to the incident energy beam 51 on the lip edge 49 and/or the sidewall 45 is received by the energy detector 52.

In accordance with aspects of the disclosure, the energy source 50, the energy detector 52, or combinations thereof, may operatively be coupled to a controller 56 for control thereof. Accordingly, the controller 56 may selectively aim and direct the incident energy beam 51 from the energy source 50 onto different surfaces of the lip edge 49 and/or the sidewall 45 by one or more actuators associated with the energy source 50. The controller 56 may further selectively aim and the energy detector 52 towards the different surfaces being exposed by the incident energy beam 51 in order to receive the sample energy beam 53 generated in response to the incident energy beam 51. The controller 56 may receive one or more signals from the energy detector 52 that are indicative of an attribute of the resulting sample energy beam 53.

The many features and advantages of the present disclosure are apparent from the detailed specification, and thus, it is intended by the appended claims to cover all such features and advantages of the invention which fall within the true spirit and scope of the invention. It is understood that the various aspects of the present disclosure may be combined and used together. Further, since numerous modifications and variations will be readily apparent to those skilled in the art in view of the present disclosure, it is not desired to limit the invention to the exact construction and operation illustrated and described, and accordingly, all suitable modifications and equivalents may be resorted to, falling within the scope of the invention.

What is claimed is:

1. A method for determining a composition of a particle using a scanning probe microscopy (SPM) tip, the method comprising:

picking up and transferring the particle to the SPM tip, wherein the SPM tip is configured to facilitate the particle pick-up;

irradiating the particle on the SPM tip with a first incident irradiation from an irradiation source;

detecting a first sample irradiation from the particle caused by the first incident irradiation with an irradiation detector;

identifying one or more material attributes from the detection to determine the composition of the particle; and effecting relative motion between the SPM tip and at least one of the irradiation source and the irradiation detector based on a first signal from the irradiation detector in response to the first sample irradiation.

2. The method of claim 1, further comprising:

generating a first frequency domain spectrum of the first sample irradiation based on the first signal, and generating a second frequency domain spectrum by subtracting a background frequency domain spectrum from the first frequency domain spectrum, and effecting relative motion between the SPM tip and at least one of the irradiation source and the irradiation detector based on the second frequency domain spectrum.

3. The method of claim 2, further comprising generating the background frequency domain spectrum based on a response of the irradiation detector to irradiation of the SPM tip when the SPM tip is substantially free from contamination.

4. The method of claim 1, further comprising:

irradiating the SPM tip with a second incident irradiation from the irradiation source;

detecting a second sample irradiation caused by the second incident irradiation with the irradiation detector; and effecting relative motion between the SPM tip and at least one of the irradiation source and the irradiation detector based on a second signal from the irradiation detector in response to the second sample irradiation.

5. The method of claim 4, further comprising effecting relative motion between the SPM tip and at least one of the irradiation source and the irradiation detector based on a difference between the second signal and the first signal.

6. The method of claim 1, wherein the first incident irradiation from the irradiation source is at least one of an x-ray, visible light, infrared light, ultraviolet light, an electron beam, and a laser.

7. The method of claim 4, wherein the second incident irradiation from the irradiation source is at least one of an x-ray, visible light, infrared light, ultraviolet light, an electron beam, and a laser.

8. The method of claim 7, wherein the second incident irradiation is a different type of irradiation than the first incident irradiation.

9. The method of claim 1, wherein the first sample irradiation is generated by the first incident irradiation interacting with the SPM tip.

10. The method of claim 1, wherein the first sample irradiation is generated by the first incident irradiation interacting with debris disposed on the SPM tip.

11. The method of claim 1, further comprising adjusting an intensity or frequency of the first incident irradiation from the irradiation source.

12. The method of claim 4, further comprising adjusting an intensity or frequency of the second incident irradiation from the irradiation source.

13. The method of claim 1, wherein the irradiation is carried out on the particle on the SPM tip in the SPM with a first incident irradiation from an irradiation source.

* * * * *